United States Patent
Kim et al.

(10) Patent No.: US 11,440,948 B2
(45) Date of Patent: Sep. 13, 2022

(54) MODIFIED NON-NATURAL NKG2D LIGANDS THAT SELECTIVELY DELIVER ATTACHED HETEROLOGOUS MOLECULES TO NON-NATURAL NKG2D RECEPTORS ON CAR-CELLS

(71) Applicants: Xyphos Biosciences Inc., South San Francisco, CA (US); The J. David Gladstone Institutes, A Testamentary Trust Established Under the Will of J. David Gladstone, San Francisco, CA (US)

(72) Inventors: Kaman Kim, South San Francisco, CA (US); Nigel Killeen, South San Francisco, CA (US); Eytan Herzig, South San Francisco, CA (US); Warner Greene, South San Francisco, CA (US)

(73) Assignees: Xyphos Biosciences Inc., South San Francisco, CA (US); THE J. DAVID GLADSTONE INSTITUTES, San Francisco, CA (US)

( * ) Notice: Subject to any disclaimer, the term of this patent is extended or adjusted under 35 U.S.C. 154(b) by 6 days.

(21) Appl. No.: 16/774,567

(22) Filed: Jan. 28, 2020

(65) Prior Publication Data
US 2020/0239541 A1    Jul. 30, 2020

Related U.S. Application Data

(60) Provisional application No. 62/797,644, filed on Jan. 28, 2019.

(51) Int. Cl.
 *C07K 14/16* (2006.01)
 *C07K 14/705* (2006.01)
 *C07K 16/10* (2006.01)

(52) U.S. Cl.
 CPC .......... *C07K 14/7056* (2013.01); *C07K 14/16* (2013.01); *C07K 16/1063* (2013.01); *C07K 2317/24* (2013.01); *C07K 2317/34* (2013.01)

(58) Field of Classification Search
 None
 See application file for complete search history.

(56) References Cited

U.S. PATENT DOCUMENTS

| | | | |
|---|---|---|---|
| 5,804,440 A | 9/1998 | Burton et al. | |
| 5,817,316 A | 10/1998 | Sodroski et al. | |
| 2010/0324034 A1 | 12/2010 | Hazuda et al. | |
| 2016/0176943 A1* | 6/2016 | Charreau | C07K 14/7056 424/9.1 |
| 2018/0134765 A1* | 5/2018 | Landgraf | C07K 16/2863 |

OTHER PUBLICATIONS

Xyphos Biosciences, Inc., "Convertible CAR-T Cells Provide Dose Control of Activity and Targeting Flexibility," CAR TCR Summit 2018, retrieved from the internet on Apr. 22, 2020, from <URL: https://xyphosinc.com/publications/xyphos-accel-technology-platform-poster/ >.
International Search Report, dated Jun. 12, 2020, issued by the International Searching Authority in International application No. PCT/US2020/015341.

* cited by examiner

*Primary Examiner* — Nianxiang Zou
(74) *Attorney, Agent, or Firm* — Sughrue Mion, PLLC

(57) ABSTRACT

This application relates generally to the production of modified, non-natural α1-α2 domains of NKG2D ligands with attached polypeptides having specific target-binding properties, for example, antibodies or variable fragments of antibodies, that are selectively delivered to Chimeric Antigen Receptors (CARs) comprised of modified, non-natural NKG2D receptors on engineered mammalian cells. The targeting of surface-expressed molecules includes those of virus-infected cells that can then be attacked and ablated by engineered cells of the immunity system expressing CARs cognate to the modified, non-natural α1-α2 domains of NKG2D ligands with attached polypeptides.

7 Claims, 17 Drawing Sheets
Specification includes a Sequence Listing.

FIGURE 5

```
MICA   HSLRYNLTVLSGDGSVQSGFLAEVHLDGQPFLRCDRQKCRAKPQGQWAEDVLGNKTWDRE
ULBP4  HSLCFNFTIKSLSRPGQPWCEAQVFLNKNLFLQYNSDNNMVKPLGLLGKKVYATSTWGEL
ULBP3  HSLWYNFTIIHLPRHGQQWCEVQSQVDQKNFLSYDCGSDKVLSMGHLEEQLYATDAWGKQ
ULBP1  HCLCYDFIITPKSRPEPQWCEVQGLVDERPFLHYDCVNHKAKAFASLGKKVNVTKTWEEQ
ULBP5  HSLCYDITVIPKFRPGPRWCAVQGQVDEKTFLHYDCGSKTVTPVSPLGKKLNVTTAWKAQ
ULBP2  HSLCYDITVIPKFRPGPRWCAVQGQVDEKTFLHYDCGNKTVTPVSPLGKKLNVTTAWKAQ
ULBP6  HSLCYDITVIPKFRPGPRWCAVQGQVDEKTFLHYDCGNKTVTPVSPLGKKLNVTTAWKAQ
        * *                              **                       *

MICA   TRDLTGNGKDLRMTLAHIKDQ---KEGLHSLQEIRVCEIHEDNSTRSSQHFYYDGELFLS
ULBP4  TQTLGEVGRDLRMLLCDIKP-QIKTSDPSTLQVEMFCQREAERCTGASWQFATNGEKSLL
ULBP3  LEMLREVGQRLRLELADTELEDFTPSGPLTLQVRMSCECEADGYIRGSWQFSFDGRKFLL
ULBP1  TETLRDVVDFLKGQLLDIQVENLIPIEPLTLQARMSCEHEAHGHGRGSWQFLFNGQKFLL
ULBP5  NPVLREVVDILTEQLLDIQLENYIPKEPLTLQARMSCEQKAEGHSGSWQLSFDGQIFLL
ULBP2  NPVLREVVDILTEQLRDIQLENYTPKEPLTLQARMSCEQKAEGHSSGSWQFSFDGQIFLL
ULBP6  NPVLREVVDILTEQLLDIQLENYTPKEPLTLQARMSCEQKAEGHSSGSWQFSIDGQTFLL
        *     *  *                **     *              *    *   *

MICA   QNLETEEWTMPQSSRAQTLAMNVRNFLKEDAMKTKTHYHAMHADCLQELRRYLK
ULBP4  FDAMNMTWTVINHEASKIKE----TWKKDRGLE-KYFRKLSKGDCDHWLREFLG
ULBP3  FDSNNRKWTVVHAGARRMKE----KWEKDSGLI-TFRDMVSRDCKSWLRDFLM
ULBP1  FDSNNRKWTALHPGAKKMTE----KWEKNRDVT-MFFQKISLGDCKMWLEEFLM
ULBP5  FDSENRMWTTVHPGARKMKE----KWENDKDMT-MSPHYISMGDCTGWLEDFLM
ULBP2  FDSEKRMWTTVHPGARKMKE----KWENDKVVA-MSFHYFSMGDCIGWLEDFLM
ULBP6  FDSEKRMWTTVHPGARKMKE----KWENDKDVA-MSFHYISMGDCIGWLEDFLM
        **                         **     *   *
```

FIGURE 11

| a1a2 variant | aa# in wt MICA: SEQ ID NO. | 20 | 68 | 69 | 125 | 152 | 154 | 158 | 161 | 166 |
|---|---|---|---|---|---|---|---|---|---|---|
| wt MICA | 42 | S | G | N | K | K | K | H | H | Q |
| MICwed | 55 | S | G | W | K | E | D | H | H | Q |
| DSM20 | 56 | S | A | W | L | Q | D | R | H | F |
| DSM25 | 57 | S | G | W | L | E | D | H | R | S |
| DSM27 | 58 | S | G | W | L | K | K | H | R | S |
| DSM28 | 59 | S | G | N | L | K | K | H | R | S |
| DSM42 | 60 | S | G | W | L | E | D | H | R | Q |
| DSM48 | 61 | S | G | W | L | A | D | I | R | A |
| DSM49 | 62 | T | Q | W | K | F | D | R | T | T |

FIGURE 12

| a1a2 variant | SEQ ID NO.: | Kd (M) | kon (1/Ms) | kdis (1/s) |
|---|---|---|---|---|
| wt MICA-Fv | 66 | 1.38E-08 | 1.30E+05 | 1.80E-03 |
| MICwed-Fv run A | 67 | 5.90E-09 | 2.90E+05 | 1.70E-03 |
| MICwed-Fv run B | 67 | 1.55E-08 | 2.01E+05 | 3.12E-03 |
| MICv20-Fv | 68 | 8.51E-11 | 3.59E+05 | 3.05E-05 |
| MICv25-Fv | 69 | 6.16E-11 | 4.67E+05 | 2.88E-05 |
| MICv27-Fv | 70 | 4.11E-10 | 2.08E+05 | 8.54E-05 |
| MICv28-Fv | 71 | 3.30E-10 | 2.46E+05 | 7.03E-05 |
| MICv42-Fv | 72 | 1.09E-10 | 3.47E+05 | 3.78E-05 |
| MICv48-Fv | 73 | 2.44E-10 | 5.95E+05 | 1.45E-04 |
| MICv49-Fv | 74 | 7.46E-10 | 3.70E+04 | 2.76E-05 |

FIGURE 13

| K71 | D72 | L73 | R74 | M75 | T155 | H156 | Y157 | H158 | A159 |
|-----|-----|-----|-----|-----|------|------|------|------|------|
| T   | T   | L   | L   | R   | I    | G    | G    | G    | L    |
| L   | F   |     |     | L   | R    | S    | S    | S    | I    |
| D   | R   |     |     |     | H    | R    | L    | L    | R    |
|     |     |     |     |     |      | W    |      |      |      |

FIGURE 14

| M154 | S155 | F156 | H157 | Y158 | F159 |
|------|------|------|------|------|------|
| T    | M    | L    | E    | L    | W    |
|      | K    | M    | T    | V    | I    |
|      | W    |      | S    | I    |      |
|      | L    |      | Q    | T    |      |
|      | T    |      | Y    |      |      |
|      |      |      | R    |      |      |

FIGURE 15

| F155 | F156 | K157 | M158 | V159 |
|------|------|------|------|------|
| D    | L    | I    | R    | R    |
| W    | M    | Y    | L    | I    |
| R    |      | V    | T    | W    |
| Y    |      | L    |      | K    |
| L    |      |      |      |      |

FIGURE 16

| ULBP2 variant | ULBP2 residue ||||||||  ELISA EC50s – Rituximab-MicAbody (light-chain ULBP2 fusion) binding to NKG2D.wt or NKG2D.AF ||||
| | 8 | 80 | 154 | 155 | 156 | 157 | 158 | 159 | wt EC50 nM | AF EC50 nM | wt/AF EC50 ratio | AF/wt EC50 ratio |
|---|---|---|---|---|---|---|---|---|---|---|---|---|
| | C | R | M | S | F | H | Y | F | | | | |
| A | S | W | T | T | F | W | Q | I | 28.95 | 0.061 | 471.12 | 0.00212 |
| B | S | W | T | M | L | R | Q | W | 34.18 | 0.025 | 1373.49 | 0.00073 |
| C | S | W | T | I | L | W | Q | T | 129.83 | 0.029 | 4414.23 | 0.00023 |
| D | S | W | T | L | L | W | Q | A | 10.02 | 0.020 | 489.80 | 0.00204 |
| E | S | W | T | L | L | W | S | W | 51.45 | 0.031 | 1650.77 | 0.00061 |
| F | S | W | T | V | L | W | Q | A | 37.58 | 0.023 | 1639.79 | 0.00061 |
| G | S | W | T | V | L | W | S | A | 40.54 | 0.024 | 1664.58 | 0.00060 |
| I | S | W | T | N | I | W | Q | Y | 1.04 | 0.010 | 99.11 | 0.01009 |
| J | S | W | T | H | L | W | G | W | 5.77 | 0.062 | 93.61 | 0.01068 |
| L | S | W | T | L | F | W | Q | S | 25.33 | 0.053 | 479.31 | 0.00209 |
| O | S | W | T | S | L | W | Q | S | 17.04 | 0.026 | 652.71 | 0.00153 |
| P | S | W | T | M | L | R | Q | F | 2.37 | 0.069 | 34.45 | 0.02903 |
| R | S | W | T | L | L | W | G | W | 104.45 | 0.031 | 3398.27 | 0.00029 |
| T | S | W | T | L | L | W | Q | W | 4.37 | 0.029 | 151.52 | 0.00660 |
| U | S | W | T | M | L | W | K | W | 19.58 | 0.033 | 595.39 | 0.00168 |
| W | S | W | T | M | F | R | Q | W | 27.09 | 0.020 | 1322.15 | 0.00076 |
| Y | S | W | T | S | L | W | S | W | 83.49 | 0.090 | 927.71 | 0.00108 |
| Z | S | W | T | N | L | W | S | A | 98.80 | 0.025 | 3892.50 | 0.00026 |
| AA | S | W | T | M | F | W | S | W | 654.83 | 0.033 | 20092.30 | 0.00005 |
| AB | S | W | T | L | M | W | Q | W | 389.34 | 0.036 | 10801.65 | 0.00009 |
| AD | S | W | T | T | L | W | Q | V | 57.33 | 0.038 | 1504.95 | 0.00066 |

FIGURE 17

| M154 | S155 | F156 | H157 | Y158 | F159 |
|------|------|------|------|------|------|
| T    | M    | L    | E    | L    | W    |
|      | K    | M    | T    | V    | I    |
|      | W    |      | S    | I    |      |
|      | L    |      | Q    | T    |      |
|      | T    |      | Y    |      |      |
|      |      |      | R    |      |      |

SEQUENCE LISTING

```
<160> NUMBER OF SEQ ID NOS: 177

<210> SEQ ID NO 1
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 1

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
```

```
            50                  55                  60
Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Glu Trp Thr
         115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 2
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 2

Glu Pro His Ser Leu Arg Tyr Asn Leu Thr Val Leu Ser Trp Asp Gly
 1               5                  10                  15

Ser Val Gln Ser Gly Phe Leu Ala Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
        50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Glu Trp Thr
         115                 120                 125

Met Pro Gln Ser Ser Arg Ala Gln Thr Leu Ala Met Asn Ile Arg Asn
    130                 135                 140
```

```
Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
            165                 170                 175

Val Leu Arg Arg Thr Val Pro Pro Met Val Asn Val Thr Arg Ser Glu
        180                 185                 190

Ala Ser Glu Gly Asn Ile Thr Val Thr Cys Arg Ala Ser Gly Phe Tyr
    195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
        260                 265                 270

Pro Ser

<210> SEQ ID NO 3
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 3

Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
            85                  90                  95

Glu Ile His Glu Asp Asn Ser Thr Arg Ser Ser Gln His Phe Tyr Tyr
        100                 105                 110

Asp Gly Glu Leu Phe Leu Ser Gln Asn Leu Glu Thr Glu Glu Trp Thr
    115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
            165                 170                 175

Val Leu Arg Arg Thr Val Pro Pro Met Val Asn Val Thr Arg Ser Glu
        180                 185                 190

Ala Ser Glu Gly Asn Ile Thr Val Thr Cys Arg Ala Ser Gly Phe Tyr
    195                 200                 205

Pro Trp Asn Ile Thr Leu Ser Trp Arg Gln Asp Gly Val Ser Leu Ser
210                 215                 220
```

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
            260                 265                 270

Pro Ser

<210> SEQ ID NO 4
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 4

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Val Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
            260                 265                 270

Pro Ser

<210> SEQ ID NO 5
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 5

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser
```

<210> SEQ ID NO 6
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 6

```
Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60
```

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 7
<211> LENGTH: 276
<212> TYPE: PRT
<213> ORGANISM: Artificial Sequence
<220> FEATURE:
<223> OTHER INFORMATION: Synthetic peptide MICA

<400> SEQUENCE: 7

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
        50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

```
Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
        260                 265                 270

Pro Ser Gly Lys
        275

<210> SEQ ID NO 8
<211> LENGTH: 306
<212> TYPE: PRT
<213> ORGANISM: Artificial Sequence
<220> FEATURE:
<223> OTHER INFORMATION: Synthetic peptide MICB

<400> SEQUENCE: 8

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Lys Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Leu Pro Pro Met Val Asn Val
                165                 170                 175

Ile Cys Ser Glu Val Ser Glu Gly Asn Ile Thr Val Thr Cys Arg Ala
            180                 185                 190

Ser Ser Phe Tyr Pro Arg Asn Ile Thr Leu Thr Trp Arg Gln Asp Gly
        195                 200                 205

Val Ser Leu Ser His Asn Thr Gln Gln Trp Gly Asp Val Leu Pro Asp
210                 215                 220
```

Gly Asn Gly Thr Tyr Gln Thr Trp Val Ala Thr Arg Ile Arg Gln Gly
225                 230                 235                 240

Glu Glu Gln Arg Phe Thr Cys Tyr Met Glu His Ser Gly Asn His Gly
            245                 250                 255

Thr His Pro Val Pro Ser Gly Lys Ala Leu Val Leu Gln Ser Gln Arg
        260                 265                 270

Thr Asp Phe Pro Tyr Val Ser Ala Ala Met Pro Cys Phe Val Ile Ile
    275                 280                 285

Ile Ile Leu Cys Val Pro Cys Cys Lys Lys Thr Ser Ala Ala Glu
290                 295                 300

Gly Pro
305

<210> SEQ ID NO 9
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 9

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Glu Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Met His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

```
Pro Ser Gly Lys Ala Leu Val Leu Gln Ser Gln Arg Thr Asp Phe Pro
            275                 280                 285

Tyr Val Ser Ala Ala Met Pro Cys Phe Val Ile Ile Ile Ile Leu Cys
            290                 295                 300

Val Pro Cys Cys Lys Lys Lys Thr Ser Ala Ala Glu Gly Pro
305                 310                 315

<210> SEQ ID NO 10
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 10

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
            35                  40                  45

Trp Ala Glu Asp Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Ile Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Ile Leu Cys
            290                 295                 300

Val Pro Cys Cys Lys Lys Lys Thr Ser Ala Ala Glu Gly Pro
305                 310                 315
```

```
<210> SEQ ID NO 11
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 11
```

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
                20                  25                  30

Phe Leu Arg Tyr Asp Arg Gln Lys Arg Arg Ala Lys Pro Gln Gly Gln
            35                  40                  45

Trp Ala Glu Asn Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Leu Cys
290                 295                 300

Val Pro Cys Cys Lys Lys Lys Thr Ser Ala Ala Glu Gly Pro
305                 310                 315

```
<210> SEQ ID NO 12
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 12
```

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Ala Lys Pro Gln Gly Gln
        35                  40                  45

Trp Ala Glu Asp Val Leu Gly Ala Glu Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
                100                 105                 110

Asn Gly Glu Leu Phe Leu Ser Gln Asn Leu Glu Thr Gln Glu Ser Thr
            115                 120                 125

Val Pro Gln Ser Ser Arg Ala Gln Thr Leu Ala Met Asn Val Thr Asn
            130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
                180                 185                 190

Val Ser Glu Gly Asn Ile Thr Val Thr Cys Arg Ala Ser Ser Phe Tyr
            195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Lys
            245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
            275                 280                 285

Tyr Val Ser Ala Ala Met Pro Cys Phe Val Ile Ile Ile Leu Cys
            290                 295                 300

Val Pro Cys Cys Lys Lys Thr Ser Ala Ala Glu Gly Pro
305                 310                 315

<210> SEQ ID NO 13
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 13

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Ala Lys Pro Gln Gly Gln
        35                  40                  45

Trp Ala Glu Asp Val Leu Gly Ala Glu Thr Trp Asp Thr Glu Thr Glu
 50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Leu Cys
290                 295                 300

Val Pro Cys Cys Lys Lys Lys Thr Ser Ala Ala Glu Gly Pro
305                 310                 315

<210> SEQ ID NO 14
<211> LENGTH: 244
<212> TYPE: PRT
<213> ORGANISM: Artificial Sequence
<220> FEATURE:
<223> OTHER INFORMATION: Synthetic peptide ULBP-1 (ACCESSION NO Q9BZM6)

<400> SEQUENCE: 14

Met Ala Ala Ala Ser Pro Ala Phe Leu Leu Cys Leu Pro Leu Leu
1               5                   10                  15

His Leu Leu Ser Gly Trp Ser Arg Ala Gly Trp Val Asp Thr His Cys
                20                  25                  30

Leu Cys Tyr Asp Phe Ile Ile Thr Pro Lys Ser Arg Pro Glu Pro Gln
            35                  40                  45

Trp Cys Glu Val Gln Gly Leu Val Asp Glu Arg Pro Phe Leu His Tyr
        50                  55                  60

Asp Cys Val Asn His Lys Ala Lys Ala Phe Ala Ser Leu Gly Lys Lys
65                  70                  75                  80

Val Asn Val Thr Lys Thr Trp Glu Glu Gln Thr Glu Thr Leu Arg Asp
                85                  90                  95

```
Val Val Asp Phe Leu Lys Gly Gln Leu Leu Asp Ile Gln Val Glu Asn
            100                 105                 110

Leu Ile Pro Ile Glu Pro Leu Thr Leu Gln Ala Arg Met Ser Cys Glu
            115                 120                 125

His Glu Ala His Gly His Gly Arg Gly Ser Trp Gln Phe Leu Phe Asn
        130                 135                 140

Gly Gln Lys Phe Leu Leu Phe Asp Ser Asn Asn Arg Lys Trp Thr Ala
145                 150                 155                 160

Leu His Pro Gly Ala Lys Lys Met Thr Glu Lys Trp Glu Lys Asn Arg
                165                 170                 175

Asp Val Thr Met Phe Phe Gln Lys Ile Ser Leu Gly Asp Cys Lys Met
            180                 185                 190

Trp Leu Glu Glu Phe Leu Met Tyr Trp Glu Gln Met Leu Asp Pro Thr
        195                 200                 205

Lys Pro Pro Ser Leu Ala Pro Gly Thr Thr Gln Pro Lys Ala Met Ala
    210                 215                 220

Thr Thr Leu Ser Pro Trp Ser Leu Leu Ile Ile Phe Leu Cys Phe Ile
225                 230                 235                 240

Leu Ala Gly Arg

<210> SEQ ID NO 15
<211> LENGTH: 246
<212> TYPE: PRT
<213> ORGANISM: Artificial Sequence
<220> FEATURE:
<223> OTHER INFORMATION: Synthetic peptide ULBP-2 (ACCESSION NO Q9BZM5)

<400> SEQUENCE: 15

Met Ala Ala Ala Ala Thr Lys Ile Leu Leu Cys Leu Pro Leu Leu
1               5                   10                  15

Leu Leu Leu Ser Gly Trp Ser Arg Ala Gly Arg Ala Asp Pro His Ser
            20                  25                  30

Leu Cys Tyr Asp Ile Thr Val Ile Pro Lys Phe Arg Pro Gly Pro Arg
        35                  40                  45

Trp Cys Ala Val Gln Gly Gln Val Asp Glu Lys Thr Phe Leu His Tyr
    50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
            115                 120                 125

Gln Lys Ala Glu Gly His Ser Ser Gly Ser Trp Gln Phe Ser Phe Asp
        130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205
```

```
Ala Gly Ala Pro Leu Ala Met Ser Ser Gly Thr Thr Gln Leu Arg Ala
        210                 215                 220

Thr Ala Thr Thr Leu Ile Leu Cys Cys Leu Leu Ile Ile Leu Pro Cys
225                 230                 235                 240

Phe Ile Leu Pro Gly Ile
                245
```

<210> SEQ ID NO 16
<211> LENGTH: 244
<212> TYPE: PRT
<213> ORGANISM: Artificial Sequence
<220> FEATURE:
<223> OTHER INFORMATION: Synthetic peptide ULBP-3 (ACCESSION NO NP_078794)

<400> SEQUENCE: 16

```
Met Ala Ala Ala Ser Pro Ala Ile Leu Pro Arg Leu Ala Ile Leu
1               5                   10                  15

Pro Tyr Leu Leu Phe Asp Trp Ser Gly Thr Gly Arg Ala Asp Ala His
            20                  25                  30

Ser Leu Trp Tyr Asn Phe Thr Ile Ile His Leu Pro Arg His Gly Gln
        35                  40                  45

Gln Trp Cys Glu Val Gln Ser Gln Val Asp Gln Lys Asn Phe Leu Ser
    50                  55                  60

Tyr Asp Cys Gly Ser Asp Lys Val Leu Ser Met Gly His Leu Glu Glu
65                  70                  75                  80

Gln Leu Tyr Ala Thr Asp Ala Trp Gly Lys Gln Leu Glu Met Leu Arg
                85                  90                  95

Glu Val Gly Gln Arg Leu Arg Leu Glu Leu Ala Asp Thr Glu Leu Glu
            100                 105                 110

Asp Phe Thr Pro Ser Gly Pro Leu Thr Leu Gln Val Arg Met Ser Cys
        115                 120                 125

Glu Cys Glu Ala Asp Gly Tyr Ile Arg Gly Ser Trp Gln Phe Ser Phe
    130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
                165                 170                 175

Ser Gly Leu Thr Thr Phe Phe Lys Met Val Ser Met Arg Asp Cys Lys
            180                 185                 190

Ser Trp Leu Arg Asp Phe Leu Met His Arg Lys Lys Arg Leu Glu Pro
        195                 200                 205

Thr Ala Pro Pro Thr Met Ala Pro Gly Leu Ala Gln Pro Lys Ala Ile
    210                 215                 220

Ala Thr Thr Leu Ser Pro Trp Ser Phe Leu Ile Ile Leu Cys Phe Ile
225                 230                 235                 240

Leu Pro Gly Ile
```

<210> SEQ ID NO 17
<211> LENGTH: 263
<212> TYPE: PRT
<213> ORGANISM: Artificial Sequence
<220> FEATURE:
<223> OTHER INFORMATION: Synthetic peptide ULBP-4/RAET1E (ACCESSION NO Q8TD07)

<400> SEQUENCE: 17

```
Met Arg Arg Ile Ser Leu Thr Ser Ser Pro Val Arg Leu Leu Leu Phe
```

```
                1               5                  10                 15
Leu Leu Leu Leu Leu Ile Ala Leu Glu Ile Met Val Gly Gly His Ser
                   20                 25                 30
Leu Cys Phe Asn Phe Thr Ile Lys Ser Leu Ser Arg Pro Gly Gln Pro
                   35                 40                 45
Trp Cys Glu Ala Gln Val Phe Leu Asn Lys Asn Leu Phe Leu Gln Tyr
                   50                 55                 60
Asn Ser Asp Asn Met Val Lys Pro Leu Gly Leu Gly Lys Lys
 65                 70                 75                 80
Val Tyr Ala Thr Ser Thr Trp Gly Leu Thr Gln Thr Leu Gly Glu
                   85                 90                 95
Val Gly Arg Asp Leu Arg Met Leu Leu Cys Asp Ile Lys Pro Gln Ile
                  100                105                110
Lys Thr Ser Asp Pro Ser Thr Leu Gln Val Glu Met Phe Cys Gln Arg
                  115                120                125
Glu Ala Glu Arg Cys Thr Gly Ala Ser Trp Gln Phe Ala Thr Asn Gly
                  130                135                140
Glu Lys Ser Leu Leu Phe Asp Ala Met Asn Met Thr Trp Thr Val Ile
145                150                155                160
Asn His Glu Ala Ser Lys Ile Lys Glu Thr Trp Lys Lys Asp Arg Gly
                  165                170                175
Leu Glu Lys Tyr Phe Arg Lys Leu Ser Lys Gly Asp Cys Asp His Trp
                  180                185                190
Leu Arg Glu Phe Leu Gly His Trp Glu Ala Met Pro Glu Pro Thr Val
                  195                200                205
Ser Pro Val Asn Ala Ser Asp Ile His Trp Ser Ser Ser Leu Pro
                  210                215                220
Asp Arg Trp Ile Ile Leu Gly Ala Phe Ile Leu Val Leu Met Gly
225                230                235                240
Ile Val Leu Ile Cys Val Trp Trp Gln Asn Gly Glu Trp Gln Ala Gly
                  245                250                255
Leu Trp Pro Leu Arg Thr Ser
                  260
```

<210> SEQ ID NO 18
<211> LENGTH: 332
<212> TYPE: PRT
<213> ORGANISM: Artificial Sequence
<220> FEATURE:
<223> OTHER INFORMATION: Synthetic peptide ULBP-5 (ACCESSION NO Q6H3X3)

<400> SEQUENCE: 18

```
                1               5                  10                 15
Met Ala Ala Ala Ala Ser Pro Ala Phe Leu Leu Arg Leu Pro Leu Leu
                   20                 25                 30
Leu Leu Leu Ser Ser Trp Cys Arg Thr Gly Leu Ala Asp Pro His Ser
                   35                 40                 45
Leu Cys Tyr Asp Ile Thr Val Pro Lys Phe Arg Pro Gly Pro Arg Trp
                   50                 55                 60
Cys Ala Val Gln Gly Gln Val Asp Glu Lys Thr Phe Leu His Tyr Asp
                   70                 75                 80
Cys Gly Ser Lys Thr Val Thr Pro Val Ser Pro Leu Gly Lys Lys Leu
 65
                   85                 90                 95
Asn Val Thr Thr Ala Trp Lys Ala Gln Asn Pro Val Leu Arg Glu Val

Val Asp Leu Thr Glu Gln Leu Leu Asp Ile Gln Leu Glu Asn Tyr Ile
```

```
            100                 105                 110
Pro Lys Glu Pro Leu Thr Leu Gln Ala Arg Met Ser Cys Glu Gln Lys
            115                 120                 125

Ala Glu Gly His Gly Ser Gly Ser Trp Gln Leu Ser Phe Asp Gly Gln
            130                 135                 140

Ile Phe Leu Leu Phe Asp Ser Glu Asn Arg Met Trp Thr Thr Val His
145                 150                 155                 160

Pro Gly Ala Arg Lys Met Lys Glu Lys Trp Glu Asn Asp Lys Asp Met
            165                 170                 175

Thr Met Ser Phe His Tyr Ile Ser Met Gly Asp Cys Thr Gly Trp Leu
            180                 185                 190

Glu Asp Phe Leu Met Gly Met Asp Ser Thr Leu Glu Pro Ser Ala Gly
            195                 200                 205

Ala Pro Pro Thr Met Ser Ser Gly Thr Ala Gln Pro Arg Ala Thr Ala
            210                 215                 220

Thr Thr Leu Ile Leu Cys Cys Leu Leu Ile Met Cys Leu Leu Ile Cys
225                 230                 235                 240

Ser Arg His Ser Leu Thr Gln Ser His Gly His His Pro Gln Ser Leu
            245                 250                 255

Gln Pro Pro Pro His Pro Pro Leu Leu His Pro Thr Trp Leu Leu Arg
            260                 265                 270

Arg Val Leu Trp Ser Asp Ser Tyr Gln Ile Ala Lys Arg Pro Leu Ser
            275                 280                 285

Gly Gly His Val Thr Arg Val Thr Leu Pro Ile Ile Gly Asp Asp Ser
            290                 295                 300

His Ser Leu Pro Cys Pro Leu Ala Leu Tyr Thr Ile Asn Asn Gly Ala
305                 310                 315                 320

Ala Arg Tyr Ser Glu Pro Leu Gln Val Ser Ile Ser
            325                 330

<210> SEQ ID NO 19
<211> LENGTH: 246
<212> TYPE: PRT
<213> ORGANISM: Artificial Sequence
<220> FEATURE:
<223> OTHER INFORMATION: Synthetic peptide ULBP-6 (ACCESSION NO
      NP_570970)

<400> SEQUENCE: 19

Met Ala Ala Ala Ile Pro Ala Leu Leu Leu Cys Leu Pro Leu Leu Leu
1               5                   10                  15

Phe Leu Leu Phe Gly Trp Ser Arg Ala Arg Arg Asp Asp Pro His Ser
            20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65              70                  75                  80

Leu Asn Val Thr Met Ala Trp Lys Ala Gln Asn Pro Val Leu Arg Glu
            85                  90                  95

Val Val Asp Ile Leu Thr Glu Gln Leu Leu Asp Ile Gln Leu Glu Asn
            100                 105                 110

Tyr Thr Pro Lys Glu Pro Leu Thr Leu Gln Ala Arg Met Ser Cys Glu
            115                 120                 125
```

```
Gln Lys Ala Glu Gly His Ser Ser Gly Ser Trp Gln Phe Ser Ile Asp
    130                 135                 140

Gly Gln Thr Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Asp Val Ala Met Ser Phe His Tyr Ile Ser Met Gly Asp Cys Ile Gly
                180                 185                 190

Trp Leu Glu Asp Phe Leu Met Gly Met Asp Ser Thr Leu Glu Pro Ser
            195                 200                 205

Ala Gly Ala Pro Leu Ala Met Ser Ser Gly Thr Thr Gln Leu Arg Ala
        210                 215                 220

Thr Ala Thr Thr Leu Ile Leu Cys Cys Leu Leu Ile Ile Leu Pro Cys
225                 230                 235                 240

Phe Ile Leu Pro Gly Ile
                245

<210> SEQ ID NO 20
<211> LENGTH: 558
<212> TYPE: PRT
<213> ORGANISM: Artificial Sequence
<220> FEATURE:
<223> OTHER INFORMATION: Synthetic peptide MICA-WED

<400> SEQUENCE: 20

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240
```

```
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
            260                 265                 270
Ser Tyr Thr Thr Pro Pro Thr Phe Gly Gln Gly Thr Lys Val Glu Ile
        275                 280                 285
Lys Gly Gly Ser Ser Arg Ser Ser Ser Gly Gly Gly Gly Ser Gly
    290                 295                 300
Gly Gly Gly Glu Val Gln Leu Val Glu Ser Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
        355                 360                 365
Asp Ser Val Lys Gly Arg Phe Thr Ile Ser Ala Asp Thr Ser Lys Asn
    370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Gly Gly Gly Gly Ser
        435                 440                 445
Gly Gly Gly Gly Asp Ile Gln Met Thr Gln Ser Pro Ser Ser Leu Ser
    450                 455                 460
Ala Ser Gly Gly Ser Gly Gln Ile Thr Val Thr Cys Arg Ala Ser Gly
465                 470                 475                 480
Phe Tyr Pro Trp Asn Ile Thr Leu Ser Trp Arg Gln Asp Gly Val Ser
                485                 490                 495
Leu Ser His Asp Thr Gln Gln Trp Gly Asp Val Leu Pro Asp Gly Gln
            500                 505                 510
Gly Thr Tyr Gln Thr Trp Val Ala Thr Arg Ile Ser Gln Gly Glu Glu
        515                 520                 525
Gln Arg Phe Thr Cys Tyr Met Glu His Ser Gly Gln His Ser Thr His
    530                 535                 540
Pro Val Pro Ser Gly Lys Gly Ser His His His His His
545                 550                 555
```

<210> SEQ ID NO 21
<211> LENGTH: 507
<212> TYPE: DNA
<213> ORGANISM: Artificial Sequence
<220> FEATURE:
<223> OTHER INFORMATION: Synthetic polynucleotide, encoding alpha1-
    alpha2 variant 15

<400> SEQUENCE: 21

```
gctgctgagc cacacagtct ccgctacaac cttacggtgt tgagctggga cggctctgtc    60
cagagtggct ttctgactga ggtacatctc gatggtcagc ccttcctccg atgcgacaga   120
caaaagtgca gggccaagcc acagggccaa tgggccgaag atgtacttgg caataagact   180
tgggacagag aaaccagaga tctgactggc tggggtaagg acttacgcat gactctcgca   240
```

```
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccaa cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507
```

<210> SEQ ID NO 22
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 16

<400> SEQUENCE: 22

```
gctgctgagc cacacagtct ccgctacaac cttacggtgt tgagctggga cggctctgtc     60
cagagtggct ttctgactga ggtacatctc gatggtcagc ccttcctccg atgcgacaga    120
caaaagtgca gggccaagcc acagggccaa tgggccgaag atgtacttgg caataagact    180
tgggacagag aaaccagaga tctgactggc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507
```

<210> SEQ ID NO 23
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 17

<400> SEQUENCE: 23

```
gctgctgagc cacacagtct ccgctacaac cttacggtgt tgagctggga cggctctgtc     60
cagagtggct ttctgactga ggtacatctc gatggtcagc ccttcctccg atgcgacaga    120
caaaagtgca gggccaagcc acagggccaa tgggccgaag atgtacttgg caataagact    180
tgggacagag aaaccagaga tctgactctc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507
```

<210> SEQ ID NO 24
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 18

<400> SEQUENCE: 24

```
gctgctgagc cacacagtct ccgctacaac cttacggtgt tgagctggga cggctctgtc    60
cagcccggct ttctgactga ggtacatctc gatggtcagc ccttcctccg atgcgacaga   120
caaaagtgca gggccaagcc acagggccaa tgggccgaag atgtacttgg caataagact   180
tgggacagag aaaccagaga tctgactctc tggggtaagg acttacgcat gactctcgca   240
cacattaaag accagaagga aggtcttcat tcgctccagg aaattagagt ctgtgaaatc   300
catgaagaca cagcacaag aagttcccaa catttctact acgacggcga gctgttctta   360
tcacagaatt tagagaccct cgagtggaca atgccccaaa gctcgagggc ccagaccctc   420
gctatgaatg tgaggaattt ccttaaggag gacgctatgg aaactgacac ccactaccat   480
gcgatgcgcg ccgattgcct gcaggaa                                       507
```

<210> SEQ ID NO 25
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 15

<400> SEQUENCE: 25

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Asn Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270
```

```
Ser Tyr Thr Thr Pro Pro Thr Phe Gly Gln Gly Thr Lys Val Glu Ile
            275                 280                 285

Lys Gly Gly Ser Ser Arg Ser Ser Ser Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
        340                 345                 350

Glu Trp Val Gly Arg Ile Tyr Pro Thr Asn Gly Ser Thr Asn Tyr Ala
    355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
        500                 505                 510

Gly Thr Tyr Gln Thr Trp Val Ala Thr Arg Ile Ser Gln Gly Glu Glu
    515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 26
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 16

<400> SEQUENCE: 26

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80
```

-continued

Lys Asp Gln Lys Glu Gly Leu His Ser Leu Gln Glu Ile Arg Val Cys
            85                  90                  95
Glu Ile His Glu Asp Asn Ser Thr Arg Ser Ser Gln His Phe Tyr Tyr
        100                 105                 110
Asp Gly Glu Leu Phe Leu Ser Gln Asn Leu Glu Thr Leu Glu Trp Thr
        115                 120                 125
Met Pro Gln Ser Ser Arg Ala Gln Thr Leu Ala Met Asn Val Arg Asn
        130                 135                 140
Phe Leu Lys Glu Asp Ala Met Glu Thr Asp Thr His Tyr His Ala Met
145                 150                 155                 160
Arg Ala Asp Cys Leu Gln Glu Leu Arg Arg Tyr Leu Lys Ser Gly Val
                165                 170                 175
Val Leu Arg Arg Thr Val Pro Pro Met Val Gln Val Thr Arg Ser Glu
            180                 185                 190
Ala Ser Gly Gly Ser Gly Asp Arg Val Thr Ile Thr Cys Arg Ala Ser
        195                 200                 205
Gln Asp Val Ser Thr Ala Val Ala Trp Tyr Gln Gln Lys Pro Gly Lys
        210                 215                 220
Ala Pro Lys Leu Leu Ile Tyr Ser Ala Ser Phe Leu Tyr Ser Gly Val
225                 230                 235                 240
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
            260                 265                 270
Ser Tyr Thr Thr Pro Pro Thr Phe Gly Gln Gly Thr Lys Val Glu Ile
        275                 280                 285
Lys Gly Gly Ser Ser Arg Ser Ser Ser Gly Gly Gly Gly Ser Gly
        290                 295                 300
Gly Gly Gly Glu Val Gln Leu Val Glu Ser Gly Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
        355                 360                 365
Asp Ser Val Lys Gly Arg Phe Thr Ile Ser Ala Asp Thr Ser Lys Asn
        370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Gly Gly Gly Gly Ser
        435                 440                 445
Gly Gly Gly Gly Asp Ile Gln Met Thr Gln Ser Pro Ser Ser Leu Ser
        450                 455                 460
Ala Ser Gly Gly Ser Gly Gln Ile Thr Val Thr Cys Arg Ala Ser Gly
465                 470                 475                 480
Phe Tyr Pro Trp Asn Ile Thr Leu Ser Trp Arg Gln Asp Gly Val Ser
                485                 490                 495
Leu Ser His Asp Thr Gln Gln Trp Gly Asp Val Leu Pro Asp Gly Gln

```
                500             505             510
Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
            530                 535                 540

Pro Val Pro Ser Gly Lys Gly Ser His His His His His His
545                 550                 555
```

<210> SEQ ID NO 27
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 17

<400> SEQUENCE: 27

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Leu Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Ser Gly
    290                 295                 300

Gly Gly Gly Glu Val Gln Leu Val Glu Ser Gly Gly Gly Leu Val Gln
```

```
                305                 310                 315                 320
Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 28
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 18

<400> SEQUENCE: 28

Glu Pro His Ser Leu Arg Tyr Asn Leu Thr Val Leu Ser Trp Asp Gly
1               5                   10                  15

Ser Val Gln Pro Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Leu Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
```

```
            115                 120                 125
Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
    290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
    450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540
```

```
Pro Val Pro Ser Gly Lys Gly Ser His His His His His His
545                 550                 555
```

```
<210> SEQ ID NO 29
<211> LENGTH: 182
<212> TYPE: PRT
<213> ORGANISM: Artificial Sequence
<220> FEATURE:
<223> OTHER INFORMATION: Synthetic peptide MICwed alpha1-alpha2

<400> SEQUENCE: 29
```

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val
            180
```

```
<210> SEQ ID NO 30
<211> LENGTH: 182
<212> TYPE: PRT
<213> ORGANISM: Artificial Sequence
<220> FEATURE:
<223> OTHER INFORMATION: Synthetic peptide DSM20 alpha1-alpha2

<400> SEQUENCE: 30
```

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Ala Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
```

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Gln Thr Asp Thr His Tyr Arg Ala Met
145                 150                 155                 160

His Ala Asp Cys Leu Phe Glu Leu Arg Arg Tyr Leu Lys Ser Gly Val
                165                 170                 175

Val Leu Arg Arg Thr Val
            180

<210> SEQ ID NO 31
<211> LENGTH: 182
<212> TYPE: PRT
<213> ORGANISM: Artificial Sequence
<220> FEATURE:
<223> OTHER INFORMATION: Synthetic peptide DSM25 alpha1-alpha2

<400> SEQUENCE: 31

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 32
<211> LENGTH: 182
<212> TYPE: PRT
<213> ORGANISM: Artificial Sequence
<220> FEATURE:
<223> OTHER INFORMATION: Synthetic peptide DSM27 alpha1-alpha2

<400> SEQUENCE: 32

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

```
Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Leu Glu Trp Thr
             115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 33
<211> LENGTH: 182
<212> TYPE: PRT
<213> ORGANISM: Artificial Sequence
<220> FEATURE:
<223> OTHER INFORMATION: Synthetic peptide DSM28 alpha1-alpha2

<400> SEQUENCE: 33

Glu Pro His Ser Leu Arg Tyr Asn Leu Thr Val Leu Ser Trp Asp Gly
 1               5                  10                  15

Ser Val Gln Ser Gly Phe Leu Thr Glu Val His Leu Asp Gly Gln Pro
                 20                  25                  30

Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Leu Glu Trp Thr
             115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 34
<211> LENGTH: 182
```

<212> TYPE: PRT
<213> ORGANISM: Artificial Sequence
<220> FEATURE:
<223> OTHER INFORMATION: Synthetic peptide DSM42 alpha1-alpha2

<400> SEQUENCE: 34

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val
            180
```

<210> SEQ ID NO 35
<211> LENGTH: 182
<212> TYPE: PRT
<213> ORGANISM: Artificial Sequence
<220> FEATURE:
<223> OTHER INFORMATION: Synthetic peptide DSM48 alpha1-alpha2

<400> SEQUENCE: 35

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140
```

Phe Leu Lys Glu Asp Ala Met Ala Thr Asp Thr His Tyr Ile Ala Met
145                 150                 155                 160

Arg Ala Asp Cys Leu Ala Glu Leu Arg Arg Tyr Leu Lys Ser Gly Val
            165                 170                 175

Val Leu Arg Arg Thr Val
            180

<210> SEQ ID NO 36
<211> LENGTH: 182
<212> TYPE: PRT
<213> ORGANISM: Artificial Sequence
<220> FEATURE:
<223> OTHER INFORMATION: Synthetic peptide DSM49 alpha1-alpha2

<400> SEQUENCE: 36

Glu Pro His Ser Leu Arg Tyr Asn Leu Thr Val Leu Ser Trp Asp Gly
1               5                   10                  15

Ser Val Gln Thr Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gln Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Phe Thr Asp Thr His Tyr Arg Ala Met
145                 150                 155                 160

Thr Ala Asp Cys Leu Thr Glu Leu Arg Arg Tyr Leu Lys Ser Gly Val
            165                 170                 175

Val Leu Arg Arg Thr Val
            180

<210> SEQ ID NO 37
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 37
atctataatg ctgagcccca cagtcttcg                                29

<210> SEQ ID NO 38
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 38
cttgctcttc agatatcgcc gtagttc                                  27

<210> SEQ ID NO 39
<211> LENGTH: 7556
<212> TYPE: DNA
<213> ORGANISM: Artificial Sequence
<220> FEATURE:
<223> OTHER INFORMATION: Synthetic DNA construct expressing wt a1a2
domain-Fv

<400> SEQUENCE: 39

```
ggagagacca cacccaagct gtctagagcc gccacgatgg ggctgggccc ggtcttcctg     60
cttctggctg gcatcttccc ttttgcacct ccgggagctg ctgctgagcc ccacagtctt    120
cgttataacc tcacggtgct gtcctgggat ggatctgtgc agtcagggtt tctcactgag    180
gtacatctgg atggtcagcc cttcctgcgc tgtgacaggc agaaatgcag ggcaaagccc    240
cagggacagt gggcagaaga tgtcctggga aataagacat gggacagaga gaccagagac    300
ttgacaggga atggaaagga cctcaggatg accctggctc atatcaagga ccagaaagaa    360
ggcttgcatt ccctccagga gattagggtc tgtgagatcc atgaagacaa cagcaccagg    420
agctcccagc atttctacta cgatggggag ctctttctct cccaaaacct ggagactaag    480
gaatggacaa tgccccagtc ctccagagct cagaccttgg ccatgaacgt caggaatttc    540
ttgaaggaag atgcaatgaa gaccaagaca cactatcacg ctatgcatgc agactgcctg    600
caggaactac ggcgatatct aaaatccggc gtagtcctga ggagaacagt gccccccatg    660
gtgcaggtga ctcgctctga ggcctctggc ggatctgggg accgtgtgac aatcacctgc    720
agagcctccc aggacgtctc cactgccgtg gcgtggtacc aacagaagcc cgggaaggca    780
cccaaactgc tcatttacag cgcatccttt ctctactctg gcgtgccgtc tcgctttagc    840
gggtccggca gcggtacaga ctttactctg accatctcct ctctgcaacc ggaggatttt    900
gcaacctatt attgccagca atcctacaca acccccccca cctttggcca gggcaccaag    960
gtggagatca agggaggttc tagccgctcc agcagctctg gaggtggagg ctctggcgga   1020
ggaggcgagg tgcaactggt ggagtctggg ggcggcctgg tccagcccgg cggaagcttg   1080
cgcctgagct gtgccgcctc cggttttacc ttcaccagca ctggaatctc ctgggtgcgc   1140
caagctcccg gcaaagggct cgaatgggtg ggccgtatct accccaccaa cggaagcacc   1200
aactatgcag acagcgtgaa ggggcgcttc actatctccg ccgacaccag caaaaacacc   1260
gcgtacctgc agatgaattc tttgagggca gaggatactg ccgtgtacta ctgcgcgagg   1320
acatacggca tttacgatct gtatgtggat tacaccgaat acgtgatgga ctattggggc   1380
cagggcactc tggtcacagt gtctagcggt ggcagctccc gcagctccag cagcggtggt   1440
ggcggtagcg gaggcggagg cgatatccag atgactcaga gtccctcttc tctgagtgct   1500
tctggcggaa gtgggcagat caccgtcaca tgtcgcgcaa gcggctttta tccttggaac   1560
atcaccctga gctggcggca ggacggcgtc agcctgtccc atgataccca acagtgggga   1620
gatgtgctcc cggacggtca gggaacttac cagacctggg ttgcaactcg catctcccag   1680
ggggaggagc agcgtttcac atgttatatg gagcactctg gccagcacag cactcatccg   1740
gtgccgtccg gaaagggatc tcatcaccat caccaccact aggatccgtt gaggtctcta   1800
aaagcgtctt cctgttctca tcacatcata tcaaggttat ataccatcaa tattgccaca   1860
gatgttactt agccttttaa tatttctcta atttagtgta tatgcaatga tagttctctg   1920
atttctgaga ttgagtttct catgtgtaat gattatttag agtttctctt tcatctgttc   1980
aaatttttgt ctagttttat tttttactga tttgtaagac ttctttttat aatctgcata   2040
```

```
ttacaattct ctttactggg gtgttgcaaa tattttctgt cattctatgg cctgactttt    2100
cttaatggtt ttttaatttt aaaaataagt cttaatattc atgcaatcta attaacaatc    2160
ttttctttgt ggttaggact ttgagtcata agaaattttt ctctacactg aagtcatgat    2220
ggcatgcttc tatattattt tctaaaagat ttaaagtttt gccttctcca tttagactta    2280
taattcactg gaattttttt gtgtgtatgg tatgacatat gggttccctt ttatttttta    2340
catataaata tattccctg tttttctaaa aagaaaaag atcatcattt tcccattgta      2400
aaatgccata ttttttcat aggtcactta catatatcaa tgggtctgtt tctgagctct     2460
actctatttt atcagcctca ctgtctatcc ccacacatct catgctttgc tctaaatctt    2520
gatatttagt ggaacattct ttcccatttt gttctacaag aatattttg ttattgtctt     2580 tgggctttct atatacattt tgaaatgagg ttgacaagtt aataatcaac ctctggatta    2640
caaaatttgt gaaagattga ctggtattct taactatgtt gctccttta cgctatgtgg     2700 atacgctgct ttaatgcctt tgtatcatgc tattgcttcc cgtatggctt tcattttctc    2760
ctccttgtat aaatcctggt tgctgtctct ttatgaggag ttgtggcccg ttgtcaggca    2820
acgtggcgtg tgtgcactg tgtttgctga cgcaacccc actggttggg gcattgccac      2880
cacctgtcag ctcctttccg ggactttcgc tttcccctc cctattgcca cggcggaact     2940
catcgccgcc tgccttgccc gctgctggac aggggctcgg ctgttgggca ctgacaattc    3000
cgtggtgttg tcggggaaat catcgtcctt tccttggctg ctcgcctgtg ttgccacctg    3060
gattctgcgc gggacgtcct tctgctacgt cccttcggcc ctcaatccag cggaccttcc    3120
ttcccgcggc ctgctgccgg ctctgcggcc tcttccgcct cttcgccttc gccctcagac    3180
gagtcggatc tccctttggg ccgcctcccc gcatctgtgc cttctagttg ccagccatct    3240
gttgtttgcc cctccccgt gccttccttg accctggaag gtgccactcc cactgtcctt     3300
tcctaataaa atgaggaaat tgcatcgcat tgtctgagta ggtgtcattc tattctgggg    3360
ggtggggtgg ggcaggacag caaggggag gattggcaag acaatagcag gctttgcatt     3420
tttagacatt tagaagccta tatcttgtta cagaattgga attacacaaa aattctacca    3480
tattttgaaa gcttaggttg ttctgaaaaa acaatatat tgttttcctg ggtaaactaa     3540 aagtccctc gaggaaaggc ccctaaagtg aaacagtgca aaacgttcaa aaactgtctg     3600
gcaatacaag ttccactttg accaaaacgg ctggcagtaa aagggttaag aagactgtca    3660
gccttgagcg gtatcagctc actcaaaggc ggtaatacgg ttatccacag aatcagggga    3720
taacgcagga agaacatgt gagcaaaagg ccagcaaaag gccaggaacc gtaaaaaggc     3780
cgcgttgctg gcgttttcc ataggctccg ccccctgac gagcatcaca aaatcgacg       3840 ctcaagtcag aggtggcgaa acccgacagg actataaaga taccaggcgt ttccccctgg    3900
aagctccctc gtgcgctctc ctgttccgac cctgccgctt accggatacc tgtccgcctt    3960
tctcccttcg ggaagcgtgg cgctttctca tagctcacgc tgtaggtatc tcagttcggt    4020
gtaggtcgtt cgctccaagc tgggctgtgt gcacgaaccc ccgttcagc ccgaccgctg     4080 cgccttatcc ggtaactatc gtcttgagtc caacccggta agacacgact tatcgccact    4140
ggcagcagcc actggtaaca ggattagcag agcgaggtat gtaggcggtg ctacagagtt    4200
cttgaagtgg tgggctaact acggctacac tagaagaaca gtatttggta tctgcgctct    4260
gctgaagcca gttaccttcg gaaaaagagt tggtagctct tgatccggca aacaaaccac    4320
cgctggtagc ggtggttttt ttgtttgcaa gcagcagatt acgcgcagaa aaaaaggatc    4380
```

-continued

```
tcaagaagat cctttgatct tttctacggg gtctgacgct cagtggaacg acgcgcgcgt    4440
aactcacgtt aagggatttt ggtcatgagt tagaaaaact catcgagcat caaatgaaac    4500
tgcaatttat tcatatcagg attatcaata ccatatttt  gaaaaagccg tttctgtaat    4560
gaaggagaaa actcaccgag gcagttccat aggatggcaa gatcctggta tcggtctgcg    4620
attccgactc gtccaacatc aatacaacct attaatttcc cctcgtcaaa ataaggtta    4680 tcaagtgaga atcaccatg  agtgacgact gaatccggtg agaatggcaa agtttatgc    4740 atttctttcc agacttgttc aacaggccag ccattacgct cgtcatcaaa atcactcgca    4800
tcaaccaaac cgttattcat tcgtgattgc gcctgagcga ggcgaaatac gcgatcgctg    4860
ttaaaaggac aattacaaac aggaatcgag tgcaaccggc gcaggaacac tgccagcgca    4920
tcaacaatat tttcacctga atcaggatat tcttctaata cctggaacgc tgttttccg    4980 gggatcgcag tggtgagtaa ccatgcatca tcaggagtac ggataaaatg cttgatggtc    5040
ggaagtggca taaattccgt cagccagttt agtctgacca tctcatctgt aacatcattg    5100 gcaacgtac  ctttgccatg tttcagaaac aactctggcg catcgggctt cccatacaag    5160
cgatagattg tcgcacctga ttgcccgaca ttatcgcgag cccatttata cccatataaa    5220
tcagcatcca tgttggaatt taatcgcggc ctcgacgttt ccgttggat  atggctcatt    5280 ttttacttcc tcaccttgtc gtattatact atgccgatat actatgccga tgattaattg    5340
tcgacactgc gggggctctg tgtggtaagc aggtcttaac cttttactg  ccaatgacgc    5400 atgggatacg tcgtggcagt aaaagggctt aaatgccaac gacgcgtccc atacgttgtt    5460
ggcattttaa ttcttctctc tgcagcggca gcatgtgccg ccgctgcaga gagtttctag    5520
cgatgacagc ccctctgggc aacgagccgg ggggctgtc  tttctttatg ttttaaatgc    5580
actgacctcc cacattccct ttttagtaaa atattcagaa ataatttaaa tacatcattg    5640
caatgaaaat aaatgttttt tattaggcag aatccagatg ctcaaggccc ttcataatat    5700
cccccagttt agtagttgga cttagggaac aaaggaacct ttaatagaaa ttggacagca    5760
agaaagcgag tcaggcaccg ggcttgcggg tcatgcacca ggtgcgcggt ccttcgggca    5820
cctcgacgtc ggcggtgacg gtgaagccga gccgctcgta aaggggagg  ttgcggggcg    5880 cggatgtctc caggaaggcg ggcaccccgg cgcgctcggc cgcctccact ccggggagca    5940
cgacggcgct gccagaccc  ttgccctggt ggtcggcga  cacgccgacg gtggccagga    6000
accacgcggg ctccttgggc cggtgcggcg ccaggaggcc ttccatctgt tgctgcgcgg    6060
ccagccggga accgctcaac tcggccatgc gcgggccgat ctcggcgaac accgccccg    6120 cttcgacgct ctccggcgtg gtccagaccg ccaccgcggc gccgtcgtcc gcgacccaca    6180
ccttgccgat gtcgagcccg acgcgcgtga ggaagagttc ttgcagctcg gtgacccgct    6240
cgatgtggcg gtccggatcg acggtgtggc gcgtggcggg gtagtcggcg aacgcggcgg    6300
cgagggtgcg tacggccctg gggacgtcgt cgcgggtggc gaggcgcacc gtgggcttgt    6360
actcggtcat ggtggcggac gaaaggcccg gagatgagga agaggagaac agcgcggcag    6420
acgtgcgctt ttgaagcgtg cagaatgccg ggcctccgga ggaccttcgg gcgccgccc    6480 cgccctgag  cccgccctg  agccgccc   cggaccacc  ccttcccagc ctctgagccc    6540
agaaagcgaa ggagcaaagc tgctattggc cgctgcccca aaggcctacc cgcttccatt    6600
gctcagcggt gctgtccatc tgcacgagac tagtgagtcg tgctacttcc atttgtcacg    6660
tcctgcacga cgcgagctgc ggggcggggg ggaacttcct gactagggga ggagtagaag    6720
gtggcgcgaa ggggccacca aagaacggag ccggttggcg cctaccggtg gatgtggaat    6780
```

```
gtgtgcgagg ccagaggcca cttgtgtagc gccaagtgcc cagcggggct gctaaagcgc    6840
atgctccaga ctgccttggg aaaagcgcct ccctacccg gtagagaaac ttgatctgtc     6900
gccgcaattc aaacttcgtg aggctccggt gcccgtcagt gacctgctat actctggaga    6960
cgacttacgg taaatggccc gcctggctga ccgcccaacg accccgccc attgacgtca     7020 ataatgacgt atgttcccat agtaacgcca atagggactt tccattgacg tcaatgggtg    7080
gagtatttac ggtaaactgc ccacttggca gtacatcaag tgtatcatat gccaagtccg    7140 cccctattg acgtcaatga cggtaaatgg cccgcctggc attatgccca gtacatgacc     7200
ttacgggact ttcctacttg gcagtacatc tacgtattag tcatcgctat taccatgctg    7260
atgcggtttt ggcagtacac caatgggcgt ggatagcggt ttgactcacg ggatttcca     7320 agtctccacc ccattgacgt caatgggagt ttgttttggc accaaaatca acgggacttt    7380
ccaaaatgtc gtaataaccc cgccccgttg acgcaaatgg gcggtaggcg tgtacggtgg    7440
gaggtctata taagcagagc tcgtttagtg aaccgtcaga tcgcctggag aggccatcca    7500
cgctgttttg acctccatag tggacaccgg gaccgatcca gcctccgcgt ctcagg        7556
```

<210> SEQ ID NO 40
<211> LENGTH: 558
<212> TYPE: PRT
<213> ORGANISM: Artificial Sequence
<220> FEATURE:
<223> OTHER INFORMATION: Synthetic peptide wt MICA-Fv

<400> SEQUENCE: 40

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220
```

```
Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
            245                 250                 255

Ile Ser Ser Leu Gln Pro Glu Asp Phe Ala Thr Tyr Tyr Cys Gln Gln
        260                 265                 270

Ser Tyr Thr Thr Pro Pro Thr Phe Gly Gln Gly Thr Lys Val Glu Ile
    275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
        340                 345                 350

Glu Trp Val Gly Arg Ile Tyr Pro Thr Asn Gly Ser Thr Asn Tyr Ala
    355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
        500                 505                 510

Gly Thr Tyr Gln Thr Trp Val Ala Thr Arg Ile Ser Gln Gly Glu Glu
    515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555
```

<210> SEQ ID NO 41
<211> LENGTH: 558
<212> TYPE: PRT
<213> ORGANISM: Artificial Sequence
<220> FEATURE:
<223> OTHER INFORMATION: Synthetic peptide MICwed-Fv

<400> SEQUENCE: 41

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30
```

-continued

Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Ser Gly Gly Gly Gly Ser Gly
    290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Ser Gly Gly Gly Gly Ser
        435                 440                 445

Gly Gly Gly Gly Asp Ile Gln Met Thr Gln Ser Pro Ser Ser Leu Ser

```
                    450                 455                 460
Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 42
<211> LENGTH: 558
<212> TYPE: PRT
<213> ORGANISM: Artificial Sequence
<220> FEATURE:
<223> OTHER INFORMATION: Synthetic peptide MICv20-Fv

<400> SEQUENCE: 42

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Ala Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Gln Thr Asp Thr His Tyr Arg Ala Met
145                 150                 155                 160

His Ala Asp Cys Leu Phe Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
```

```
            260                 265                 270
Ser Tyr Thr Thr Pro Pro Thr Phe Gly Gln Gly Thr Lys Val Glu Ile
            275                 280                 285

Lys Gly Gly Ser Ser Arg Ser Ser Ser Gly Gly Gly Ser Gly
        290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Ser
            435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His
545                 550                 555

<210> SEQ ID NO 43
<211> LENGTH: 558
<212> TYPE: PRT
<213> ORGANISM: Artificial Sequence
<220> FEATURE:
<223> OTHER INFORMATION: Synthetic peptide MICv25-Fv

<400> SEQUENCE: 43

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
```

-continued

```
                65                  70                  75                  80
Lys Asp Gln Lys Glu Gly Leu His Ser Leu Gln Glu Ile Arg Val Cys
                    85                  90                  95
Glu Ile His Glu Asp Asn Ser Thr Arg Ser Ser Gln His Phe Tyr Tyr
                    100                 105                 110
Asp Gly Glu Leu Phe Leu Ser Gln Asn Leu Glu Thr Leu Glu Trp Thr
                    115                 120                 125
Met Pro Gln Ser Ser Arg Ala Gln Thr Leu Ala Met Asn Val Arg Asn
                    130                 135                 140
Phe Leu Lys Glu Asp Ala Met Glu Thr Asp Thr His Tyr His Ala Met
145                 150                 155                 160
Arg Ala Asp Cys Leu Ser Glu Leu Arg Arg Tyr Leu Lys Ser Gly Val
                    165                 170                 175
Val Leu Arg Arg Thr Val Pro Pro Met Val Gln Val Thr Arg Ser Glu
                    180                 185                 190
Ala Ser Gly Gly Ser Gly Asp Arg Val Thr Ile Thr Cys Arg Ala Ser
                    195                 200                 205
Gln Asp Val Ser Thr Ala Val Ala Trp Tyr Gln Gln Lys Pro Gly Lys
                    210                 215                 220
Ala Pro Lys Leu Leu Ile Tyr Ser Ala Ser Phe Leu Tyr Ser Gly Val
225                 230                 235                 240
Pro Ser Arg Phe Ser Gly Ser Gly Ser Gly Thr Asp Phe Thr Leu Thr
                    245                 250                 255
Ile Ser Ser Leu Gln Pro Glu Asp Phe Ala Thr Tyr Tyr Cys Gln Gln
                    260                 265                 270
Ser Tyr Thr Thr Pro Pro Thr Phe Gly Gln Gly Thr Lys Val Glu Ile
                    275                 280                 285
Lys Gly Gly Ser Ser Arg Ser Ser Ser Ser Gly Gly Gly Gly Ser Gly
                    290                 295                 300
Gly Gly Gly Glu Val Gln Leu Val Glu Ser Gly Gly Gly Leu Val Gln
305                 310                 315                 320
Pro Gly Gly Ser Leu Arg Leu Ser Cys Ala Ala Ser Gly Phe Thr Phe
                    325                 330                 335
Thr Ser Thr Gly Ile Ser Trp Val Arg Gln Ala Pro Gly Lys Gly Leu
                    340                 345                 350
Glu Trp Val Gly Arg Ile Tyr Pro Thr Asn Gly Ser Thr Asn Tyr Ala
                    355                 360                 365
Asp Ser Val Lys Gly Arg Phe Thr Ile Ser Ala Asp Thr Ser Lys Asn
                    370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                    405                 410                 415
Thr Glu Tyr Val Met Asp Tyr Trp Gly Gln Gly Thr Leu Val Thr Val
                    420                 425                 430
Ser Ser Gly Gly Ser Ser Arg Ser Ser Ser Ser Gly Gly Gly Gly Ser
                    435                 440                 445
Gly Gly Gly Gly Asp Ile Gln Met Thr Gln Ser Pro Ser Ser Leu Ser
450                 455                 460
Ala Ser Gly Gly Ser Gly Gln Ile Thr Val Thr Cys Arg Ala Ser Gly
465                 470                 475                 480
Phe Tyr Pro Trp Asn Ile Thr Leu Ser Trp Arg Gln Asp Gly Val Ser
                    485                 490                 495
```

```
Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His His
545                 550                 555

<210> SEQ ID NO 44
<211> LENGTH: 558
<212> TYPE: PRT
<213> ORGANISM: Artificial Sequence
<220> FEATURE:
<223> OTHER INFORMATION: Synthetic peptide MICv27-Fv

<400> SEQUENCE: 44

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Ser Gly
    290                 295                 300
```

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
        340                 345                 350

Glu Trp Val Gly Arg Ile Tyr Pro Thr Asn Gly Ser Thr Asn Tyr Ala
    355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
        500                 505                 510

Gly Thr Tyr Gln Thr Trp Val Ala Thr Arg Ile Ser Gln Gly Glu Glu
    515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 45
<211> LENGTH: 558
<212> TYPE: PRT
<213> ORGANISM: Artificial Sequence
<220> FEATURE:
<223> OTHER INFORMATION: Synthetic peptide MICv28-Fv

<400> SEQUENCE: 45

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

```
Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
            195                 200                 205

Gln Asp Val Ser Thr Ala Val Ala Trp Tyr Gln Gln Lys Pro Gly Lys
        210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
        290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gln Gly Thr Leu Val Thr Val
            420                 425                 430

Ser Ser Gly Gly Ser Ser Arg Ser Ser Ser Gly Gly Gly Gly Ser
            435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
            515                 520                 525
```

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 46
<211> LENGTH: 558
<212> TYPE: PRT
<213> ORGANISM: Artificial Sequence
<220> FEATURE:
<223> OTHER INFORMATION: Synthetic peptide MICv42-Fv

<400> SEQUENCE: 46

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
        50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
                325                 330                 335

```
Thr Ser Thr Gly Ile Ser Trp Val Arg Gln Ala Pro Gly Lys Gly Leu
                340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
        450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555
```

<210> SEQ ID NO 47
<211> LENGTH: 558
<212> TYPE: PRT
<213> ORGANISM: Artificial Sequence
<220> FEATURE:
<223> OTHER INFORMATION: Synthetic peptide MICv48-Fc

<400> SEQUENCE: 47

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
    130                 135                 140
```

```
Phe Leu Lys Glu Asp Ala Met Ala Thr Asp Thr His Tyr Ile Ala Met
145                 150                 155                 160

Arg Ala Asp Cys Leu Ala Glu Leu Arg Arg Tyr Leu Lys Ser Gly Val
            165                 170                 175

Val Leu Arg Arg Thr Val Pro Pro Met Val Gln Val Thr Arg Ser Glu
        180                 185                 190

Ala Ser Gly Gly Ser Gly Asp Arg Val Thr Ile Thr Cys Arg Ala Ser
    195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
            245                 250                 255

Ile Ser Ser Leu Gln Pro Glu Asp Phe Ala Thr Tyr Tyr Cys Gln Gln
        260                 265                 270

Ser Tyr Thr Thr Pro Pro Thr Phe Gly Gln Gly Thr Lys Val Glu Ile
    275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
        340                 345                 350

Glu Trp Val Gly Arg Ile Tyr Pro Thr Asn Gly Ser Thr Asn Tyr Ala
    355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
        500                 505                 510

Gly Thr Tyr Gln Thr Trp Val Ala Thr Arg Ile Ser Gln Gly Glu Glu
    515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555
```

<210> SEQ ID NO 48
<211> LENGTH: 558
<212> TYPE: PRT
<213> ORGANISM: Artificial Sequence
<220> FEATURE:
<223> OTHER INFORMATION: Synthetic peptide MICv49-Fv

<400> SEQUENCE: 48

```
Glu Pro His Ser Leu Arg Tyr Asn Leu Thr Val Leu Ser Trp Asp Gly
1               5                   10                  15

Ser Val Gln Thr Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gln Trp Gly Lys Asp Leu Arg Met Thr Leu Ala His Ile
65                  70                  75                  80

Lys Asp Gln L

```
                370               375               380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
                420                 425                 430

Ser Ser Gly Gly Ser Ser Arg Ser Ser Ser Gly Gly Gly Ser
                435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
                515                 520                 525

Gln Arg Phe Thr Cys Tyr Met Glu His Ser Gly Gln His Ser Thr His
530                 535                 540

Pro Val Pro Ser Gly Lys Gly Ser His His His His His His
545                 550                 555
```

<210> SEQ ID NO 49
<211> LENGTH: 137
<212> TYPE: PRT
<213> ORGANISM: Artificial Sequence
<220> FEATURE:
<223> OTHER INFORMATION: Synthetic NKG2D ectodomain

<400> SEQUENCE: 49

```
Asn Ser Leu Phe Asn Gln Glu Val Gln Ile Pro Leu Thr Glu Ser Tyr
1               5                   10                  15

Cys Gly Pro Cys Pro Lys Asn Trp Ile Cys Tyr Lys Asn Asn Cys Tyr
                20                  25                  30

Gln Phe Phe Asp Glu Ser Lys Asn Trp Tyr Glu Ser Gln Ala Ser Cys
            35                  40                  45

Met Ser Gln Asn Ala Ser Leu Leu Lys Val Tyr Ser Lys Glu Asp Gln
50                  55                  60

Asp Leu Leu Lys Leu Val Lys Ser Tyr His Trp Met Gly Leu Val His
65                  70                  75                  80

Ile Pro Thr Asn Gly Ser Trp Gln Trp Glu Asp Gly Ser Ile Leu Ser
                85                  90                  95

Pro Asn Leu Leu Thr Ile Ile Glu Met Gln Lys Gly Asp Cys Ala Leu
                100                 105                 110

Tyr Ala Ser Ser Phe Lys Gly Tyr Ile Glu Asn Cys Ser Thr Pro Asn
            115                 120                 125

Thr Tyr Ile Cys Met Gln Arg Thr Val
        130                 135
```

<210> SEQ ID NO 50
<211> LENGTH: 40
<212> TYPE: DNA
<213> ORGANISM: Artificial Sequence
<220> FEATURE:
<223> OTHER INFORMATION: Synthetic oligonucleotide

```
<400> SEQUENCE: 50
ctgtctagag ccgccaacat ggggctgggc ccggtcttcc                          40

<210> SEQ ID NO 51
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 51
aacggatcct acacagtcct ttgcatgcag                                     30

<210> SEQ ID NO 52
<211> LENGTH: 6362
<212> TYPE: DNA
<213> ORGANISM: Artificial Sequence
<220> FEATURE:
<223> OTHER INFORMATION: Synthetic polynucleotide, pD2509-CMV-Avi-His-
      natural NKG2D ectodomain

<400> SEQUENCE: 52
ggagagacca cacccaagct gtctagagcc gccaacatgg ggctgggccc ggtcttcctg    60
cttctggctg gcatcttccc ttttgcacct ccgggagctg ctgctgagcc ccaccatcat   120
caccaccatg gccttaacga catcttcgaa gctcaaaaga tcgaatggca tgaaaactca   180
ttattcaacc aagaagttca aattcccttg accgaaagtt actgtggccc atgtcctaaa   240
aactggatat gttacaaaaa taactgctac caatttttg atgagagtaa aaactggtat    300
gagagccagg cttcttgtat gtctcaaaat gccagccttc tgaaagtata cagcaaagag   360
gaccaggatt tacttaaact ggtgaagtca tatcattgga tgggactagt acacattcca   420
acaaatggat cttggcagtg gaagatggc tccattctct cacccaacct actaacaata    480
attgaaatgc agaagggaga ctgtgcactc tatgcctcga gctttaaagg ctatatagaa   540
aactgttcaa ctccaaatac atacatctgc atgcaaagga ctgtgtagga tccgttgagg   600
tctctaaaag cgtcttcctg ttctcatcac atcatatcaa ggttatatac catcaatatt   660
gccacagatg ttacttagcc ttttaatatt tctctaattt agtgtatatg caatgatagt   720
tctctgattt ctgagattga gtttctcatg tgtaatgatt atttagagtt tctctttcat   780
ctgttcaaat ttttgtctag ttttattttt tactgatttg taagacttct ttttataatc   840
tgcatattac aattctcttt actggggtgt gcaaatatt ttctgtcatt ctatggcctg    900
acttttctta atggtttttt aattttaaaa ataagtctta atattcatgc aatctaatta   960
acaatctttt ctttgtggtt aggactttga gtcataagaa attttctct acactgaagt   1020 catgatggca tgcttctata ttattttcta aaagatttaa agttttgcct tctccattta   1080
gacttataat tcactggaat ttttttgtgt gtatggtatg acatatgggt tccctttat    1140 tttttacata taaatatatt tccctgtttt tctaaaaaag aaaagatca tcattttccc    1200 attgtaaaat gccatatttt tttcataggt cacttacata tatcaatggg tctgtttctg   1260
agctctactc tattttatca gcctcactgt ctatccccac acatctcatg ctttgctcta   1320
aatcttgata tttagtggaa cattctttcc cattttgttc tacaagaata ttttttgttat 1380 tgtctttggg cttctatat acattttgaa atgaggttga caagttaata atcaacctct    1440
ggattacaaa atttgtgaaa gattgactgg tattcttaac tatgttgctc cttttacgct   1500
atgtggatac gctgctttaa tgcctttgta tcatgctatt gcttccgta tggctttcat    1560
```

```
tttctcctcc ttgtataaat cctggttgct gtctctttat gaggagttgt ggcccgttgt    1620
caggcaacgt ggcgtggtgt gcactgtgtt tgctgacgca accccccactg gttggggcat    1680 tgccaccacc tgtcagctcc tttccgggac tttcgctttc cccctcccta ttgccacggc    1740
ggaactcatc gccgcctgcc ttgcccgctg ctggacaggg gctcggctgt gggcactga    1800 caattccgtg gtgttgtcgg ggaaatcatc gtcctttcct ggctgctcg cctgtgttgc    1860 cacctggatt ctgcgcggga cgtccttctg ctacgtccct tcggccctca atccagcgga    1920
ccttccttcc cgcggcctgc tgccggctct gcggcctctt ccgcctcttc gccttcgccc    1980
tcagacgagt cggatctccc tttgggccgc ctccccgcat ctgtgccttc tagttgccag    2040
ccatctgttg tttgcccctc ccccgtgcct tccttgaccc tggaaggtgc cactcccact    2100
gtcctttcct aataaaatga ggaaattgca tcgcattgtc tgagtaggtg tcattctatt    2160 ctgggggtg gggtggggca ggacagcaag ggggaggatt ggcaagacaa tagcaggctt    2220
tgcattttta gacatttaga agcctatatc ttgttacaga attggaatta cacaaaaatt    2280
ctaccatatt ttgaaagctt aggttgttct gaaaaaaaca atatattgtt ttcctgggta    2340
aactaaaagt cccctcgagg aaaggcccct aaagtgaaac agtgcaaaac gttcaaaaac    2400
tgtctggcaa tacaagttcc actttgacca aaacggctgg cagtaaaagg gttaagaaga    2460
ctgtcagcct tgagcggtat cagctcactc aaaggcggta atacggttat ccacagaatc    2520
aggggataac gcaggaaaga acatgtgagc aaaaggccag caaaaggcca ggaaccgtaa    2580
aaaggccgcg ttgctggcgt ttttccatag gctccgcccc cctgacgagc atcacaaaaa    2640
tcgacgctca agtcagaggt ggcgaaaccc gacaggacta taaagatacc aggcgtttcc    2700
ccctggaagc tccctcgtgc gctctcctgt tccgaccctg ccgcttaccg gatacctgtc    2760
cgcctttctc ccttcgggaa gcgtggcgct ttctcatagc tcacgctgta ggtatctcag    2820
ttcggtgtag gtcgttcgct ccaagctggg ctgtgtgcac gaaccccccg ttcagcccga    2880
ccgctgcgcc ttatccggta actatcgtct tgagtccaac ccggtaagac acgacttatc    2940
gccactggca gcagccactg gtaacaggat tagcagagcg aggtatgtag gcggtgctac    3000
agagttcttg aagtggtggg ctaactacgg ctacactaga agaacagtat ttggtatctg    3060
cgctctgctg aagccagtta ccttcggaaa aagagttggt agctcttgat ccggcaaaca    3120
aaccaccgct ggtagcggtg gtttttttgt ttgcaagcag cagattacgc gcagaaaaaa    3180
aggatctcaa gaagatcctt tgatcttttc tacggggtct gacgctcagt ggaacgacgc    3240
gcgcgtaact cacgttaagg gattttggtc atgagttaga aaaactcatc gagcatcaaa    3300
tgaaactgca atttattcat atcaggatta tcaataccat attttttgaaa agccgtttc    3360 tgtaatgaag gagaaaactc accgaggcag ttccatagga tggcaagatc ctggtatcgg    3420
tctgcgattc cgactcgtcc aacatcaata caacctatta atttcccctc gtcaaaaata    3480
aggttatcaa gtgagaaatc accatgagtg acgactgaat ccggtgagaa tggcaaaagt    3540
ttatgcattt cttttccagac ttgttcaaca ggccagccat tacgctcgtc atcaaaatca    3600
ctcgcatcaa ccaaaccgtt attcattcgt gattgcgcct gagcgaggcg aaatacgcga    3660
tcgctgttaa aaggacaatt acaaacagga atcgagtgca accggcgcag gaacactgcc    3720
agcgcatcaa caatatttc acctgaatca ggatattctt ctaatacctg gaacgctgtt    3780
tttccgggga tcgcagtggt gagtaaccat gcatcatcag gagtacggat aaaatgcttg    3840
atggtcggaa gtggcataaa ttccgtcagc cagtttagtc tgaccatctc atctgtaaca    3900
```

```
tcattggcaa cgctaccttt gccatgtttc agaaacaact ctggcgcatc gggcttccca    3960
tacaagcgat agattgtcgc acctgattgc ccgacattat cgcgagccca tttataccca    4020
tataaatcag catccatgtt ggaatttaat cgcggcctcg acgtttcccg ttggatatgg    4080 ctcattttt acttcctcac cttgtcgtat tatactatgc cgatatacta tgccgatgat    4140
taattgtcga cactgcgggg gctctgtgtg gtaagcaggt cttaaccttt ttactgccaa    4200
tgacgcatgg gatacgtcgt ggcagtaaaa gggcttaaat gccaacgacg cgtcccatac    4260
gttgttggca ttttaattct tctctctgca gcggcagcat gtgccgccgc tgcagagagt    4320
ttctagcgat gacagcccct ctgggcaacg agccggggg gctgtctttc tttatgtttt    4380
aaatgcactg acctcccaca ttcccttttt agtaaaatat tcagaaataa tttaaataca    4440
tcattgcaat gaaaataaat gtttttatt aggcagaatc cagatgctca aggcccttca    4500
taatatcccc cagtttagta gttggactta gggaacaaag gaaccttaa tagaaattgg    4560 acagcaagaa agcgagtcag gcaccgggct tgcgggtcat gcaccaggtg cgcggtcctt    4620
cgggcacctc gacgtcggcg gtgacggtga agccgagccg ctcgtagaag gggaggttgc    4680
ggggcgcgga tgtctccagg aaggcgggca ccccggcgcg ctcggccgcc tccactccgg    4740
ggagcacgac ggcgctgccc agaccccttgc cctggtggtc gggcgacacg ccgacggtgg    4800
ccaggaacca cgcgggctcc ttgggccggt gcggcgccag gaggccttcc atctgttgct    4860
gcgcggccag ccgggaaccg ctcaactcgg ccatgcgcgg gccgatctcg gcgaacaccg    4920 ccccgcttc gacgctctcc ggcgtggtcc agaccgccac cgcggcgccg tcgtccgcga    4980
cccacacctt gccgatgtcg agcccgacgc gcgtgaggaa gagttcttgc agctcggtga    5040
cccgctcgat gtggcggtcc ggatcgacgg tgtggcgcgt ggcggggtag tcggcgaacg    5100
cggcggcgag ggtgcgtacg gccctgggga cgtcgtcgcg ggtggcgagg cgcaccgtgg    5160
gcttgtactc ggtcatggtg gcggacgaaa ggcccggaga tgaggaagag gagaacagcg    5220
cggcagacgt gcgcttttga agcgtgcaga atgccgggcc tccggaggac cttcgggcgc    5280
ccgccccgcc cctgagcccg ccctgagcc cgccccgga cccaccct cccagcctct    5340 gagcccagaa agcgaaggag caaagctgct attggccgct gccccaaagg cctacccgct    5400
tccattgctc agcggtgctg tccatctgca cgagactagt gagtcgtgct acttccattt    5460
gtcacgtcct gcacgacgcg agctgcgggg cgggggggaa cttcctgact aggggaggag    5520
tagaaggtgg cgcgaagggg ccaccaaaga acggagccgg ttggcgccta ccggtggatg    5580
tggaatgtgt gcgaggccag aggccacttg tgtagcgcca agtgcccagc ggggctgcta    5640
aagcgcatgc tccagactgc cttgggaaaa gcgcctcccc tacccggtag agaaacttga    5700
tctgtcgccg caattcaaac ttcgtgaggc tccggtgccc gtcagtgacc tgctatactc    5760
tggagacgac ttacggtaaa tggcccgcct ggctgaccgc ccaacgaccc ccgcccattg    5820
acgtcaataa tgacgtatgt tcccatagta acgccaatag ggactttcca ttgacgtcaa    5880
tgggtggagt atttacggta aactgcccac ttggcagtac atcaagtgta tcatatgcca    5940
agtccgcccc ctattgacgt caatgacggt aaatggcccg cctggcatta tgcccagtac    6000
atgaccttac gggactttcc tacttggcag tacatctacg tattagtcat cgctattacc    6060
atgctgatgc ggttttggca gtacaccaat gggcgtggat agcggtttga ctcacgggga    6120
tttccaagtc tccaccccat tgacgtcaat gggagtttgt tttggcacca aaatcaacgg    6180
gactttccaa aatgtcgtaa taaccccgcc ccgttgacga aatgggcgg taggcgtgta    6240 cggtgggagg tctatataag cagagctcgt ttagtgaacc gtcagatcgc ctggagaggc    6300
```

```
catccacgct gttttgacct ccatagtgga caccgggacc gatccagcct ccgcgtctca    6360
gg                                                                  6362
```

<210> SEQ ID NO 53
<211> LENGTH: 160
<212> TYPE: PRT
<213> ORGANISM: Artificial Sequence
<220> FEATURE:
<223> OTHER INFORMATION: Synthetic peptide, His-avitag-natural NKG2D
      ectodomain

<400> SEQUENCE: 53

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
        35                  40                  45

Cys Tyr Lys Asn Asn Cys Tyr Gln Phe Phe Asp Glu Ser Lys Asn Trp
    50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Tyr
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met
        115                 120                 125

Gln Lys Gly Asp Cys Ala Leu Tyr Ala Ser Ser Phe Lys Gly Tyr Ile
    130                 135                 140

Glu Asn Cys Ser Thr Pro Asn Thr Tyr Ile Cys Met Gln Arg Thr Val
145                 150                 155                 160

<210> SEQ ID NO 54
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y152A ectodomain

<400> SEQUENCE: 54

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
        35                  40                  45

Cys Tyr Lys Asn Asn Cys Tyr Gln Phe Phe Asp Glu Ser Lys Asn Trp
    50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Ala
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met

```
                115             120             125
Gln Lys Gly Asp Cys Ala Leu Tyr Ala Ser Ser Phe Lys Gly Tyr Ile
            130             135             140

Glu Asn Cys Ser Thr Pro Asn Thr Tyr Ile Cys Met Gln Arg Thr Val
145             150             155             160

<210> SEQ ID NO 55
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y199A ectodomain

<400> SEQUENCE: 55

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
            35                  40                  45

Cys Tyr Lys Asn Asn Cys Tyr Gln Phe Phe Asp Glu Ser Lys Asn Trp
50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Tyr
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met
            115                 120                 125

Gln Lys Gly Asp Cys Ala Leu Tyr Ala Ser Ser Phe Lys Gly Ala Ile
            130             135             140

Glu Asn Cys Ser Thr Pro Asn Thr Tyr Ile Cys Met Gln Arg Thr Val
145             150             155             160

<210> SEQ ID NO 56
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y152A +Y199A ectodomain

<400> SEQUENCE: 56

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
            35                  40                  45

Cys Tyr Lys Asn Asn Cys Tyr Gln Phe Phe Asp Glu Ser Lys Asn Trp
50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Ala
                85                  90                  95

His Trp Met Gly Leu Val His Ile Pro Thr Asn Gly Ser Trp Gln Trp
```

```
                100              105              110
Glu Asp Gly Ser Ile Leu Ser Pro Asn Leu Leu Thr Ile Ile Glu Met
        115              120              125

Gln Lys Gly Asp Cys Ala Leu Tyr Ala Ser Ser Phe Lys Gly Ala Ile
        130              135              140

Glu Asn Cys Ser Thr Pro Asn Thr Tyr Ile Cys Met Gln Arg Thr Val
145              150              155              160

<210> SEQ ID NO 57
<211> LENGTH: 7640
<212> TYPE: DNA
<213> ORGANISM: Artificial Sequence
<220> FEATURE:
<223> OTHER INFORMATION: Synthetic polynucleotide, wt MIC-Fc expression
      vector

<400> SEQUENCE: 57
ggagagacca cacccaagct gtctagagcc gccaacatgg ggctgggccc ggtcttcctg      60
cttctggctg gcatcttccc ttttgcacct ccgggagctg ctgctgagcc ccacagtctt    120
cgttataacc tcacggtgct gtcctgggat ggatctgtgc agtcagggtt tctcactgag    180
gtacatctgg atggtcagcc cttcctgcgc tgtgacagga gaaatgcag gcaaagccc     240 cagggacagt gggcagaaga tgtcctggga ataagacat gggacagaga gaccagagac    300
ttgacagggt ggggaaagga cctcaggatg accctggctc atatcaagga ccagaaagaa   360
ggcttgcatt ccctccagga gattagggtc tgtgagatcc atgaagacaa cagcaccagg   420
agctcccagc atttctacta cgatgggag ctctttctct cccaaaacct ggagactaag    480
gaatggacaa tgccccagtc ctccagagct cagaccttgg ccatgaacgt caggaatttc   540
ttgaaggaag atgcaatgga gaccgataca cactatcacg ctatgcatgc agactgcctg   600
caggaactac ggcgatatct aaaatccggc gtagtcctga ggagaacagt gccccccatg   660
gtgaatgtca cccgcagcga ggcctcgag gcaacatta ccgtgacatg cagggcttct    720
ggcttctatc cctggaatat cacactgagc tggcgtcagg atgggtatc tttgagccac    780 gacacccagc agtgggggga tgtcctgcct gatgggaatg gaacctacca gacctgggtg   840
gccaccagga tttgccaagg agaggagcag aggttcacct gctacatgga acacagcggg   900
aatcacagca ctcaccctgt gccctctggg aaaatcgaag gacgcatgga cccaaagagt   960
tgcgacaaaa ctcacacatg cccaccgtgc ccaggtaagc cagcccaggc ctcgccctcc  1020
agctcaaggc gggacaggtg ccctagagta gcctgcatcc agggacaggc cccagccggg  1080
tgctgacacg tccacctcca tctcttcctc agcacctgaa ctcctggggg gaccgtcagt  1140
cttcctcttc cccccaaaac ccaaggacac cctcatgatc tcccggaccc ctgaggtcac  1200
atgcgtggtg gtggacgtga gccacgaaga ccctgaggtc aagttcaact ggtacgtgga  1260
cggcgtggag gtgcataatg ccaagacaaa gccgcgggag gagcagtaca acagcacgta  1320
ccgtgtggtc agcgtcctca ccgtcctgca ccaggactgg ctgaatggca aggagtacaa  1380
gtgcaaggtc tccaacaaag ccctcccagc ccccatcgag aaaaccatct ccaaagccaa  1440
aggtgggacc cgtggggtgc gagggccaca tggacagagg ccggctcggc ccaccctctg  1500
ccctgagagt gactgctgta ccaacctctg tcctacagg gcagcccga gaaccacagg   1560 tgtacaccct gcccccatcc cgggatgagc tgaccaagaa ccaggtcagc ctgacctgcc  1620
tggtcaaagg cttctatccc agcgacatcg ccgtggagtg ggagagcaat gggcagccgg  1680
agaacaacta caagaccacg cctcccgtgc tggactccga cggctccttc ttcctctaca  1740
```

```
gcaagctcac cgtggacaag agcaggtggc agcaggggaa cgtcttctca tgctccgtga   1800
tgcatgaggc tctgcacaac cactacacgc agaagagcct ctccctgtct ccgggtaaat   1860
gataggatcc ggttgaggtc tctaaaagcg tcttcctgtt ctcatcacat catatcaagg   1920
ttatatacca tcaatattgc cacagatgtt acttagcctt ttaatatttc tctaatttag   1980
tgtatatgca atgatagttc tctgatttct gagattgagt ttctcatgtg taatgattat   2040
ttagagtttc tctttcatct gttcaaattt ttgtctagtt ttatttttta ctgatttgta   2100
agacttcttt ttataatctg catattacaa ttctctttac tggggtgttg caaatatttt   2160
ctgtcattct atggcctgac ttttcttaat ggttttttaa ttttaaaaat aagtcttaat   2220
attcatgcaa tctaattaac aatcttttct ttgtggttag actttgagt cataagaaat    2280 ttttctctac actgaagtca tgatggcatg cttctatatt attttctaaa agatttaaag   2340
ttttgccttc tccatttaga cttataattc actggaattt ttttgtgtgt atggtatgac   2400
atatgggttc ccttttatt tttacatata aatatatttc cctgttttc taaaaagaa     2460 aaagatcatc attttcccat tgtaaaatgc catattttt tcataggtca cttacatata    2520
tcaatgggtc tgtttctgag ctctactcta ttttatcagc ctcactgtct atccccacac   2580
atctcatgct ttgctctaaa tcttgatatt tagtggaaca ttctttccca ttttgttcta   2640
caagaatatt tttgttattg tctttgggct ttctatatac attttgaaat gaggttgaca   2700
agttaataat caacctctgg attacaaaat ttgtgaaaga ttgactggta ttcttaacta   2760
tgttgctcct tttacgctat gtggatacgc tgctttaatg cctttgtatc atgctattgc   2820
ttcccgtatg gctttcattt tctcctcctt gtataaatcc tggttgctgt ctctttatga   2880
ggagttgtgg cccgttgtca ggcaacgtgg cgtggtgtgc actgtgtttg ctgacgcaac   2940
ccccactggt tggggcattg ccaccacctg tcagctcctt tccgggactt tcgctttccc   3000
cctccctatt gccacggcgg aactcatcgc cgcctgcctt gcccgctgct ggacaggggc   3060
tcggctgttg ggcactgaca attccgtggt gttgtcgggg aaatcatcgt cctttccttg   3120
gctgctcgcc tgtgttgcca cctggattct gcgcgggacg tccttctgct acgtcccttc   3180
ggccctcaat ccagcggacc ttccttcccg cggcctgctg ccggctctgc ggcctcttcc   3240
gcctcttcgc cttcgccctc agacgagtcg gatctccctt tgggccgcct ccccgcatct   3300
gtgccttcta gttgccagcc atctgttgtt tgccctccc ccgtgccttc cttgaccctg    3360
gaaggtgcca ctcccactgt ccttcctaa taaaatgagg aaattgcatc gcattgtctg    3420
agtaggtgtc attctattct gggggtgg gtggggcagg acagcaaggg ggaggattgg     3480
caagacaata gcaggctttg cattttaga catttagaag cctatatctt gttacagaat    3540
tggaattaca caaaattct accatatttt gaaagcttag gttgttctga aaaaacaat     3600 atattgtttt cctgggtaaa ctaaaagtcc cctcgaggaa aggcccctaa agtgaaacag   3660
tgcaaaacgt tcaaaaactg tctggcaata caagttccac tttgaccaaa acggctggca   3720
gtaaaagggt taagaagact gtcagccttg agcggtatca gctcactcaa aggcggtaat   3780
acggttatcc acagaatcag gggataacgc aggaaagaac atgtgagcaa aaggccagca   3840
aaaggccagg aaccgtaaaa aggccgcgtt gctggcgttt ttccataggc tccgcccccc   3900
tgacgagcat cacaaaaatc gacgctcaag tcagaggtgg cgaaacccga caggactata   3960
aagataccag gcgtttcccc ctggaagctc cctcgtgcgc tctcctgttc cgaccctgcc   4020
gcttaccgga tacctgtccg cctttctccc ttcgggaagc gtggcgcttt ctcatagctc   4080
```

```
acgctgtagg tatctcagtt cggtgtaggt cgttcgctcc aagctgggct gtgtgcacga      4140
accccccgtt cagcccgacc gctgcgcctt atccggtaac tatcgtcttg agtccaaccc      4200
ggtaagacac gacttatcgc cactggcagc agccactggt aacaggatta gcagagcgag      4260
gtatgtaggc ggtgctacag agttcttgaa gtggtgggct aactacggct acactagaag      4320
aacagtattt ggtatctgcg ctctgctgaa gccagttacc ttcggaaaaa gagttggtag      4380
ctcttgatcc ggcaaacaaa ccaccgctgg tagcggtggt ttttttgttt gcaagcagca      4440
gattacgcgc agaaaaaaag gatctcaaga agatcctttg atcttttcta cggggtctga      4500
cgctcagtgg aacgacgcgc gcgtaactca cgttaaggga ttttggtcat gagttagaaa      4560
aactcatcga gcatcaaatg aaactgcaat ttattcatat caggattatc aataccatat      4620
ttttgaaaaa gccgtttctg taatgaagga gaaaactcac cgaggcagtt ccataggatg      4680
gcaagatcct ggtatcggtc tgcgattccg actcgtccaa catcaataca acctattaat      4740
ttcccctcgt caaaaataag gttatcaagt gagaaatcac catgagtgac gactgaatcc      4800
ggtgagaatg gcaaaagttt atgcatttct ttccagactt gttcaacagg ccagccatta      4860
cgctcgtcat caaaatcact cgcatcaacc aaaccgttat tcattcgtga ttgcgcctga      4920
gcgaggcgaa atacgcgatc gctgttaaaa ggacaattac aaacaggaat cgagtgcaac      4980
cggcgcagga acactgccag cgcatcaaca atattttcac ctgaatcagg atattcttct      5040
aatacctgga acgctgtttt tccggggatc gcagtggtga gtaaccatgc atcatcagga      5100
gtacggataa aatgcttgat ggtcggaagt ggcataaatt ccgtcagcca gtttagtctg      5160
accatctcat ctgtaacatc attggcaacg ctacctttgc catgtttcag aaacaactct      5220
ggcgcatcgg gcttcccata caagcgatag attgtcgcac ctgattgccc gacattatcg      5280
cgagcccatt tatacccata taatcagca tccatgttgg aatttaatcg cggcctcgac      5340
gtttcccgtt ggatatggct cattttttac ttcctcacct tgtcgtatta ctatgccg       5400
atatactatg ccgatgatta attgtcgaca ctgcggggc tctgtgtggt aagcaggtct       5460
taacctttt actgccaatg acgcatggga tacgtcgtgg cagtaaaagg cttaaatgc       5520
caacgacgcg tccatacgt tgttggcatt ttaattcttc tctctgcagc ggcagcatgt       5580
gccgccgctg cagagagttt ctagcgatga cagcccctct gggcaacgag ccggggggc       5640
tgtctttctt tatgttttaa atgcactgac ctcccacatt ccctttttag taaaatattc       5700
agaaataatt taaatacatc attgcaatga aaataaatgt tttttattag gcagaatcca       5760
gatgctcaag gcccttcata atatccccca gtttagtagt tggacttagg aacaaagga       5820
accttaata gaaattggac agcaagaaag cgagtcaggc accgggcttg cgggtcatgc       5880
accaggtgcg cggtccttcg ggcacctcga cgtcggcggt gacggtgaag ccgagccgct       5940
cgtagaaggg gaggttgcgg ggcgcggatg tctccaggaa ggcgggcacc ccggcgcgct       6000
cggccgcctc cactccgggg agcacgacgg cgctgcccag accccttgccc tggtggtcgg       6060
gcgacacgcc gacggtggcc aggaaccacg cgggctcctt gggccggtgc ggcgccagga       6120
ggccttccat ctgttgctgc gcggccagcc gggaaccgct caactcggcc atgcgcgggc       6180
cgatctcggc gaacaccgcc cccgcttcga cgctctccgg cgtggccag accgccaccg       6240
cggcgccgtc gtccgcgacc cacaccttgc cgatgtcgag cccgacgcgc gtgaggaaga       6300
gttcttgcag ctcggtgacc cgctcgatgt ggcggtccgg atcgacggtg tggcgcgtgg       6360
cggggtagtc ggcgaacgcg gcggcgaggg tgcgtacggc cctggggacg tcgtcgcggg       6420
tggcgaggcg caccgtgggc ttgtactcgg tcatggtggc ggacgaaagg cccggagatg       6480
```

-continued

```
aggaagagga gaacagcgcg gcagacgtgc gcttttgaag cgtgcagaat gccgggcctc    6540
cggaggacct tcgggcgccc gccccgcccc tgagcccgcc cctgagcccg cccccggacc    6600 cacccc ttcc cagcctctga gcccagaaag cgaaggagca aagctgctat tggccgctgc    6660
cccaaaggcc tacccgcttc cattgctcag cggtgctgtc catctgcacg agactagtga    6720
gtcgtgctac ttccatttgt cacgtcctgc acgacgcgag ctgcggggcg gggggaact     6780 tcctgactag gggaggagta aaggtggcg cgaaggggcc accaaagaac ggagccggtt     6840
ggcgcctacc ggtggatgtg aatgtgtgc gaggccagag gccacttgtg tagcgccaag     6900
tgcccagcgg ggctgctaaa gcgcatgctc cagactgcct tgggaaaagc gcctcccta    6960 cccggtagag aaacttgatc tgtcgccgca attcaaactt cgtgaggctc cggtgcccgt    7020
cagtgacctg ctatactctg gagacgactt acggtaaatg gccgcctgg ctgaccgccc    7080 aacgaccccc gcccattgac gtcaataatg acgtatgttc ccatagtaac gccaataggg    7140
actttccatt gacgtcaatg ggtggagtat ttacggtaaa ctgcccactt ggcagtacat    7200
caagtgtatc atatgccaag tccgcccccct attgacgtca atgacggtaa atggcccgcc    7260
tggcattatg cccagtacat gaccttacgg gactttccta cttggcagta catctacgta    7320
ttagtcatcg ctattaccat gctgatgcgg ttttggcagt acaccaatgg gcgtggatag    7380
cggtttgact cacggggatt tccaagtctc caccccattg acgtcaatgg gagtttgttt    7440
tggcaccaaa atcaacggga ctttccaaaa tgtcgtaata accccgcccc gttgacgcaa    7500
atgggcggta ggcgtgtacg gtgggaggtc tatataagca gagctcgttt agtgaaccgt    7560
cagatcgcct ggagaggcca tccacgctgt tttgacctcc atagtggaca ccgggaccga    7620
tccagcctcc gcgtctcagg                                                 7640
```

<210> SEQ ID NO 58
<211> LENGTH: 438
<212> TYPE: PRT
<213> ORGANISM: Artificial Sequence
<220> FEATURE:
<223> OTHER INFORMATION: Synthetic peptide, MICA-Fc

<400> SEQUENCE: 58

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
```

```
                145                 150                 155                 160
His Ala Asp Cys Leu Gln Glu Leu Arg Arg Tyr Leu Lys Ser Gly Val
                    165                 170                 175

Val Leu Arg Arg Thr Val Pro Pro Met Val Asn Val Thr Arg Ser Glu
                    180                 185                 190

Ala Ser Glu Gly Asn Ile Thr Val Thr Cys Arg Ala Ser Gly Phe Tyr
                    195                 200                 205

Pro Trp Asn Ile Thr Leu Ser Trp Arg Gln Asp Gly Val Ser Leu Ser
        210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Ser Gln Gly Glu Glu Gln Arg
                    245                 250                 255

Phe Thr Cys Tyr Met Glu His Ser Gly Asn His Ser Thr His Pro Val
                    260                 265                 270

Pro Ser Gly Lys Ile Glu Gly Arg Met Asp Pro Lys Ser Cys Asp Lys
            275                 280                 285

Thr His Thr Cys Pro Pro Cys Pro Ala Pro Glu Leu Leu Gly Gly Pro
        290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                    325                 330                 335

Pro Glu Val Lys Phe Asn Trp Tyr Val Asp Gly Val Glu Val His Asn
                    340                 345                 350

Ala Lys Thr Lys Pro Arg Glu Glu Gln Tyr Asn Ser Thr Tyr Arg Val
                    355                 360                 365

Val Ser Val Leu Thr Val Leu His Gln Asp Trp Leu Asn Gly Lys Glu
        370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                    405                 410                 415

Leu Pro Pro Ser Arg Asp Glu Leu Thr Lys Asn Gln Val Ser Leu Thr
                    420                 425                 430

Cys Leu Val Lys Gly Phe
            435

<210> SEQ ID NO 59
<211> LENGTH: 513
<212> TYPE: PRT
<213> ORGANISM: Artificial Sequence
<220> FEATURE:
<223> OTHER INFORMATION: Synthetic peptide, MICwed-Fc

<400> SEQUENCE: 59

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
        50                  55                  60

Asp Leu Thr Gly Trp Gly Lys Asp Leu Arg Met Thr Leu Ala His Ile
```

-continued

```
            65                  70                  75                  80
Lys Asp Gln Lys Glu Gly Leu His Ser Leu Gln Glu Ile Arg Val Cys
                    85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Lys Glu Trp Thr
                115                 120                 125

Met Pro Gln Ser Ser Arg Ala Gln Thr Leu Ala Met Asn Val Arg Asn
            130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
                180                 185                 190

Ala Ser Glu Gly Asn Ile Thr Val Thr Cys Arg Ala Ser Gly Phe Tyr
                195                 200                 205

Pro Trp Asn Ile Thr Leu Ser Trp Arg Gln Asp Gly Val Ser Leu Ser
            210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Ser Gln Gly Glu Glu Gln Arg
                245                 250                 255

Phe Thr Cys Tyr Met Glu His Ser Gly Asn His Ser Thr His Pro Val
                260                 265                 270

Pro Ser Gly Lys Ile Glu Gly Arg Met Asp Pro Lys Ser Cys Asp Lys
            275                 280                 285

Thr His Thr Cys Pro Pro Cys Pro Ala Pro Glu Leu Leu Gly Gly Pro
            290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
                340                 345                 350

Ala Lys Thr Lys Pro Arg Glu Glu Gln Tyr Asn Ser Thr Tyr Arg Val
            355                 360                 365

Val Ser Val Leu Thr Val Leu His Gln Asp Trp Leu Asn Gly Lys Glu
370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
                420                 425                 430

Cys Leu Val Lys Gly Phe Tyr Pro Ser Asp Ile Ala Val Glu Trp Glu
            435                 440                 445

Ser Asn Gly Gln Pro Glu Asn Asn Tyr Lys Thr Thr Pro Pro Val Leu
            450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495
```

Ala Leu His Asn His Tyr Thr Gln Lys Ser Leu Ser Leu Ser Pro Gly
            500                 505                 510

Lys

<210> SEQ ID NO 60
<211> LENGTH: 513
<212> TYPE: PRT
<213> ORGANISM: Artificial Sequence
<220> FEATURE:
<223> OTHER INFORMATION: Synthetic peptide, MICv25-Fc

<400> SEQUENCE: 60

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Ser Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Ile Glu Gly Arg Met Asp Pro Lys Ser Cys Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

```
Pro Glu Val Lys Phe Asn Trp Tyr Val Asp Gly Val Glu Val His Asn
                340                 345                 350

Ala Lys Thr Lys Pro Arg Glu Glu Gln Tyr Asn Ser Thr Tyr Arg Val
            355                 360                 365

Val Ser Val Leu Thr Val Leu His Gln Asp Trp Leu Asn Gly Lys Glu
        370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 61
<211> LENGTH: 189
<212> TYPE: PRT
<213> ORGANISM: Artificial Sequence
<220> FEATURE:
<223> OTHER INFORMATION: Synthetic peptide ULBP2 alpha1-alpha2

<400> SEQUENCE: 61

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
```

180             185

<210> SEQ ID NO 62
<211> LENGTH: 187
<212> TYPE: PRT
<213> ORGANISM: Artificial Sequence
<220> FEATURE:
<223> OTHER INFORMATION: Synthetic peptide ULBP3 alpha1-alpha2

<400> SEQUENCE: 62

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
        35                  40                  45

Gly His Leu Glu Glu Gln Leu Tyr Ala Thr Asp Ala Trp Gly Lys Gln
    50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
            100                 105                 110

Trp Gln Phe Ser Phe Asp Gly Arg Lys Phe Leu Leu Phe Asp Ser Asn
        115                 120                 125

Asn Arg Lys Trp Thr Val Val His Ala Gly Ala Arg Arg Met Lys Glu
    130                 135                 140

Lys Trp Glu Lys Asp Ser Gly Leu Thr Thr Phe Phe Lys Met Val Ser
145                 150                 155                 160

Met Arg Asp Cys Lys Ser Trp Leu Arg Asp Phe Leu Met His Arg Lys
                165                 170                 175

Lys Arg Leu Glu Pro Thr Ala Pro Pro Met Val
            180                 185

<210> SEQ ID NO 63
<211> LENGTH: 186
<212> TYPE: PRT
<213> ORGANISM: Artificial Sequence
<220> FEATURE:
<223> OTHER INFORMATION: Synthetic peptide, ULBP2 R80W

<400> SEQUENCE: 63

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
            165                 170                 175

Ser Thr Leu Glu Pro Ser Ala Gly Ala Pro
            180                 185

<210> SEQ ID NO 64
<211> LENGTH: 186
<212> TYPE: PRT
<213> ORGANISM: Artificial Sequence
<220> FEATURE:
<223> OTHER INFORMATION: Synthetic peptide, ULBP2 V151D

<400> SEQUENCE: 64

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
65                  70                  75                  80

Asp Ile Gln Leu Glu Asn Tyr Thr Pro Lys Glu Pro Leu Thr Leu Gln
            85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
130                 135                 140

Lys Trp Glu Asn Asp Lys Asp Val Ala Met Ser Phe His Tyr Phe Ser
145                 150                 155                 160

Met Gly Asp Cys Ile Gly Trp Leu Glu Asp Phe Leu Met Gly Met Asp
            165                 170                 175

Ser Thr Leu Glu Pro Ser Ala Gly Ala Pro
            180                 185

<210> SEQ ID NO 65
<211> LENGTH: 184
<212> TYPE: PRT
<213> ORGANISM: Artificial Sequence
<220> FEATURE:
<223> OTHER INFORMATION: Synthetic peptide, ULBP3 R162G

<400> SEQUENCE: 65

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
        35                  40                  45

```
Gly His Leu Glu Glu Gln Leu Tyr Ala Thr Asp Ala Trp Gly Lys Gln
            50                  55                  60

Leu Glu Met Leu Arg Glu Val Gly Gln Arg Leu Arg Leu Glu Leu Ala
 65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
                100                 105                 110

Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
        130                 135                 140

Lys Trp Glu Lys Asp Ser Gly Leu Thr Thr Phe Phe Lys Met Val Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
            180
```

<210> SEQ ID NO 66
<211> LENGTH: 182
<212> TYPE: PRT
<213> ORGANISM: Artificial Sequence
<220> FEATURE:
<223> OTHER INFORMATION: Synthetic peptide, MICA25.17

<400> SEQUENCE: 66

```
Glu Pro His Ser Leu Arg Tyr Asn Leu Thr Val Leu Ser Trp Asp Gly
 1                5                  10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Trp Gly Thr Thr Leu Leu Met Thr Leu Ala His Ile
 65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Glu Thr Asp Ile Gly Tyr Arg Leu Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180
```

<210> SEQ ID NO 67
<211> LENGTH: 182
<212> TYPE: PRT
<213> ORGANISM: Artificial Sequence

```
<220> FEATURE:
<223> OTHER INFORMATION: Synthetic peptide, MICA25.18

<400> SEQUENCE: 67

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Thr Phe Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Arg Ser Gly Leu Leu Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 68
<211> LENGTH: 186
<212> TYPE: PRT
<213> ORGANISM: Artificial Sequence
<220> FEATURE:
<223> OTHER INFORMATION: Synthetic peptide, ULBP2.S1

<400> SEQUENCE: 68

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Thr Thr Leu Tyr Thr Trp Ser
```

```
145                 150                 155                 160
Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 69
<211> LENGTH: 186
<212> TYPE: PRT
<213> ORGANISM: Artificial Sequence
<220> FEATURE:
<223> OTHER INFORMATION: Synthetic peptide, ULBP2.S2

<400> SEQUENCE: 69

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Thr Leu Met Arg Ile Trp Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 70
<211> LENGTH: 186
<212> TYPE: PRT
<213> ORGANISM: Artificial Sequence
<220> FEATURE:
<223> OTHER INFORMATION: Synthetic peptide, ULBP2.S3

<400> SEQUENCE: 70

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80
```

```
Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Gly Ser
            100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
            130                 135                 140

Lys Trp Glu Asn Asp Lys Val Val Ala Thr Lys Leu Tyr Leu Trp Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 71
<211> LENGTH: 184
<212> TYPE: PRT
<213> ORGANISM: Artificial Sequence
<220> FEATURE:
<223> OTHER INFORMATION: Synthetic peptide, ULBP3.S1

<400> SEQUENCE: 71

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
            35                  40                  45

Gly His Leu Glu Glu Gln Leu Tyr Ala Thr Asp Ala Trp Gly Lys Gln
        50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
            100                 105                 110

Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
            130                 135                 140

Lys Trp Glu Lys Asp Ser Gly Leu Thr Thr Asp Leu Ile Arg Arg Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
            180

<210> SEQ ID NO 72
<211> LENGTH: 184
<212> TYPE: PRT
<213> ORGANISM: Artificial Sequence
<220> FEATURE:
<223> OTHER INFORMATION: Synthetic peptide ULBP3.S2

<400> SEQUENCE: 72

Ala Ala Glu Pro His Ser Leu Trp Tyr Asn Phe Thr Ile Ile His Leu
1               5                   10                  15
```

```
Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
            35                  40                  45

Gly His Leu Glu Glu Gln Leu Tyr Ala Thr Asp Ala Trp Gly Lys Gln
 50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
                100                 105                 110

Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
130                 135                 140

Lys Trp Glu Lys Asp Ser Gly Leu Thr Thr Tyr Phe Tyr Leu Arg Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
            180

<210> SEQ ID NO 73
<211> LENGTH: 657
<212> TYPE: PRT
<213> ORGANISM: Artificial Sequence
<220> FEATURE:
<223> OTHER INFORMATION: Synthetic peptide, R3 HC25.17

<400> SEQUENCE: 73

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Thr Phe Thr Ser Thr
            35                  40                  45

Gly Ile Ser Trp Val Arg Gln Ala Pro Gly Lys Gly Leu Glu Trp Val
 50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
                100                 105                 110

Ala Arg Thr Tyr Gly Ile Tyr Asp Leu Tyr Val Asp Tyr Thr Glu Tyr
            115                 120                 125

Val Met Asp Tyr Trp Gly Gln Gly Thr Leu Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190
```

-continued

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Gly Gly Gly Ser Glu Pro His Ser
465                 470                 475                 480

Leu Arg Tyr Asn Leu Thr Val Leu Ser Trp Asp Gly Ser Val Gln Ser
                485                 490                 495

Gly Phe Leu Thr Glu Val His Leu Asp Gly Gln Pro Phe Leu Arg Cys
            500                 505                 510

Asp Arg Gln Lys Cys Arg Ala Lys Pro Gln Gly Gln Trp Ala Glu Asp
        515                 520                 525

Val Leu Gly Asn Lys Thr Trp Asp Arg Glu Thr Arg Asp Leu Thr Gly
530                 535                 540

Trp Gly Thr Thr Leu Leu Met Thr Leu Ala His Ile Lys Asp Gln Lys
545                 550                 555                 560

Glu Gly Leu His Ser Leu Gln Glu Ile Arg Val Cys Glu Ile His Glu
                565                 570                 575

Asp Asn Ser Thr Arg Ser Ser Gln His Phe Tyr Tyr Asp Gly Glu Leu
            580                 585                 590

Phe Leu Ser Gln Asn Leu Glu Thr Leu Glu Trp Thr Met Pro Gln Ser
        595                 600                 605

```
Ser Arg Ala Gln Thr Leu Ala Met Asn Val Arg Asn Phe Leu Lys Glu
610                 615                 620

Asp Ala Met Glu Thr Asp Ile Gly Tyr Arg Leu Met Arg Ala Asp Cys
625                 630                 635                 640

Leu Ser Glu Leu Arg Arg Tyr Leu Lys Ser Gly Val Val Leu Arg Arg
                645                 650                 655

Thr

<210> SEQ ID NO 74
<211> LENGTH: 656
<212> TYPE: PRT
<213> ORGANISM: Artificial Sequence
<220> FEATURE:
<223> OTHER INFORMATION: Synthetic peptide, R3 HC.U2S3

<400> SEQUENCE: 74

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
                20                  25                  30

Ser Leu Arg Leu Ser Cys Ala Ala Ser Gly Phe Thr Phe Thr Ser Thr
            35                  40                  45

Gly Ile Ser Trp Val Arg Gln Ala Pro Gly Lys Gly Leu Glu Trp Val
50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ala Arg Thr Tyr Gly Ile Tyr Asp Leu Tyr Val Asp Tyr Thr Glu Tyr
        115                 120                 125

Val Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
```

-continued

```
               305                 310                 315                 320

Gln Tyr Asn Ser Thr Tyr Arg Val Val Ser Val Leu Thr Val Leu His
                        325                 330                 335

Gln Asp Trp Leu Asn Gly Lys Glu Tyr Lys Cys Lys Val Ser Asn Lys
                    340                 345                 350

Ala Leu Pro Ala Pro Ile Glu Lys Thr Ile Ser Lys Ala Lys Gly Gln
                    355                 360                 365

Pro Arg Glu Pro Gln Val Tyr Thr Leu Pro Pro Ser Arg Asp Glu Leu
                370                 375                 380

Thr Lys Asn Gln Val Ser Leu Thr Cys Leu Val Lys Gly Phe Tyr Pro
        385                 390                 395                 400

Ser Asp Ile Ala Val Glu Trp Glu Ser Asn Gly Gln Pro Glu Asn Asn
                            405                 410                 415

Tyr Lys Thr Thr Pro Pro Val Leu Asp Ser Asp Gly Ser Phe Phe Leu
                        420                 425                 430

Tyr Ser Lys Leu Thr Val Asp Lys Ser Arg Trp Gln Gln Gly Asn Val
                    435                 440                 445

Phe Ser Cys Ser Val Met His Glu Ala Leu His Asn His Tyr Thr Gln
                450                 455                 460

Lys Ser Leu Ser Leu Ser Pro Gly Gly Gly Gly Ser Glu Pro His Ser
        465                 470                 475                 480

Leu Ser Tyr Asp Ile Thr Val Ile Pro Lys Phe Arg Pro Gly Pro Arg
                            485                 490                 495

Trp Cys Ala Val Gln Gly Gln Val Asp Glu Lys Thr Phe Leu His Tyr
                        500                 505                 510

Asp Cys Gly Asn Lys Thr Val Thr Pro Val Ser Pro Leu Gly Lys Lys
                    515                 520                 525

Leu Asn Val Thr Thr Ala Trp Lys Ala Gln Asn Pro Val Leu Arg Glu
                530                 535                 540

Val Val Asp Ile Leu Thr Glu Gln Leu Trp Asp Ile Gln Leu Glu Asn
        545                 550                 555                 560

Tyr Thr Pro Lys Glu Pro Leu Thr Leu Gln Ala Arg Met Ser Cys Glu
                            565                 570                 575

Gln Lys Ala Glu Gly His Ser Ser Gly Ser Trp Gln Phe Ser Phe Asp
                        580                 585                 590

Gly Gln Ile Phe Leu Leu Phe Asp Ser Glu Lys Arg Met Trp Thr Thr
                    595                 600                 605

Val His Pro Gly Ala Arg Lys Met Lys Glu Lys Trp Glu Asn Asp Lys
                610                 615                 620

Val Val Ala Thr Lys Leu Tyr Leu Trp Ser Met Gly Asp Cys Ile Gly
        625                 630                 635                 640

Trp Leu Glu Asp Phe Leu Met Gly Met Asp Ser Thr Leu Glu Pro Ser
                            645                 650                 655
```

<210> SEQ ID NO 75
<211> LENGTH: 139
<212> TYPE: PRT
<213> ORGANISM: Artificial sequence
<220> FEATURE:
<223> OTHER INFORMATION: Synthetic peptide non-natural NKG2D Y152A
      ectodomain

<400> SEQUENCE: 75

```
        Phe Leu Asn Ser Leu Phe Asn Gln Glu Val Gln Ile Pro Leu Thr Glu
        1               5                   10                  15
```

```
Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
            50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
            115                 120                 125

Pro Asn Thr Tyr Ile Cys Met Gln Arg Thr Val
            130                 135

<210> SEQ ID NO 76
<211> LENGTH: 139
<212> TYPE: PRT
<213> ORGANISM: Artificial sequence
<220> FEATURE:
<223> OTHER INFORMATION: Synthetic peptide non-natural NKG2D Y199A
      ectodomain

<400> SEQUENCE: 76

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
            50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Ala Ile Glu Asn Cys Ser Thr
            115                 120                 125

Pro Asn Thr Tyr Ile Cys Met Gln Arg Thr Val
            130                 135

<210> SEQ ID NO 77
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199A
      ectodomain

<400> SEQUENCE: 77

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30
```

Cys Tyr Gln Phe Phe Asp Glu Ser Lys Asn Trp Tyr Glu Ser Gln Ala
                35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Ala His Trp Met Gly Leu
 65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Ala Ile Glu Asn Cys Ser Thr
                115                 120                 125

Pro Asn Thr Tyr Ile Cys Met Gln Arg Thr Val
                130                 135

<210> SEQ ID NO 78
<211> LENGTH: 139
<212> TYPE: PRT
<213> ORGANISM: Artificial sequence
<220> FEATURE:
<223> OTHER INFORMATION: Synthetic peptide non-natural NKG2D Y199F
      eNKG2D1 ectodomain

<400> SEQUENCE: 78

Phe Leu Asn Ser Leu Phe Asn Gln Glu Val Gln Ile Pro Leu Thr Glu
 1               5                   10                  15

Ser Tyr Cys Gly Pro Cys Pro Lys Asn Trp Ile Cys Tyr Lys Asn Asn
                20                  25                  30

Cys Tyr Gln Phe Phe Asp Glu Ser Lys Asn Trp Tyr Glu Ser Gln Ala
                35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Tyr His Trp Met Gly Leu
 65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Phe Ile Glu Asn Cys Ser Thr
                115                 120                 125

Pro Asn Thr Tyr Ile Cys Met Gln Arg Thr Val
                130                 135

<210> SEQ ID NO 79
<211> LENGTH: 139
<212> TYPE: PRT
<213> ORGANISM: Artificial sequence
<220> FEATURE:
<223> OTHER INFORMATION: Synthetic peptide non-natural NKG2D Y152S
      eNKG2D ectodomain

<400> SEQUENCE: 79

Phe Leu Asn Ser Leu Phe Asn Gln Glu Val Gln Ile Pro Leu Thr Glu
 1               5                   10                  15

Ser Tyr Cys Gly Pro Cys Pro Lys Asn Trp Ile Cys Tyr Lys Asn Asn
                20                  25                  30

Cys Tyr Gln Phe Phe Asp Glu Ser Lys Asn Trp Tyr Glu Ser Gln Ala
                35                  40                  45

```
Ser Cys Met Ser Gln Asn Ala Ser Leu Leu Lys Val Tyr Ser Lys Glu
 50                  55                  60

Asp Gln Asp Leu Leu Lys Leu Val Lys Ser His Trp Met Gly Leu
 65                  70                  75                  80

Val His Ile Pro Thr Asn Gly Ser Trp Gln Trp Glu Asp Gly Ser Ile
                 85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Tyr Ile Glu Asn Cys Ser Thr
            115                 120                 125

Pro Asn Thr Tyr Ile Cys Met Gln Arg Thr Val
            130                 135

<210> SEQ ID NO 80
<211> LENGTH: 139
<212> TYPE: PRT
<213> ORGANISM: Artificial sequence
<220> FEATURE:
<223> OTHER INFORMATION: Synthetic peptide non-natural NKG2D Y152T
      eNKG2D3 ectodomain

<400> SEQUENCE: 80

Phe Leu Asn Ser Leu Phe Asn Gln Glu Val Gln Ile Pro Leu Thr Glu
 1               5                  10                  15

Ser Tyr Cys Gly Pro Cys Pro Lys Asn Trp Ile Cys Tyr Lys Asn Asn
                 20                  25                  30

Cys Tyr Gln Phe Phe Asp Glu Ser Lys Asn Trp Tyr Glu Ser Gln Ala
             35                  40                  45

Ser Cys Met Ser Gln Asn Ala Ser Leu Leu Lys Val Tyr Ser Lys Glu
 50                  55                  60

Asp Gln Asp Leu Leu Lys Leu Val Lys Ser Thr His Trp Met Gly Leu
 65                  70                  75                  80

Val His Ile Pro Thr Asn Gly Ser Trp Gln Trp Glu Asp Gly Ser Ile
                 85                  90                  95

Leu Ser Pro Asn Leu Leu Thr Ile Ile Glu Met Gln Lys Gly Asp Cys
                100                 105                 110

Ala Leu Tyr Ala Ser Ser Phe Lys Gly Tyr Ile Glu Asn Cys Ser Thr
            115                 120                 125

Pro Asn Thr Tyr Ile Cys Met Gln Arg Thr Val
            130                 135

<210> SEQ ID NO 81
<211> LENGTH: 139
<212> TYPE: PRT
<213> ORGANISM: Artificial sequence
<220> FEATURE:
<223> OTHER INFORMATION: Synthetic peptide non-natural NKG2D Y152V
      eNKG2D4 ectodomain

<400> SEQUENCE: 81

Phe Leu Asn Ser Leu Phe Asn Gln Glu Val Gln Ile Pro Leu Thr Glu
 1               5                  10                  15

Ser Tyr Cys Gly Pro Cys Pro Lys Asn Trp Ile Cys Tyr Lys Asn Asn
                 20                  25                  30

Cys Tyr Gln Phe Phe Asp Glu Ser Lys Asn Trp Tyr Glu Ser Gln Ala
             35                  40                  45

Ser Cys Met Ser Gln Asn Ala Ser Leu Leu Lys Val Tyr Ser Lys Glu
 50                  55                  60
```

```
Asp Gln Asp Leu Leu Lys Leu Val Lys Ser Val His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 82
<211> LENGTH: 139
<212> TYPE: PRT
<213> ORGANISM: Artificial sequence
<220> FEATURE:
<223> OTHER INFORMATION: Synthetic peptide non-natural NKG2D Y152A/Y199F
      eNKG2D5 ectodomain

<400> SEQUENCE: 82

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Ala His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 83
<211> LENGTH: 139
<212> TYPE: PRT
<213> ORGANISM: Artificial sequence
<220> FEATURE:
<223> OTHER INFORMATION: Synthetic peptide non-natural NKG2D Y152L/Y199F
      eNKG2D6 ectodomain

<400> SEQUENCE: 83

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Leu His Trp Met Gly Leu
65                  70                  75                  80
```

Val His Ile Pro Thr Asn Gly Ser Trp Gln Trp Glu Asp Gly Ser Ile
             85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
            115                 120                 125

Pro Asn Thr Tyr Ile Cys Met Gln Arg Thr Val
            130                 135

<210> SEQ ID NO 84
<211> LENGTH: 139
<212> TYPE: PRT
<213> ORGANISM: Artificial sequence
<220> FEATURE:
<223> OTHER INFORMATION: Synthetic peptide non-natural NKG2D Y152S/Y199F
      eNKG2D7 ectodomain

<400> SEQUENCE: 84

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Ser His Trp Met Gly Leu
65                  70                  75                  80

Val His Ile Pro Thr Asn Gly Ser Trp Gln Trp Glu Asp Gly Ser Ile
             85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
            115                 120                 125

Pro Asn Thr Tyr Ile Cys Met Gln Arg Thr Val
            130                 135

<210> SEQ ID NO 85
<211> LENGTH: 139
<212> TYPE: PRT
<213> ORGANISM: Artificial sequence
<220> FEATURE:
<223> OTHER INFORMATION: Synthetic peptide non-natural NKG2D Y152T/Y199F
      eNKG2D8 ectodomain

<400> SEQUENCE: 85

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
            35                  40                  45

Ser Cys Met Ser Gln Asn Ala Ser Leu Leu Lys Val Tyr Ser Lys Glu
        50                  55                  60

Asp Gln Asp Leu Leu Lys Leu Val Lys Ser Thr His Trp Met Gly Leu
65                  70                  75                  80

Val His Ile Pro Thr Asn Gly Ser Trp Gln Trp Glu Asp Gly Ser Ile
             85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
        130                 135

<210> SEQ ID NO 86
<211> LENGTH: 139
<212> TYPE: PRT
<213> ORGANISM: Artificial sequence
<220> FEATURE:
<223> OTHER INFORMATION: Synthetic peptide non-natural NKG2D Y152V/Y199F
      eNKG2D9 ectodomain

<400> SEQUENCE: 86

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Val His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
        130                 135

<210> SEQ ID NO 87
<211> LENGTH: 139
<212> TYPE: PRT
<213> ORGANISM: Artificial sequence
<220> FEATURE:
<223> OTHER INFORMATION: Synthetic peptide non-natural NKG2D Y199D
      eNKG2D10 ectodomain

<400> SEQUENCE: 87

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Asp Ile Glu Asn Cys Ser Thr
            115                 120                 125

Pro Asn Thr Tyr Ile Cys Met Gln Arg Thr Val
    130                 135

<210> SEQ ID NO 88
<211> LENGTH: 139
<212> TYPE: PRT
<213> ORGANISM: Artificial sequence
<220> FEATURE:
<223> OTHER INFORMATION: Synthetic peptide non-natural NKG2D Y199E
      eNKG2D11 ectodomain

<400> SEQUENCE: 88

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Glu Ile Glu Asn Cys Ser Thr
            115                 120                 125

Pro Asn Thr Tyr Ile Cys Met Gln Arg Thr Val
    130                 135

<210> SEQ ID NO 89
<211> LENGTH: 139
<212> TYPE: PRT
<213> ORGANISM: Artificial sequence
<220> FEATURE:
<223> OTHER INFORMATION: Synthetic peptide non-natural NKG2D Y152D/Y199D
      eNKG2D12 ectodomain

<400> SEQUENCE: 89

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Asp His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Asp Ile Glu Asn Cys Ser Thr
            115                 120                 125

```
Pro Asn Thr Tyr Ile Cys Met Gln Arg Thr Val
    130                 135
```

<210> SEQ ID NO 90
<211> LENGTH: 139
<212> TYPE: PRT
<213> ORGANISM: Artificial sequence
<220> FEATURE:
<223> OTHER INFORMATION: Synthetic peptide non-natural NKG2D Y152E/Y199E
      eNKG2D13 ectodomain

<400> SEQUENCE: 90

```
Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Glu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Glu Ile Glu Asn Cys Ser Thr
        115                 120                 125

Pro Asn Thr Tyr Ile Cys Met Gln Arg Thr Val
    130                 135
```

<210> SEQ ID NO 91
<211> LENGTH: 139
<212> TYPE: PRT
<213> ORGANISM: Artificial sequence
<220> FEATURE:
<223> OTHER INFORMATION: Synthetic peptide non-natural NKG2D Y152L
      eNKG2D14 ectodomain

<400> SEQUENCE: 91

```
Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Leu His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135
```

```
<210> SEQ ID NO 92
<211> LENGTH: 139
<212> TYPE: PRT
<213> ORGANISM: Artificial sequence
<220> FEATURE:
<223> OTHER INFORMATION: Synthetic peptide non-natural NKG2D Y152F/Y199F
      eNKG2D15 ectodomain

<400> SEQUENCE: 92

Phe Leu Asn Ser Leu Phe Asn Gln Glu Val Gln Ile Pro Leu Thr Glu
1               5                   10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Phe His Trp Met Gly Leu
65                  70                  75                  80

Val His Ile Pro Thr Asn Gly Ser Trp Gln Trp Glu Asp Gly Ser Ile
                85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Phe Ile Glu Asn Cys Ser Thr
        115                 120                 125

Pro Asn Thr Tyr Ile Cys Met Gln Arg Thr Val
    130                 135

<210> SEQ ID NO 93
<211> LENGTH: 237
<212> TYPE: PRT
<213> ORGANISM: Artificial sequence
<220> FEATURE:
<223> OTHER INFORMATION: Synthetic peptide human IgG1 Fc with IEGR
      linker

<400> SEQUENCE: 93

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160
```

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg
225                 230                 235

<210> SEQ ID NO 94
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D fusion

<400> SEQUENCE: 94

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
                355                 360                 365

Tyr Ile Cys Met Gln Arg Thr Val
    370                 375

<210> SEQ ID NO 95
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152A
      fusion

<400> SEQUENCE: 95

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

-continued

```
Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
        290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
                340                 345                 350

Ala Ser Ser Phe Lys Gly Tyr Ile Glu Asn Cys Ser Thr Pro Asn Thr
            355                 360                 365

Tyr Ile Cys Met Gln Arg Thr Val
            370                 375

<210> SEQ ID NO 96
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199A
      ectodomain

<400> SEQUENCE: 96

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
```

```
                    245                 250                 255
Gly Pro Cys Pro Lys Asn Trp Ile Cys Tyr Lys Asn Cys Tyr Gln
            260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
        290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Ala Ile Glu Asn Cys Ser Thr Pro Asn Thr
        355                 360                 365

Tyr Ile Cys Met Gln Arg Thr Val
        370                 375

<210> SEQ ID NO 97
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199A ectodomain

<400> SEQUENCE: 97

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220
```

```
Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
            245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
            290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
            325                 330                 335

Asn Leu Leu Thr Ile Ile Glu Met Gln Lys Gly Asp Cys Ala Leu Tyr
            340                 345                 350

Ala Ser Ser Phe Lys Gly Ala Ile Glu Asn Cys Ser Thr Pro Asn Thr
            355                 360                 365

Tyr Ile Cys Met Gln Arg Thr Val
            370                 375

<210> SEQ ID NO 98
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199F
      eNKG2D1 fusion

<400> SEQUENCE: 98

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205
```

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 99
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152S
      eNKG2D2 fusion

<400> SEQUENCE: 99

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu

```
                180                 185                 190
Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
        210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 100
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152T
      eNKG2D3 fusion

<400> SEQUENCE: 100

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160
```

```
Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
        210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
            275                 280                 285

Ser Gln Asn Ala Ser Leu Leu Lys Val Tyr Ser Lys Glu Asp Gln Asp
        290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
            355                 360                 365

Tyr Ile Cys Met Gln Arg Thr Val
370                 375

<210> SEQ ID NO 101
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152V
      eNKG2D4 fusion

<400> SEQUENCE: 101

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140
```

```
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Val His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Tyr Ile Glu Asn Cys Ser Thr Pro Asn Thr
        355                 360                 365

Tyr Ile Cys Met Gln Arg Thr Val
    370                 375

<210> SEQ ID NO 102
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152A/Y199F eNKG2D5 fusion

<400> SEQUENCE: 102

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
```

```
              115                 120                 125
Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Ala His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
370                 375

<210> SEQ ID NO 103
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152L/Y199F eNKG2D6 fusion

<400> SEQUENCE: 103

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95
```

```
Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Leu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
370                 375

<210> SEQ ID NO 104
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152S/Y199F eNKG2D7 fusion

<400> SEQUENCE: 104

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80
```

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Ser His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 105
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152T/Y199F eNKG2D8 fusion

<400> SEQUENCE: 105

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr

```
                50                  55                  60
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Thr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 106
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152V/Y199F eNKG2D9 fusion

<400> SEQUENCE: 106

Met Asp Pro Lys Ser Cys Asp Lys Thr His Thr Cys Pro Pro Cys Pro
  1               5                  10                  15

Ala Pro Glu Leu Leu Gly Gly Pro Ser Val Phe Leu Phe Pro Pro Lys
             20                  25                  30
```

```
Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Val His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 107
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199D
      eNKG2D10 fusion

<400> SEQUENCE: 107

Met Asp Pro Lys Ser Cys Asp Lys Thr His Thr Cys Pro Pro Cys Pro
 1               5                  10                  15
```

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Asp Ile Glu Asn Cys Ser Thr Pro Asn Thr
        355                 360                 365

Tyr Ile Cys Met Gln Arg Thr Val
370                 375

<210> SEQ ID NO 108
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y199E
      eNKG2D11 fusion

```
<400> SEQUENCE: 108

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Tyr His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Glu Ile Glu Asn Cys Ser Thr Pro Asn Thr
        355                 360                 365

Tyr Ile Cys Met Gln Arg Thr Val
    370                 375

<210> SEQ ID NO 109
<211> LENGTH: 376
<212> TYPE: PRT
<213> ORGANISM: Artificial sequence
```

<220> FEATURE:
<223> OTHER INFORMATION: Synthetic peptide human IgG1 Fc-NKG2D
Y152D/Y199D eNKG2D12 fusion

<400> SEQUENCE: 109

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
290                 295                 300

Leu Leu Lys Leu Val Lys Ser Asp His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Asp Ile Glu Asn Cys Ser Thr Pro Asn Thr
        355                 360                 365

Tyr Ile Cys Met Gln Arg Thr Val
370                 375

<210> SEQ ID NO 110
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152E/Y199E eNKG2D13 fusion

<400> SEQUENCE: 110

```
Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Glu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

Ala Ser Ser Phe Lys Gly Glu Ile Glu Asn Cys Ser Thr Pro Asn Thr
        355                 360                 365
```

Tyr Ile Cys Met Gln Arg Thr Val
    370                 375

<210> SEQ ID NO 111
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D Y152L
      eNKG2D14 fusion

<400> SEQUENCE: 111

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Leu His Trp Met Gly Leu Val His Ile
305                 310                 315                 320

Pro Thr Asn Gly Ser Trp Gln Trp Glu Asp Gly Ser Ile Leu Ser Pro
                325                 330                 335

Asn Leu Leu Thr Ile Ile Glu Met Gln Lys Gly Asp Cys Ala Leu Tyr
            340                 345                 350

```
Ala Ser Ser Phe Lys Gly Tyr Ile Glu Asn Cys Ser Thr Pro Asn Thr
        355                 360                 365
Tyr Ile Cys Met Gln Arg Thr Val
    370                 375

<210> SEQ ID NO 112
<211> LENGTH: 376
<212> TYPE: PRT
<213> ORGANISM: Artificial sequence
<220> FEATURE:
<223> OTHER INFORMATION: Synthetic peptide human IgG1 Fc-NKG2D
      Y152F/Y199F eNKG2D15 fusion

<400> SEQUENCE: 112

Met Asp Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Ile Glu Gly Arg Phe Leu Asn
225                 230                 235                 240

Ser Leu Phe Asn Gln Glu Val Gln Ile Pro Leu Thr Glu Ser Tyr Cys
                245                 250                 255

Gly Pro Cys Pro Lys Asn Trp Ile Cys Tyr Lys Asn Asn Cys Tyr Gln
            260                 265                 270

Phe Phe Asp Glu Ser Lys Asn Trp Tyr Glu Ser Gln Ala Ser Cys Met
        275                 280                 285

Ser Gln Asn Ala Ser Leu Leu Lys Val Tyr Ser Lys Glu Asp Gln Asp
    290                 295                 300

Leu Leu Lys Leu Val Lys Ser Phe His Trp Met Gly Leu Val His Ile
305                 310                 315                 320

Pro Thr Asn Gly Ser Trp Gln Trp Glu Asp Gly Ser Ile Leu Ser Pro
```

```
                    325                 330                 335
Asn Leu Leu Thr Ile Ile Glu Met Gln Lys Gly Asp Cys Ala Leu Tyr
            340                 345                 350

Ala Ser Ser Phe Lys Gly Phe Ile Glu Asn Cys Ser Thr Pro Asn Thr
        355                 360                 365

Tyr Ile Cys Met Gln Arg Thr Val
    370                 375

<210> SEQ ID NO 113
<211> LENGTH: 23
<212> TYPE: PRT
<213> ORGANISM: Artificial sequence
<220> FEATURE:
<223> OTHER INFORMATION: Synthetic peptide MHCI signal sequence

<400> SEQUENCE: 113

Met Gly Leu Gly Pro Val Phe Leu Leu Leu Ala Gly Ile Phe Pro Phe
1               5                   10                  15

Ala Pro Pro Gly Ala Ala Ala
            20

<210> SEQ ID NO 114
<211> LENGTH: 69
<212> TYPE: DNA
<213> ORGANISM: Artificial sequence
<220> FEATURE:
<223> OTHER INFORMATION: Synthetic polynucleotide, encoding MHCI signal
      sequence

<400> SEQUENCE: 114
atgggccttg gcccagtgtt tctgctgttg gcaggcattt tcccttttgc tccgcccggc    60
gccgcagcc                                                            69

<210> SEQ ID NO 115
<211> LENGTH: 711
<212> TYPE: DNA
<213> ORGANISM: Artificial sequence
<220> FEATURE:
<223> OTHER INFORMATION: Synthetic polynucleotide, encoding human IgG1
      Fc with IEGR linker

<400> SEQUENCE: 115
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcacccctg aagtgacctg tgtcgtcgtg gatgtgtcac acgaggaccc ggaggtcaag   180
ttcaattggt acgtggacgg cgtggaagtg cataacgcaa agaccaagcc tcggggggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg c             711

<210> SEQ ID NO 116
```

<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D fusion

<400> SEQUENCE: 116

| | | | |
|---|---|---|---|
| atggacccga | aaagctgcga | caagactcac | acttgtccgc cgtgccccgc ccccgaactg | 60 |
| ctgggtggcc | cctccgtgtt | cctgttcccg | cctaagccta aggacaccct tatgatcagc | 120 |
| cgcacccctg | aagtgacctg | tgtcgtcgtg | gatgtgtcac acgaggaccc ggaggtcaag | 180 |
| ttcaattggt | acgtggacgg | cgtggaagtg | cataacgcaa agaccaagcc tcgggaggaa | 240 |
| cagtacaact | cgacctaccg | cgtggtgtca | gtcctgactg tgctgcacca ggactggctg | 300 |
| aacgggaagg | agtacaagtg | caaagtgtcg | aacaaggccc tgccggctcc aattgaaaag | 360 |
| accatcagca | aggccaaggg | ccagccaagg | gaaccacagg tgtacaccct ccctccttcc | 420 |
| cgggacgagc | tgaccaaaaa | ccaagtgtcc | ctgacttgcc ttgtgaaggg gttctaccct | 480 |
| tctgacattg | ccgtcgaatg | ggaatcgaac | ggacagcctg aaaacaacta taagactacc | 540 |
| ccgcccgtgc | tggattccga | cggaagcttc | ttcctgtact ccaagctgac cgtggacaag | 600 |
| tcgagatggc | agcagggaaa | tgtgttcagc | tgctccgtga tgcatgaggc gctgcacaac | 660 |
| cactacaccc | agaagtcact | gagcctctcc | cccggaaaga tcgaaggacg cttcttaaac | 720 |
| tcattattca | accaagaagt | tcaaattccc | ttgaccgaaa gttactgtgg cccatgtcct | 780 |
| aaaaactgga | tatgttacaa | aaataactgc | taccaattttt ttgatgagag taaaaactgg | 840 |
| tatgagagcc | aggcttcttg | tatgtctcaa | aatgccagcc ttctgaaagt atacagcaaa | 900 |
| gaggaccagg | atttacttaa | actggtgaag | tcatatcatt ggatgggact agtcacacatt | 960 |
| ccaacaaatg | gatcttggca | gtgggaagat | ggctccattc tctcacccaa cctactaaca | 1020 |
| ataattgaaa | tgcagaaggg | agactgtgca | ctctatgcct cgagctttaa aggctatata | 1080 |
| gaaaactgtt | caactccaaa | tacatacatc | tgcatgcaaa ggactgtg | 1128 |

<210> SEQ ID NO 117
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152A fusion

<400> SEQUENCE: 117

| | | | |
|---|---|---|---|
| atggacccga | aaagctgcga | caagactcac | acttgtccgc cgtgccccgc ccccgaactg | 60 |
| ctgggtggcc | cctccgtgtt | cctgttcccg | cctaagccta aggacaccct tatgatcagc | 120 |
| cgcacccctg | aagtgacctg | tgtcgtcgtg | gatgtgtcac acgaggaccc ggaggtcaag | 180 |
| ttcaattggt | acgtggacgg | cgtggaagtg | cataacgcaa agaccaagcc tcgggaggaa | 240 |
| cagtacaact | cgacctaccg | cgtggtgtca | gtcctgactg tgctgcacca ggactggctg | 300 |
| aacgggaagg | agtacaagtg | caaagtgtcg | aacaaggccc tgccggctcc aattgaaaag | 360 |
| accatcagca | aggccaaggg | ccagccaagg | gaaccacagg tgtacaccct ccctccttcc | 420 |
| cgggacgagc | tgaccaaaaa | ccaagtgtcc | ctgacttgcc ttgtgaaggg gttctaccct | 480 |
| tctgacattg | ccgtcgaatg | ggaatcgaac | ggacagcctg aaaacaacta taagactacc | 540 |
| ccgcccgtgc | tggattccga | cggaagcttc | ttcctgtact ccaagctgac cgtggacaag | 600 |
| tcgagatggc | agcagggaaa | tgtgttcagc | tgctccgtga tgcatgaggc gctgcacaac | 660 |

```
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcagctcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg               1128
```

<210> SEQ ID NO 118
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y199A ectodomain

<400> SEQUENCE: 118

```
atggacccga aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcgctata   1080
gaaaactgtt caactccaaa tacatacatc tgcatgcaaa ggactgtg               1128
```

<210> SEQ ID NO 119
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152A/Y199A ectodomain

<400> SEQUENCE: 119

```
atggacccga aaagctgcga caagactcac acttgtccgc cgtgccccgc ccccgaactg     60
```

```
ctgggtggcc cctccgtgtt cctgttcccg cctaagccta aggacaccct tatgatcagc     120 cgcaccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt tgatgagag taaaaactgg     840 tatgagagcc aggcttcttg tatgtctcaa aatgccagcc ttctgaaagt atacagcaaa     900
gaggaccagg atttacttaa actggtgaag tcagctcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcgctata    1080
gaaaactgtt caactccaaa tacatacatc tgcatgcaaa ggactgtg               1128
```

<210> SEQ ID NO 120
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y199F eNKG2D1 fusion

<400> SEQUENCE: 120

```
atggacccga aaagctgcga caagactcac acttgtccgc cgtgccccgc ccccgaactg      60
ctgggtggcc cctccgtgtt cctgttcccg cctaagccta aggacaccct tatgatcagc     120 cgcaccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt tgatgagag taaaaactgg     840 tatgagagcc aggcttcttg tatgtctcaa aatgccagcc ttctgaaagt atacagcaaa     900
gaggaccagg atttacttaa actggtgaag tcataccatt ggatgggact agtacacatt     960
```

-continued

```
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 121
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152S eNKG2D2 fusion

<400> SEQUENCE: 121

```
atggaccega aaagctgcga caagactcac acttgtccgc cgtgccccgc ccccgaactg    60
ctgggtggcc cctccgtgtt cctgttcccg cctaagccta aggacaccct tatgatcagc    120 cgcaccectg aagtgacctg tgtcgtcgtg gatgtgtcac acgaggaccc ggaggtcaag    180
ttcaattggt acgtggacgg cgtggaagtg cataacgcaa agaccaagcc tcggaggaa    240 cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta aagactacc    540 ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca ccaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa atgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 122
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152T eNKG2D3 fusion

<400> SEQUENCE: 122

```
atggaccega aaagctgcga caagactcac acttgtccgc cgtgccccgc ccccgaactg    60
ctgggtggcc cctccgtgtt cctgttcccg cctaagccta aggacaccct tatgatcagc    120 cgcaccectg aagtgacctg tgtcgtcgtg gatgtgtcac acgaggaccc ggaggtcaag    180
ttcaattggt acgtggacgg cgtggaagtg cataacgcaa agaccaagcc tcggaggaa    240 cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
```

```
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcaactcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggctatata     1080
gaaaactgtt caactccaaa tacatacatc tgcatgcaaa ggactgtg                  1128

<210> SEQ ID NO 123
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152V eNKG2D4 fusion

<400> SEQUENCE: 123
atggacccga aaagctgcga caagactcac acttgtccgc cgtgccccgc ccccgaactg       60
ctgggtggcc cctccgtgtt cctgttcccg cctaagccta aggacaccct tatgatcagc      120
cgcacccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa      240
cagtacaact cgacctaccg cgtggtgtca gtcctgactg tgctgcacca ggactggctg      300
aacgggaagg agtacaagtg caaagtgtcg aacaaggccc tgccggctcc aattgaaaag      360
accatcagca aggccaaggg ccagccaagg gaaccacagg tgtacaccct ccctccttcc      420
cgggacgagc tgaccaaaaa ccaagtgtcc ctgacttgcc ttgtgaaggg gttctaccct      480
tctgacattg ccgtcgaatg ggaatcgaac ggacagcctg aaaacaacta taagactacc      540
ccgcccgtgc tggattccga cggaagcttc ttcctgtact ccaagctgac cgtggacaag      600
tcgagatggc agcagggaaa tgtgttcagc tgctccgtga tgcatgaggc gctgcacaac      660
cactacaccc agaagtcact gagcctctcc cccggaaaga tcgaaggacg cttcttaaac      720
tcattattca accaagaagt tcaaattccc ttgaccgaaa gttactgtgg cccatgtcct      780
aaaaactgga tatgttacaa aaataactgc taccaatttt ttgatgagag taaaaactgg      840
tatgagagcc aggcttcttg tatgtctcaa aatgccagcc ttctgaaagt atacagcaaa      900
gaggaccagg atttacttaa actggtgaag tcagtgcatt ggatgggact agtacacatt      960
ccaacaaatg gatcttggca gtgggaagat ggctccattc tctcacccaa cctactaaca     1020
ataattgaaa tgcagaaggg agactgtgca ctctatgcct cgagctttaa aggctatata     1080
gaaaactgtt caactccaaa tacatacatc tgcatgcaaa ggactgtg                  1128

<210> SEQ ID NO 124
<211> LENGTH: 1128
<212> TYPE: DNA
<213> ORGANISM: Artificial sequence
```

<220> FEATURE:
<223> OTHER INFORMATION: Synthetic polynucleotide, encoding human IgG1
      Fc-NKG2D Y152A/Y199F eNKG2D5 fusion

<400> SEQUENCE: 124

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aataactgc taccaatttt tgatgagag taaaaactgg      840
tatgagagcc aggcttcttg tatgtctcaa aatgccagcc ttctgaaagt atacagcaaa     900
gaggaccagg atttacttaa actggtgaag tcagctcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg               1128
```

<210> SEQ ID NO 125
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152L/Y199F eNKG2D6 fusion

<400> SEQUENCE: 125

```
atggacccga aaagctgcga caagactcac acttgtccgc cgtgccccgc ccccgaactg      60
ctgggtggcc cctccgtgtt cctgttcccg cctaagccta aggacaccct tatgatcagc     120
cgcaccctg aagtgacctg tgtcgtcgtg gatgtgtcac acgaggaccc ggaggtcaag      180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
```

```
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa atgccagcc ttctgaaagt atacagcaaa    900
gaggaccagg atttacttaa actggtgaag tcactgcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg               1128
```

<210> SEQ ID NO 126
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152S/Y199F eNKG2D7 fusion

<400> SEQUENCE: 126

```
atggaccega aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
ttcaattggt acgtggacgg cgtggaagtg cataacgcaa agaccaagcc tcggaggaa    240 cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa atgccagcc ttctgaaagt atacagcaaa    900
gaggaccagg atttacttaa actggtgaag tcaagtcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg               1128
```

<210> SEQ ID NO 127
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152T/Y199F eNKG2D8 fusion

<400> SEQUENCE: 127

```
atggaccega aaagctgcga caagactcac acttgtccgc cgtgccccgc ccccgaactg     60
ctgggtggcc cctccgtgtt cctgttcccg cctaagccta aggacaccct tatgatcagc    120
cgcacccctg aagtgacctg tgtcgtcgtg gatgtgtcac acgaggaccc ggaggtcaag    180
```

```
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcaactcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
gaaaactgtt caactccaaa tacatacatc tgcatgcaaa ggactgtg                 1128
```

<210> SEQ ID NO 128
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y152V/Y199F eNKG2D9 fusion

<400> SEQUENCE: 128

```
atggaccega aaagctgcga caagactcac acttgtccgc cgtgccccgc cccgaactg       60 ctgggtggcc cctccgtgtt cctgttcccg cctaagccta aggacaccct tatgatcagc     120
cgcacccctg aagtgacctg tgtcgtcgtg gatgtgtcac acgaggaccc ggaggtcaag     180
ttcaattggt acgtggacgg cgtggaagtg cataacgcaa agaccaagcc tcgggaggaa     240
cagtacaact cgacctaccg cgtggtgtca gtcctgactg tgctgcacca ggactggctg     300
aacgggaagg agtacaagtg caaagtgtcg aacaaggccc tgccggctcc aattgaaaag     360
accatcagca aggccaaggg ccagccaagg gaaccacagg tgtacaccct ccctccttcc     420
cgggacgagc tgaccaaaaa ccaagtgtcc ctgacttgcc ttgtgaaggg gttctaccct     480
tctgacattg ccgtcgaatg ggaatcgaac ggacagcctg aaaacaacta taagactacc     540
ccgcccgtgc tggattccga cggaagcttc ttcctgtact ccaagctgac cgtggacaag     600
tcgagatggc agcagggaaa tgtgttcagc tgctccgtga tgcatgaggc gctgcacaac     660
cactacaccc agaagtcact gagcctctcc cccggaaaga tcgaaggacg cttcttaaac     720
tcattattca accaagaagt tcaaattccc ttgaccgaaa gttactgtgg cccatgtcct     780
aaaaactgga tatgttacaa aaataactgc taccaatttt ttgatgagag taaaaactgg     840
tatgagagcc aggcttcttg tatgtctcaa aatgccagcc ttctgaaagt atacagcaaa     900
gaggaccagg atttacttaa actggtgaag tcagtgcatt ggatgggact agtacacatt     960
ccaacaaatg gatcttggca gtgggaagat ggctccattc tctcacccaa cctactaaca    1020
ataattgaaa tgcagaaggg agactgtgca ctctatgcct cgagctttaa aggcttcata    1080
```
gaaaactgtt caactccaaa tacatacatc tgcatgcaaa ggactgtg         1128

<210> SEQ ID NO 129
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y199D eNKG2D10 fusion

<400> SEQUENCE: 129

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcaccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
tatgagagcc aggcttcttg tatgtctcaa aatgccagcc ttctgaaagt atacagcaaa   900
gaggaccagg atttacttaa actggtgaag tcatatcatt ggatgggact agtacacatt   960
ccaacaaatg gatcttggca gtgggaagat ggctccattc tctcacccaa cctactaaca  1020
ataattgaaa tgcagaaggg agactgtgca ctctatgcct cgagctttaa aggcgatata  1080
gaaaactgtt caactccaaa tacatacatc tgcatgcaaa ggactgtg             1128
```

<210> SEQ ID NO 130
<211> LENGTH: 1128
<212> TYPE: DNA
<213> ORGANISM: Artificial sequence
<220> FEATURE:
<223> OTHER INFORMATION: Synthetic polynucleotide, encoding human IgG1
      Fc-NKG2D Y199E eNKG2D11 fusion

<400> SEQUENCE: 130

```
atggacccga aaagctgcga caagactcac acttgtccgc cgtgccccgc ccccgaactg    60
ctgggtggcc cctccgtgtt cctgttcccg cctaagccta aggacaccct tatgatcagc   120
cgcaccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
```

```
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcataccatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcgagata   1080
gaaaactgtt caactccaaa tacatacatc tgcatgcaaa ggactgtg               1128
```

<210> SEQ ID NO 131
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152D/Y199D eNKG2D12 fusion

<400> SEQUENCE: 131

```
atggacccga aaagctgcga caagactcac acttgtccgc cgtgccccgc ccccgaactg     60
ctgggtggcc cctccgtgtt cctgttcccg cctaagccta aggacaccct tatgatcagc    120 cgcaccccctg aagtgacctg tgtcgtcgtg gatgtgtcac acgaggaccc ggaggtcaag    180
ttcaattggt acgtggacgg cgtggaagtg cataacgcaa agaccaagcc tcgggaggaa    240
cagtacaact cgacctaccg cgtggtgtca gtcctgactg tgctgcacca ggactggctg    300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcagatcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcgatata   1080
gaaaactgtt caactccaaa tacatacatc tgcatgcaaa ggactgtg               1128
```

<210> SEQ ID NO 132
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152E/Y199E eNKG2D13 fusion

<400> SEQUENCE: 132

```
atggacccga aaagctgcga caagactcac acttgtccgc cgtgcccgc ccccgaactg    60
ctgggtggcc cctccgtgtt cctgttcccg cctaagccta aggacaccct tatgatcagc   120
cgcaccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
tatgagagcc aggcttcttg tatgtctcaa aatgccagcc ttctgaaagt atacagcaaa   900
gaggaccagg atttacttaa actggtgaag tcagagcatt ggatgggact agtacacatt   960
ccaacaaatg gatcttggca gtgggaagat ggctccattc tctcacccaa cctactaaca  1020
ataattgaaa tgcagaaggg agactgtgca ctctatgcct cgagctttaa aggcgagata  1080
gaaaactgtt caactccaaa tacatacatc tgcatgcaaa ggactgtg              1128
```

<210> SEQ ID NO 133
<211> LENGTH: 1128
<212> TYPE: DNA
<213> ORGANISM: Artificial sequence
<220> FEATURE:
<223> OTHER INFORMATION: Synthetic polynucleotide, encoding human IgG1 Fc-NKG2D Y152L eNKG2D14 fusion

<400> SEQUENCE: 133

```
atggacccga aaagctgcga caagactcac acttgtccgc cgtgcccgc ccccgaactg    60
ctgggtggcc cctccgtgtt cctgttcccg cctaagccta aggacaccct tatgatcagc   120
cgcaccctg aagtgacctg tgtcgtcgtg gatgtgtcac acgaggaccc ggaggtcaag   180
ttcaattggt acgtggacgg cgtggaagtg cataacgcaa agaccaagcc tcgggaggaa   240
cagtacaact cgacctaccg cgtggtgtca gtcctgactg tgctgcacca ggactggctg   300
aacgggaagg agtacaagtg caaagtgtcg aacaaggccc tgccggctcc aattgaaaag   360
accatcagca aggccaaggg ccagccaagg gaaccacagg tgtacaccct ccctccttcc   420
cgggacgagc tgaccaaaaa ccaagtgtcc ctgacttgcc ttgtgaaggg gttctaccct   480
tctgacattg ccgtcgaatg ggaatcgaac ggacagcctg aaaacaacta taagactacc   540
ccgcccgtgc tggattccga cggaagcttc ttcctgtact ccaagctgac cgtggacaag   600
tcgagatggc agcagggaaa tgtgttcagc tgctccgtga tgcatgaggc gctgcacaac   660
cactacaccc agaagtcact gagcctctcc cccggaaaga tcgaaggacg cttcttaaac   720
tcattattca accaagaagt tcaaattccc ttgaccgaaa gttactgtgg cccatgtcct   780
aaaaactgga tatgttacaa aaataactgc taccaatttt ttgatgagag taaaaactgg   840
```

```
tatgagagcc aggcttcttg tatgtctcaa aatgccagcc ttctgaaagt atacagcaaa    900
gaggaccagg atttacttaa actggtgaag tcactgcatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggctatata   1080
gaaaactgtt caactccaaa tacatacatc tgcatgcaaa ggactgtg              1128
```

<210> SEQ ID NO 134
<211> LENGTH: 1128
<212> TYPE: DNA
<213> ORGANISM: Artificial sequence
<220> FEATURE:
<223> OTHER INFORMATION: Synthetic polynucleotide, encoding human IgG1
    Fc-NKG2D Y152F/Y199F eNKG2D15 fusion

<400> SEQUENCE: 134

```
atggaccega aaagctgcga caagactcac acttgtccgc cgtgccccgc ccccgaactg     60
ctgggtggcc cctccgtgtt cctgttcccg cctaagccta aggacaccct tatgatcagc    120 cgcaccccctg aagtgacctg tgtcgtcgtg gatgtgtcac acgaggaccc ggaggtcaag   180
ttcaattggt acgtggacgg cgtggaagtg cataacgcaa agaccaagcc tcggaggaa    240 cagtacaact cgacctaccg cgtggtgtca gtcctgactg tgctgcacca ggactggctg   300
aacgggaagg agtacaagtg caaagtgtcg aacaaggccc tgccggctcc aattgaaaag    360
accatcagca aggccaaggg ccagccaagg gaaccacagg tgtacaccct ccctccttcc    420
cgggacgagc tgaccaaaaa ccaagtgtcc ctgacttgcc ttgtgaaggg gttctaccct    480
tctgacattg ccgtcgaatg ggaatcgaac ggacagcctg aaaacaacta taagactacc    540
ccgcccgtgc tggattccga cggaagcttc ttcctgtact ccaagctgac cgtggacaag    600
tcgagatggc agcagggaaa tgtgttcagc tgctccgtga tgcatgaggc gctgcacaac    660
cactacaccc agaagtcact gagcctctcc cccggaaaga tcgaaggacg cttcttaaac    720
tcattattca accaagaagt tcaaattccc ttgaccgaaa gttactgtgg cccatgtcct    780
aaaaactgga tatgttacaa aaataactgc taccaatttt ttgatgagag taaaaactgg    840
tatgagagcc aggcttcttg tatgtctcaa aatgccagcc ttctgaaagt atacagcaaa    900
gaggaccagg atttacttaa actggtgaag tcattccatt ggatgggact agtacacatt    960
ccaacaaatg gatcttggca gtgggaagat ggctccattc tctcacccaa cctactaaca   1020
ataattgaaa tgcagaaggg agactgtgca ctctatgcct cgagctttaa aggcttcata   1080
gaaaactgtt caactccaaa tacatacatc tgcatgcaaa ggactgtg              1128
```

<210> SEQ ID NO 135
<211> LENGTH: 107
<212> TYPE: PRT
<213> ORGANISM: Artificial sequence
<220> FEATURE:
<223> OTHER INFORMATION: Synthetic peptide human kappa light chain

<400> SEQUENCE: 135

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                     85                  90                  95

Pro Val Thr Lys Ser Phe Asn Arg Gly Glu Cys
                100                 105

<210> SEQ ID NO 136
<211> LENGTH: 330
<212> TYPE: PRT
<213> ORGANISM: Artificial sequence
<220> FEATURE:
<223> OTHER INFORMATION: Synthetic peptide human IgG1 heavy chain
      CH1-CH2-CH3 D265A/N297A

<400> SEQUENCE: 136

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 137
<211> LENGTH: 450
<212> TYPE: PRT
<213> ORGANISM: Artificial sequence
<220> FEATURE:
<223> OTHER INFORMATION: Synthetic peptide trastuzumab heavy chain

<400> SEQUENCE: 137

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 138
<211> LENGTH: 213
<212> TYPE: PRT
<213> ORGANISM: Artificial sequence
<220> FEATURE:
<223> OTHER INFORMATION: Synthetic peptide trastuzumab light chain

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 139
```

-continued

```
<211> LENGTH: 451
<212> TYPE: PRT
<213> ORGANISM: Artificial sequence
<220> FEATURE:
<223> OTHER INFORMATION: Synthetic peptide rituximab heavy chain

<400> SEQUENCE: 139
```

| | | | | | | | | | | | | | | | |
|---|---|---|---|---|---|---|---|---|---|---|---|---|---|---|---|
| Gln | Val | Gln | Leu | Gln | Gln | Pro | Gly | Ala | Glu | Leu | Val | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Asn | Met | His | Trp | Val | Lys | Gln | Thr | Pro | Gly | Arg | Gly | Leu | Glu | Trp | Ile |
| | | 35 | | | | | 40 | | | | | 45 | | | |
| Gly | Ala | Ile | Tyr | Pro | Gly | Asn | Gly | Asp | Thr | Ser | Tyr | Asn | Gln | Lys | Phe |
| | 50 | | | | | 55 | | | | | 60 | | | | |
| Lys | Gly | Lys | Ala | Thr | Leu | Thr | Ala | Asp | Lys | Ser | Ser | Ser | Thr | Ala | Tyr |
| 65 | | | | | 70 | | | | | 75 | | | | | 80 |
| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |
| Ala | Arg | Ser | Thr | Tyr | Tyr | Gly | Gly | Asp | Trp | Tyr | Phe | Asn | Val | Trp | Gly |
| | | | 100 | | | | | 105 | | | | | 110 | | |
| Ala | Gly | Thr | Thr | Val | Thr | Val | Ser | Ala | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | | 180 | | | | | 185 | | | | | 190 | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Lys | Lys | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Leu | Leu | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Asp | Glu | Leu | Thr | Lys | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | 370 | | | | | 375 | | | | | 380 | | | | |

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 140
<211> LENGTH: 212
<212> TYPE: PRT
<213> ORGANISM: Artificial sequence
<220> FEATURE:
<223> OTHER INFORMATION: Synthetic peptide rituximab light chain

<400> SEQUENCE: 140

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 141
<211> LENGTH: 404
<212> TYPE: PRT
<213> ORGANISM: Artificial sequence
<220> FEATURE:
<223> OTHER INFORMATION: Synthetic peptide rituximab LC_ULBP2.wt

<400> SEQUENCE: 141

Gln Ile Val Leu Ser Gln Ser Pro Ala Ile Leu Ser Ala Ser Pro Gly

```
  1               5                    10                   15
Glu Lys Val Thr Met Thr Cys Arg Ala Ser Ser Val Ser Tyr Ile
             20                  25                  30
His Trp Phe Gln Gln Lys Pro Gly Ser Ser Pro Lys Pro Trp Ile Tyr
             35                  40                  45
Ala Thr Ser Asn Leu Ala Ser Gly Val Pro Val Arg Phe Ser Gly Ser
        50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                 85                  90                  95
Phe Gly Gly Gly Thr Lys Leu Glu Ile Lys Arg Thr Val Ala Ala Pro
                100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
            195                 200                 205
Asn Arg Gly Glu Cys Ala Pro Thr Ser Ser Ser Gly Gly Gly Gly Ser
        210                 215                 220
Glu Pro His Ser Leu Ser Tyr Asp Ile Thr Val Ile Pro Lys Phe Arg
225                 230                 235                 240
Pro Gly Pro Arg Trp Cys Ala Val Gln Gly Gln Val Asp Glu Lys Thr
                245                 250                 255
Phe Leu His Tyr Asp Cys Gly Asn Lys Thr Val Thr Pro Val Ser Pro
                260                 265                 270
Leu Gly Lys Lys Leu Asn Val Thr Thr Ala Trp Lys Ala Gln Asn Pro
        275                 280                 285
Val Leu Arg Glu Val Val Asp Ile Leu Thr Glu Gln Leu Arg Asp Ile
        290                 295                 300
Gln Leu Glu Asn Tyr Thr Pro Lys Glu Pro Leu Thr Leu Gln Ala Arg
305                 310                 315                 320
Met Ser Cys Glu Gln Lys Ala Glu Gly His Ser Ser Gly Ser Trp Gln
                325                 330                 335
Phe Ser Phe Asp Gly Gln Ile Phe Leu Leu Phe Asp Ser Glu Lys Arg
                340                 345                 350
Met Trp Thr Thr Val His Pro Gly Ala Arg Lys Met Lys Glu Lys Trp
            355                 360                 365
Glu Asn Asp Lys Val Val Ala Met Ser Phe His Tyr Phe Ser Met Gly
        370                 375                 380
Asp Cys Ile Gly Trp Leu Glu Asp Phe Leu Met Gly Met Asp Ser Thr
385                 390                 395                 400
Leu Glu Pro Ser

<210> SEQ ID NO 142
<211> LENGTH: 187
```

<212> TYPE: PRT
<213> ORGANISM: Artificial sequence
<220> FEATURE:
<223> OTHER INFORMATION: Synthetic peptide ULPB2 alpha1-alpha2 variant R80W

<400> SEQUENCE: 142

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
130                 135                 140

Glu Asn Asp Lys Val Val Ala Met Ser Phe His Tyr Phe Ser Met Gly
145                 150                 155                 160

Asp Cys Ile Gly Trp Leu Glu Asp Phe Leu Met Gly Met Asp Ser Thr
                165                 170                 175

Leu Glu Pro Ser Ala Gly Ala Pro Pro Met Val
            180                 185

<210> SEQ ID NO 143
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant ULBP2.C

<400> SEQUENCE: 143

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
130                 135                 140

Glu Asn Asp Lys Val Val Ala Thr Ile Leu Trp Gln Thr Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 144
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.C

<400> SEQUENCE: 144
gagccccata gtctgagcta cgacatcaca gttattccca gttcaggcc cggaccgcgc      60 tggtgtgccg tgcaaggaca gtcgacgaa aaaacctttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa agaaatgtgg actacagttc accccggtgc cgtaaaatg    420 aaggagaagt gggaaaacga caaagtggtg gcgactattc tgtggcagac ttcgatggga    480
gactgcatcg gttggctgga agatttcctc atgggtatgg actccacttt ggagccatcg    540

<210> SEQ ID NO 145
<211> LENGTH: 180
<212> TYPE: PRT
<213> ORGANISM: Artificial sequence
<220> FEATURE:
<223> OTHER INFORMATION: Synthetic peptide, ULBP alpha1-alpha2 variant
      ULBP2.R

<400> SEQUENCE: 145

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
130                 135                 140

Glu Asn Asp Lys Val Val Ala Thr Leu Leu Trp Gly Trp Ser Met Gly
145                 150                 155                 160

Asp Cys Ile Gly Trp Leu Glu Asp Phe Leu Met Gly Met Asp Ser Thr
            165                 170                 175

Leu Glu Pro Ser
            180

<210> SEQ ID NO 146
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.R

<400> SEQUENCE: 146
gagccccata gtctgagcta cgacatcaca gttattccca agttcaggcc cggaccgcgc     60
tggtgtgccg tgcaaggaca gtcgacgaa aaaaccttc ttcattacga ttgcggaaat     120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc cgtaaaatg    420 aaggagaagt gggaaaacga caaagtggtg gcgactttgt tgtggggtg gtcgatggga    480 gactgcatcg gttggctgga agatttcctc atgggtatgg actccacttt ggagccatcg    540

<210> SEQ ID NO 147
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.AA

<400> SEQUENCE: 147

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Met Phe Trp Ser Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 148
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AA

<400> SEQUENCE: 148 gagcccata gtctgagcta cgacatcaca gttattccca gttcaggcc cggaccgcgc      60 tggtgtgccg tgcaaggaca gtcgacgaa aaaacctttc ttcattacga ttgcggaaat    120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactatgt tttggagttg gtcgatggga    480
gactgcatcg gttggctgga agatttcctc atgggtatgg actccacttt ggagccatcg    540

<210> SEQ ID NO 149
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.AB

<400> SEQUENCE: 149

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Leu Met Trp Gln Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 150
<211> LENGTH: 540
<212> TYPE: DNA
<213> ORGANISM: Artificial sequence
<220> FEATURE:
<223> OTHER INFORMATION: Synthetic polynucleotide, encoding ULBP2
      alpha1-alpha2 variant ULBP2.AB

<400> SEQUENCE: 150
gagccccata gtctgagcta cgacatcaca gttattccca agttcaggcc cggaccgcgc    60
tggtgtgccg tgcaaggaca gtcgacgaa aaaacctttc ttcattacga ttgcggaaat    120
aagactgtaa cgccagtctc tcctttaggt aagaagttaa acgtcactac ggcgtggaag    180
gcacaaaacc ccgtcctgcg cgaggtcgtc gacatcctga ctgaacaatt gtgggacatc    240
cagctcgaga attacactcc aaaggagcct cttaccctgc aggctagaat gtcttgcgag    300
caaaaggcag agggccactc ctccggcagc tggcagttca gtttcgacgg acaaatcttt    360
ctgttattcg attcagagaa gagaatgtgg actacagttc accccggtgc ccgtaaaatg    420
aaggagaagt gggaaaacga caaagtggtg gcgactctta tgtggcagtg gtcgatggga    480
gactgcatcg gttggctgga agatttcctc atgggtatgg actccacttt ggagccatcg    540

<210> SEQ ID NO 151
<211> LENGTH: 180
<212> TYPE: PRT
<213> ORGANISM: Artificial sequence
<220> FEATURE:
<223> OTHER INFORMATION: Synthetic peptide, ULBP2 alpha1-alpha2 variant
      ULBP2.S3

<400> SEQUENCE: 151

Glu Pro His Ser Leu Ser Tyr Asp Ile Thr Val Ile Pro Lys Phe Arg
1               5                   10                  15

Pro Gly Pro Arg Trp Cys Ala Val Gln Gly Gln Val Asp Glu Lys Thr
            20                  25                  30

Phe Leu His Tyr Asp Cys Gly Asn Lys Thr Val Thr Pro Val Ser Pro
        35                  40                  45

Leu Gly Lys Lys Leu Asn Val Thr Thr Ala Trp Lys Ala Gln Asn Pro
    50                  55                  60

Val Leu Arg Glu Val Val Asp Ile Leu Thr Glu Gln Leu Trp Asp Ile
65                  70                  75                  80

Gln Leu Glu Asn Tyr Thr Pro Lys Glu Pro Leu Thr Leu Gln Ala Arg
                85                  90                  95

Met Ser Cys Glu Gln Lys Ala Glu Gly His Ser Ser Gly Ser Trp Gln
            100                 105                 110

Phe Ser Phe Asp Gly Gln Ile Phe Leu Leu Phe Asp Ser Glu Lys Arg
        115                 120                 125

Met Trp Thr Thr Val His Pro Gly Ala Arg Lys Met Lys Glu Lys Trp
    130                 135                 140

Glu Asn Asp Lys Val Val Ala Thr Lys Leu Tyr Leu Trp Ser Met Gly
145                 150                 155                 160

Asp Cys Ile Gly Trp Leu Glu Asp Phe Leu Met Gly Met Asp Ser Thr
                165                 170                 175

Leu Glu Pro Ser
            180

<210> SEQ ID NO 152
<211> LENGTH: 404
<212> TYPE: PRT
<213> ORGANISM: Artificial sequence
<220> FEATURE:
<223> OTHER INFORMATION: Synthetic peptide rituximab LC_ULBP2.S3

<400> SEQUENCE: 152

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ala Pro Thr Ser Ser Gly Gly Gly Gly Ser
    210                 215                 220

Glu Pro His Ser Leu Ser Tyr Asp Ile Thr Val Ile Pro Lys Phe Arg
225                 230                 235                 240

Pro Gly Pro Arg Trp Cys Ala Val Gln Gly Gln Val Asp Glu Lys Thr
                245                 250                 255

Phe Leu His Tyr Asp Cys Gly Asn Lys Thr Val Thr Pro Val Ser Pro
            260                 265                 270

Leu Gly Lys Lys Leu Asn Val Thr Thr Ala Trp Lys Ala Gln Asn Pro
        275                 280                 285

Val Leu Arg Glu Val Val Asp Ile Leu Thr Glu Gln Leu Trp Asp Ile
    290                 295                 300

Gln Leu Glu Asn Tyr Thr Pro Lys Glu Pro Leu Thr Leu Gln Ala Arg
305                 310                 315                 320

Met Ser Cys Glu Gln Lys Ala Glu Gly His Ser Ser Gly Ser Trp Gln
                325                 330                 335

Phe Ser Phe Asp Gly Gln Ile Phe Leu Leu Phe Asp Ser Glu Lys Arg
            340                 345                 350

Met Trp Thr Thr Val His Pro Gly Ala Arg Lys Met Lys Glu Lys Trp
        355                 360                 365
```

```
Glu Asn Asp Lys Val Val Ala Thr Lys Leu Tyr Leu Trp Ser Met Gly
    370                 375                 380

Asp Cys Ile Gly Trp Leu Glu Asp Phe Leu Met Gly Met Asp Ser Thr
385                 390                 395                 400

Leu Glu Pro Ser

<210> SEQ ID NO 153
<211> LENGTH: 634
<212> TYPE: PRT
<213> ORGANISM: Artificial sequence
<220> FEATURE:
<223> OTHER INFORMATION: Synthetic peptide rituximab HC_ULBP2.R80W

<400> SEQUENCE: 153

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                     325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Gly Gly Gly Ser Glu Pro His Ser Leu Ser Tyr Asp Ile Thr
    450                 455                 460
Val Ile Pro Lys Phe Arg Pro Gly Pro Arg Trp Cys Ala Val Gln Gly
465                 470                 475                 480
Gln Val Asp Glu Lys Thr Phe Leu His Tyr Asp Cys Gly Asn Lys Thr
                485                 490                 495
Val Thr Pro Val Ser Pro Leu Gly Lys Lys Leu Asn Val Thr Thr Ala
            500                 505                 510
Trp Lys Ala Gln Asn Pro Val Leu Arg Glu Val Val Asp Ile Leu Thr
        515                 520                 525
Glu Gln Leu Trp Asp Ile Gln Leu Glu Asn Tyr Thr Pro Lys Glu Pro
    530                 535                 540
Leu Thr Leu Gln Ala Arg Met Ser Cys Glu Gln Lys Ala Glu Gly His
545                 550                 555                 560
Ser Ser Gly Ser Trp Gln Phe Ser Phe Asp Gly Gln Ile Phe Leu Leu
                565                 570                 575
Phe Asp Ser Glu Lys Arg Met Trp Thr Thr Val His Pro Gly Ala Arg
            580                 585                 590
Lys Met Lys Glu Lys Trp Glu Asn Asp Lys Val Val Ala Met Ser Phe
        595                 600                 605
His Tyr Phe Ser Met Gly Asp Cys Ile Gly Trp Leu Glu Asp Phe Leu
    610                 615                 620
Met Gly Met Asp Ser Thr Leu Glu Pro Ser
625                 630
```

<210> SEQ ID NO 154
<211> LENGTH: 156
<212> TYPE: PRT
<213> ORGANISM: Artificial sequence
<220> FEATURE:
<223> OTHER INFORMATION: Synthetic peptide NKG2D.AF ectodomain

<400> SEQUENCE: 154

```
Met Ala Leu Pro Val Thr Ala Leu Leu Leu Pro Leu Ala Leu Leu Leu
1               5                   10                  15
His Ala Ala Arg Pro Leu Phe Asn Gln Glu Val Gln Ile Pro Leu Thr
                20                  25                  30
Glu Ser Tyr Cys Gly Pro Cys Pro Lys Asn Trp Ile Cys Tyr Lys Asn
            35                  40                  45
Asn Cys Tyr Gln Phe Phe Asp Glu Ser Lys Asn Trp Tyr Glu Ser Gln
```

```
                                   50                  55                  60
Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Ala His Trp Met Gly
                     85                  90                  95

Leu Val His Ile Pro Thr Asn Gly Ser Trp Gln Trp Glu Asp Gly Ser
                    100                 105                 110

Ile Leu Ser Pro Asn Leu Leu Thr Ile Ile Glu Met Gln Lys Gly Asp
                115                 120                 125

Cys Ala Leu Tyr Ala Ser Ser Phe Lys Gly Phe Ile Glu Asn Cys Ser
130                 135                 140

Thr Pro Asn Thr Tyr Ile Cys Met Gln Arg Thr Val
145                 150                 155

<210> SEQ ID NO 155
<211> LENGTH: 629
<212> TYPE: PRT
<213> ORGANISM: Artificial sequence
<220> FEATURE:
<223> OTHER INFORMATION: Synthetic peptide
      NKG2D.wt_CD8hingeTM_4-1BB_CD3zeta_EGFP complete chimeric antigen
      receptor

<400> SEQUENCE: 155

Met Ala Leu Pro Val Thr Ala Leu Leu Leu Pro Leu Ala Leu Leu Leu
 1               5                  10                  15

His Ala Ala Arg Pro Leu Phe Asn Gln Glu Val Gln Ile Pro Leu Thr
                 20                  25                  30

Glu Ser Tyr Cys Gly Pro Cys Pro Lys Asn Trp Ile Cys Tyr Lys Asn
             35                  40                  45

Asn Cys Tyr Gln Phe Phe Asp Glu Ser Lys Asn Trp Tyr Glu Ser Gln
 50                  55                  60

Ala Ser Cys Met Ser Gln Asn Ala Ser Leu Leu Lys Val Tyr Ser Lys
 65                  70                  75                  80

Glu Asp Gln Asp Leu Leu Lys Leu Val Lys Ser Tyr His Trp Met Gly
                 85                  90                  95

Leu Val His Ile Pro Thr Asn Gly Ser Trp Gln Trp Glu Asp Gly Ser
                100                 105                 110

Ile Leu Ser Pro Asn Leu Leu Thr Ile Ile Glu Met Gln Lys Gly Asp
                115                 120                 125

Cys Ala Leu Tyr Ala Ser Ser Phe Lys Gly Tyr Ile Glu Asn Cys Ser
130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255
```

Cys Arg Phe Pro Glu Glu Glu Gly Gly Cys Glu Leu Arg Val Lys
                260                 265                 270

Phe Ser Arg Ser Ala Asp Ala Pro Ala Tyr Lys Gln Gly Gln Asn Gln
            275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
    355                 360                 365

Thr Tyr Asp Ala Leu His Met Gln Ala Leu Pro Pro Arg Ser Gly Ser
370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
    435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
    515                 520                 525

Gly His Lys Leu Glu Tyr Asn Tyr Asn Ser His Asn Val Tyr Ile Met
530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
    595                 600                 605

Met Val Leu Leu Glu Phe Val Thr Ala Ala Gly Ile Thr Leu Gly Met
610                 615                 620

Asp Glu Leu Tyr Lys
625

<210> SEQ ID NO 156
<211> LENGTH: 1887
<212> TYPE: DNA
<213> ORGANISM: Artificial sequence
<220> FEATURE:

<223> OTHER INFORMATION: Synthetic polynucleotide, encoding
NKG2D.wt_CD8hingeTM_4-1BB_CD3zeta_EGFP complete chimeric antigen
receptor

<400> SEQUENCE: 156

| | | | | | |
|---|---|---|---|---|---|
| atggcattgc | ctgttacagc | tctgctgctg | cccctggctc | tgcttctgca | tgctgccaga | 60 |
| cctctgttca | atcaagaggt | gcagatccct | ctgaccgaga | gctactgtgg | ccctgtcct | 120 |
| aagaactgga | tctgctacaa | gaacaactgc | taccagttct | tcgacgagag | caagaattgg | 180 |
| tacgagagcc | aggccagctg | catgagccag | aatgccagcc | tgctgaaggt | gtacagcaaa | 240 |
| gaggaccagg | atctgctgaa | gctggtcaag | agctaccact | ggatgggact | cgtgcacatc | 300 |
| cctacaaacg | gcagctggca | gtgggaggac | ggctctatcc | tgtctcctaa | cctgctgacc | 360 |
| atcatcgaga | tgcagaaggg | cgactgcgcc | ctgtacgcca | gcagctttaa | gggctacatc | 420 |
| gagaactgca | gcacccctaa | cacctacatc | tgtatgcagc | ggaccgtgac | caccacacca | 480 |
| gctcctagac | ctccaactcc | tgctcctaca | atcgccagcc | agcctctgtc | tctgaggcca | 540 |
| gaagcttgta | gacctgctgc | aggcggagcc | gtgcatacaa | gaggactgga | tttcgcctgc | 600 |
| gacatctaca | tctgggcccc | tctggctgga | acatgtggcg | tgctgctgct | gagcctggtc | 660 |
| atcaccctgt | actgcagcct | gaagcggggc | agaaagaagc | tgctgtacat | ctttaagcag | 720 |
| cccttcatgc | ggcccgtgca | gaccacacaa | gaggaagatg | gctgctcctg | cagattcccc | 780 |
| gaggaagaag | aaggcggctg | cgagctgaga | gtgaagttca | gccgttctgc | cgacgctccc | 840 |
| gcctataagc | agggacagaa | ccagctgtac | aacgagctga | acctggggag | aagagaagag | 900 |
| tacgacgtgc | tggacaagcg | agagggcaga | gatcctgaga | tgggcggcaa | gcccagacgg | 960 |
| aagaatcctc | aagagggcct | gtataatgag | ctgcagaaag | acaagatggc | cgaggcctac | 1020 |
| agcgagatcg | gaatgaaggg | cgagcgcaga | agaggcaagg | acacgatgg | actgtaccag | 1080 |
| ggcctgagca | ccgccaccaa | ggatacctat | gatgccctgc | acatgcaggc | cctgcctcca | 1140 |
| agatcaggct | ctggttctgg | cagcggcagc | atggtgtcta | aaggcgagga | actgttcacc | 1200 |
| ggcgtggtgc | ccattctggt | ggaactggac | ggggatgtga | acggccacaa | gtttagcgtt | 1260 |
| agcggcgaag | gcgaagggga | tgccacatac | ggaaagctga | ccctgaagtt | catctgcacc | 1320 |
| accggcaagc | tgcctgtgcc | ttggcctaca | ctggtcacca | cactgacata | cggcgtgcag | 1380 |
| tgctttagca | gatacccga | ccatatgaag | cagcacgact | tcttcaagtc | cgccatgcct | 1440 |
| gagggctacg | tgcaagagcg | gaccatcttc | tttaaggacg | acggcaacta | caagaccagg | 1500 |
| gccgaagtga | agtttgaggg | cgacacccct | gtcaaccgga | tcgagctgaa | gggcatcgac | 1560 |
| ttcaaagagg | atggcaacat | cctgggccac | aagctcgagt | acaactacaa | cagccacaac | 1620 |
| gtgtacatca | tggccgacaa | gcagaagaac | ggcatcaagg | ccaacttcaa | gatccggcac | 1680 |
| aacatcgagg | acggcagcgt | tcagctggcc | gatcactacc | agcagaacac | ccctatcgga | 1740 |
| gatgcccctg | tgctgctccc | cgacaatcac | tacctgagca | cacagagcgc | cctgagcaag | 1800 |
| gaccccaacg | agaagaggga | tcacatggtg | ctgctggaat | ttgtgaccgc | cgcaggcatc | 1860 |
| accctcggca | tggacgaact | gtacaaa | | | 1887 |

<210> SEQ ID NO 157
<211> LENGTH: 629
<212> TYPE: PRT
<213> ORGANISM: Artificial sequence
<220> FEATURE:
<223> OTHER INFORMATION: Synthetic peptide
NKG2D.YA_CD8hingeTM_4-1BB_CD3zeta_EGFP complete chimeric antigen
receptor

<400> SEQUENCE: 157

Met Ala Leu Pro Val Thr Ala Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
    130                 135                 140

Thr Pro Asn Thr Tyr Ile Cys Met Gln Arg Thr Val Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
        195                 200                 205

Ala Gly Thr Cys Gly Val Leu Leu Leu Ser Leu Val Ile Thr Leu Tyr
    210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
                245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
        275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
                325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
        355                 360                 365

Thr Tyr Asp Ala Leu His Met Gln Ala Leu Pro Pro Arg Ser Gly Ser
    370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His

```
                    405                 410                 415
Lys Phe Ser Val Ser Gly Glu Gly Glu Gly Asp Ala Thr Tyr Gly Lys
                420                 425                 430

Leu Thr Leu Lys Phe Ile Cys Thr Thr Gly Lys Leu Pro Val Pro Trp
            435                 440                 445

Pro Thr Leu Val Thr Thr Leu Thr Tyr Gly Val Gln Cys Phe Ser Arg
        450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn Tyr Asn Ser His Asn Val Tyr Ile Met
530                 535                 540

Ala Asp Lys Gln Lys Asn Gly Ile Lys Ala Asn Phe Lys Ile Arg His
545                 550                 555                 560

Asn Ile Glu Asp Gly Ser Val Gln Leu Ala Asp His Tyr Gln Gln Asn
                565                 570                 575

Thr Pro Ile Gly Asp Gly Pro Val Leu Leu Pro Asp Asn His Tyr Leu
            580                 585                 590

Ser Thr Gln Ser Ala Leu Ser Lys Asp Pro Asn Glu Lys Arg Asp His
        595                 600                 605

Met Val Leu Leu Glu Phe Val Thr Ala Ala Gly Ile Thr Leu Gly Met
    610                 615                 620

Asp Glu Leu Tyr Lys
625

<210> SEQ ID NO 158
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.YA_CD8hingeTM_4-1BB_CD3zeta_EGFP complete chimeric antigen
      receptor

<400> SEQUENCE: 158
atggcattgc ctgttacagc tctgctgctg cccctggctc tgcttctgca tgctgccaga      60
cctctgttca atcaagaggt gcagatccct ctgaccgaga gctactgtgg ccctgtcct     120 aagaactgga tctgctacaa gaacaactgc taccagttct tcgacgagag caagaattgg    180
tacgagagcc aggccagctg catgagccag aatgccagct gctgaaggt gtacagcaaa     240 gaggaccagg atctgctgaa gctggtcaag agcgcccact ggatgggact cgtgcacatc    300
cctacaaacg gcagctggca gtgggaggac ggctctatcc tgtctcctaa cctgctgacc    360
atcatcgaga tgcagaaggg cgactgcgcc ctgtacgcca gcagctttaa gggctacatc    420
gagaactgca gcacccctaa cacctacatc tgtatgcagc ggaccgtgac caccacacca    480
gctcctagac ctccaactcc tgctcctaca atcgccagcc agcctctgtc tctgaggcca    540
gaagcttgta gacctgctgc aggcggagcc gtgcatacaa gaggactgga tttcgcctgc    600
gacatctaca tctgggcccc tctggctgga acatgtggcg tgctgctgct gagcctggtc    660
atcaccctgt actgcagcct gaagcggggc agaaagaagc tgctgtacat ctttaagcag    720
```

```
cccttcatgc ggcccgtgca gaccacacaa gaggaagatg gctgctcctg cagattcccc      780
gaggaagaag aaggcggctg cgagctgaga gtgaagttca gccgttctgc cgacgctccc      840
gcctataagc agggacagaa ccagctgtac aacgagctga acctggggag aagagaagag      900
tacgacgtgc tggacaagcg gagaggcaga gatcctgaga tgggcggcaa gcccagacgg      960
aagaatcctc aagagggcct gtataatgag ctgcagaaag acaagatggc cgaggcctac     1020
agcgagatcg gaatgaaggg cgagcgcaga gagggcaagg acacgatggt actgtaccag     1080
ggcctgagca ccgccaccaa ggatacctat gatgccctgc acatgcaggc cctgcctcca     1140
agatcaggct ctggttctgg cagcggcagc atggtgtcta aaggcgagga actgttcacc     1200
ggcgtggtgc ccattctggt ggaactggac ggggatgtga acggccacaa gtttagcgtt     1260
agcggcgaag gcgaagggga tgccacatac ggaaagctga ccctgaagtt catctgcacc     1320
accggcaagc tgcctgtgcc ttggcctaca ctggtcacca cactgacata cggcgtgcag     1380
tgctttagca gataccccga ccatatgaag cagcacgact tcttcaagtc cgccatgcct     1440
gagggctacg tgcaagagcg gaccatcttc tttaaggacg acggcaacta caagaccagg     1500
gccgaagtga agtttgaggg cgacaccctg gtcaaccgga tcgagctgaa gggcatcgac     1560
ttcaaagagg atggcaacat cctgggccac aagctcgagt acaactacaa cagccacaac     1620
gtgtacatca tggccgacaa gcagaagaac ggcatcaagg ccaacttcaa gatccggcac     1680
aacatcgagg acggcagcgt tcagctggcc gatcactacc agcagaacac ccctatcgga     1740
gatggccctg tgctgctccc cgacaatcac tacctgagca cacagagcgc cctgagcaag     1800
gaccccaacg agaagaggga tcacatggtg ctgctggaat ttgtgaccgc cgcaggcatc     1860
accctcggca tggacgaact gtacaaa                                          1887
```

<210> SEQ ID NO 159
<211> LENGTH: 629
<212> TYPE: PRT
<213> ORGANISM: Artificial sequence
<220> FEATURE:
<223> OTHER INFORMATION: Synthetic peptide
      NKG2D.AF_CD8hingeTM_4-1BB_CD3zeta_EGFP complete chimeric antigen
      receptor

<400> SEQUENCE: 159

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Ala His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Phe Ile Glu Asn Cys Ser
    130                 135                 140
```

```
Thr Pro Asn Thr Tyr Ile Cys Met Gln Arg Thr Val Thr Thr Pro
145                 150                 155                 160

Ala Pro Arg Pro Pro Thr Pro Ala Pro Thr Ile Ala Ser Gln Pro Leu
            165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Leu Ser Leu Val Ile Thr Leu Tyr
210                 215                 220

Cys Ser Leu Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
            245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Lys Gln Gly Gln Asn Gln
            275                 280                 285

Leu Tyr Asn Glu Leu Asn Leu Gly Arg Arg Glu Glu Tyr Asp Val Leu
290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
            325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
            355                 360                 365

Thr Tyr Asp Ala Leu His Met Gln Ala Leu Pro Pro Arg Ser Gly Ser
370                 375                 380

Gly Ser Gly Ser Gly Ser Met Val Ser Lys Gly Glu Glu Leu Phe Thr
385                 390                 395                 400

Gly Val Val Pro Ile Leu Val Glu Leu Asp Gly Asp Val Asn Gly His
            405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
            435                 440                 445

Pro Thr Leu Val Thr Thr Leu Thr Tyr Gly Val Gln Cys Phe Ser Arg
450                 455                 460

Tyr Pro Asp His Met Lys Gln His Asp Phe Phe Lys Ser Ala Met Pro
465                 470                 475                 480

Glu Gly Tyr Val Gln Glu Arg Thr Ile Phe Phe Lys Asp Asp Gly Asn
            485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
            515                 520                 525

Gly His Lys Leu Glu Tyr Asn Tyr Asn Ser His Asn Val Tyr Ile Met
            530                 535                 540

Ala Asp Lys Gln Lys Asn Gly Ile Lys Ala Asn Phe Lys Ile Arg His
545                 550                 555                 560
```

```
Asn Ile Glu Asp Gly Ser Val Gln Leu Ala Asp His Tyr Gln Gln Asn
                565                 570                 575
Thr Pro Ile Gly Asp Gly Pro Val Leu Leu Pro Asp Asn His Tyr Leu
            580                 585                 590
Ser Thr Gln Ser Ala Leu Ser Lys Asp Pro Asn Glu Lys Arg Asp His
        595                 600                 605
Met Val Leu Leu Glu Phe Val Thr Ala Ala Gly Ile Thr Leu Gly Met
    610                 615                 620
Asp Glu Leu Tyr Lys
625

<210> SEQ ID NO 160
<211> LENGTH: 1887
<212> TYPE: DNA
<213> ORGANISM: Artificial sequence
<220> FEATURE:
<223> OTHER INFORMATION: Synthetic polynucleotide, encoding
      NKG2D.AF_CD8hingeTM_4-1BB_CD3zeta_EGFP complete chimeric antigen
      receptor

<400> SEQUENCE: 160
```

| | | |
|---|---|---|
| atggcattgc ctgttacagc tctgctgctg cccctggctc tgcttctgca tgctgccaga | 60 |
| cctctgttca atcaagaggt gcagatccct ctgaccgaga gctactgtgg ccctgtcct | 120 |
| aagaactgga tctgctacaa gaacaactgc taccagttct tcgacgagag caagaattgg | 180 |
| tacgagagcc aggccagctg catgagccag aatgccagcc tgctgaaggt gtacagcaaa | 240 |
| gaggaccagg atctgctgaa gctggtcaag agcgcccact ggatgggact cgtgcacatc | 300 |
| cctacaaacg gcagctggca gtgggaggac ggctctatcc tgtctcctaa cctgctgacc | 360 |
| atcatcgaga tgcagaaggg cgactgcgcc ctgtacgcca gcagctttaa gggcttcatc | 420 |
| gagaactgca gcacccctaa cacctacatc tgtatgcagc ggaccgtgac caccacacca | 480 |
| gctcctagac ctccaactcc tgctcctaca atcgccagcc agcctctgtc tctgaggcca | 540 |
| gaagcttgta gacctgctgc aggcggagcc gtgcatacaa gaggactgga tttcgcctgc | 600 |
| gacatctaca tctgggcccc tctggctgga acatgtggcg tgctgctgct gagcctggtc | 660 |
| atcaccctgt actgcagcct gaagcggggc agaaagaagc tgctgtacat ctttaagcag | 720 |
| cccttcatgc ggcccgtgca gaccacacaa gaggaagatg gctgctcctg cagattcccc | 780 |
| gaggaagaag aaggcggctg cgagctgaga gtgaagttca gccgttctgc cgacgctccc | 840 |
| gcctataagc agggacagaa ccagctgtac aacgagctga acctggggga agagaagag | 900 |
| tacgacgtgc tggacaagcg agagggcaga gatcctgaga tgggcggcaa gcccagacgg | 960 |
| aagaatcctc aagagggcct gtataatgag ctgcagaaag acaagatggc cgaggcctac | 1020 |
| agcgagatcg gaatgaaggg cgagcgcaga agaggcaagg acacgatgg actgtaccag | 1080 |
| ggcctgagca ccgccaccaa ggatacctat gatgccctgc acatgcaggc cctgcctcca | 1140 |
| agatcaggct ctggttctgg cagcggcagc atggtgtcta aggcgagga actgttcacc | 1200 |
| ggcgtggtgc ccattctggt ggaactggac ggggatgtga acggccacaa gtttagcgtt | 1260 |
| agcggcgaag gcgaagggga tgccacatac ggaaagctga ccctgaagtt catctgcacc | 1320 |
| accggcaagc tgcctgtgcc ttggcctaca ctggtcacca cactgacata cggcgtgcag | 1380 |
| tgctttagca gataccccga ccatatgaag cagcacgact tcttcaagtc cgccatgcct | 1440 |
| gagggctacg tgcaagagcg gaccatcttc tttaaggacg acggcaacta caagaccagg | 1500 |
| gccgaagtga agtttgaggg cgacaccctg gtcaaccgga tcgagctgaa gggcatcgac | 1560 |

```
ttcaaagagg atggcaacat cctgggccac aagctcgagt acaactacaa cagccacaac    1620
gtgtacatca tggccgacaa gcagaagaac ggcatcaagg ccaacttcaa gatccggcac    1680
aacatcgagg acggcagcgt tcagctggcc gatcactacc agcagaacac ccctatcgga    1740
gatggccctg tgctgctccc cgacaatcac tacctgagca cacagagcgc cctgagcaag    1800
gaccccaacg agaagaggga tcacatggtg ctgctggaat ttgtgaccgc cgcaggcatc    1860
accctcggca tggacgaact gtacaaa                                        1887
```

<210> SEQ ID NO 161
<211> LENGTH: 470
<212> TYPE: PRT
<213> ORGANISM: Artificial Sequence
<220> FEATURE:
<223> OTHER INFORMATION: Synthetic sequence, 3BNC60 H chain (IgG1 Fc
      with D265A/N297A (Kabat numbering) mutations)

<400> SEQUENCE: 161

```
Met Met Arg Pro Ile Val Leu Val Leu Leu Phe Ala Thr Ser Ala Leu
1               5                   10                  15

Ala Gln Val His Leu Ser Gln Ser Gly Ala Ala Val Thr Lys Pro Gly
            20                  25                  30

Ala Ser Val Arg Val Ser Cys Glu Ala Ser Gly Tyr Lys Ile Ser Asp
        35                  40                  45

His Phe Ile His Trp Trp Arg Gln Ala Pro Gly Gln Gly Leu Gln Trp
    50                  55                  60

Val Gly Trp Ile Asn Pro Lys Thr Gly Gln Pro Asn Asn Pro Arg Gln
65                  70                  75                  80

Phe Gln Gly Arg Val Ser Leu Thr Arg Gln Ala Ser Trp Asp Phe Asp
                85                  90                  95

Thr Tyr Ser Phe Tyr Met Asp Leu Lys Ala Val Arg Ser Asp Asp Thr
            100                 105                 110

Ala Ile Tyr Phe Cys Ala Arg Gln Arg Ser Asp Phe Trp Asp Phe Asp
        115                 120                 125

Val Trp Gly Ser Gly Thr Gln Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Ala
        275                 280                 285

Val Ser His Glu Asp Pro Glu Val Lys Phe Asn Trp Tyr Val Asp Gly
    290                 295                 300
```

Val Glu Val His Asn Ala Lys Thr Lys Pro Arg Glu Gln Tyr Ala
305                 310                 315                 320

Ser Thr Tyr Arg Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 162
<211> LENGTH: 414
<212> TYPE: PRT
<213> ORGANISM: Artificial Sequence
<220> FEATURE:
<223> OTHER INFORMATION: Synthetic sequence, 3BNC60 L chain (with
      appended ULBP2.S3)

<400> SEQUENCE: 162

Met Met Arg Pro Ile Val Leu Val Leu Leu Phe Ala Thr Ser Ala Leu
1               5                   10                  15

Ala Asp Ile Gln Met Thr Gln Ser Pro Ser Ser Leu Ser Ala Arg Val
            20                  25                  30

Gly Asp Thr Val Thr Ile Thr Cys Gln Ala Asn Gly Tyr Leu Asn Trp
        35                  40                  45

Tyr Gln Gln Arg Arg Gly Lys Ala Pro Lys Leu Leu Ile Tyr Asp Gly
    50                  55                  60

Ser Lys Leu Glu Arg Gly Val Pro Ala Arg Phe Ser Gly Arg Arg Trp
65                  70                  75                  80

Gly Gln Glu Tyr Asn Leu Thr Ile Asn Asn Leu Gln Pro Glu Asp Val
                85                  90                  95

Ala Thr Tyr Phe Cys Gln Val Tyr Glu Phe Ile Val Pro Gly Thr Arg
            100                 105                 110

Leu Asp Leu Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
            165                 170                 175

Ser Lys Asp Ser Thr Tyr Ser Leu Ser Ser Thr Leu Thr Leu Ser Lys 180                 185                 190
Ala Asp Tyr Glu Lys His Lys Val Tyr Ala Cys Glu Val Thr His Gln
            195                 200                 205
Gly Leu Ser Ser Pro Val Thr Lys Ser Phe Asn Arg Gly Glu Cys Ala
        210                 215                 220
Pro Thr Ser Ser Ser Gly Gly Gly Ser Glu Pro His Ser Leu Ser
225                 230                 235                 240
Tyr Asp Ile Thr Val Ile Pro Lys Phe Arg Pro Gly Pro Arg Trp Cys
                245                 250                 255
Ala Val Gln Gly Gln Val Asp Glu Lys Thr Phe Leu His Tyr Asp Cys
            260                 265                 270
Gly Asn Lys Thr Val Thr Pro Val Ser Pro Leu Gly Lys Lys Leu Asn
        275                 280                 285
Val Thr Thr Ala Trp Lys Ala Gln Asn Pro Val Leu Arg Glu Val Val
    290                 295                 300
Asp Ile Leu Thr Glu Gln Leu Trp Asp Ile Gln Leu Glu Asn Tyr Thr
305                 310                 315                 320
Pro Lys Glu Pro Leu Thr Leu Gln Ala Arg Met Ser Cys Glu Gln Lys
                325                 330                 335
Ala Glu Gly His Ser Ser Gly Ser Trp Gln Phe Ser Phe Asp Gly Gln
            340                 345                 350
Ile Phe Leu Leu Phe Asp Ser Glu Lys Arg Met Trp Thr Thr Val His
        355                 360                 365
Pro Gly Ala Arg Lys Met Lys Glu Lys Trp Glu Asn Asp Lys Val Val
    370                 375                 380
Ala Thr Lys Leu Tyr Leu Trp Ser Met Gly Asp Cys Ile Gly Trp Leu
385                 390                 395                 400
Glu Asp Phe Leu Met Gly Met Asp Ser Thr Leu Glu Pro Ser
                405                 410

<210> SEQ ID NO 163
<211> LENGTH: 470
<212> TYPE: PRT
<213> ORGANISM: Artificial Sequence
<220> FEATURE:
<223> OTHER INFORMATION: Synthetic sequence, 3BNC117 H chain (IgG1 Fc
      with D265A/N297A (Kabat numbering) mutations)

<400> SEQUENCE: 163

Met Met Arg Pro Ile Val Leu Val Leu Leu Phe Ala Thr Ser Ala Leu
1               5                   10                  15
Ala Gln Val Gln Leu Leu Gln Ser Gly Ala Ala Val Thr Lys Pro Gly
            20                  25                  30
Ala Ser Val Arg Val Ser Cys Glu Ala Ser Gly Tyr Asn Ile Arg Asp
        35                  40                  45
Tyr Phe Ile His Trp Trp Arg Gln Ala Pro Gly Gln Gly Leu Gln Trp
    50                  55                  60
Val Gly Trp Ile Asn Pro Lys Thr Gly Gln Pro Asn Asn Pro Arg Gln
65                  70                  75                  80
Phe Gln Gly Arg Val Ser Leu Thr Arg His Ala Ser Trp Asp Phe Asp
                85                  90                  95
Thr Tyr Ser Phe Tyr Met Asp Leu Lys Ala Leu Arg Ser Asp Asp Thr
            100                 105                 110
Ala Val Tyr Phe Cys Ala Arg Gln Arg Ser Asp Tyr Trp Asp Phe Asp
        115                 120                 125

Val Trp Gly Ser Gly Thr Gln Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Ala
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Ala
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 164
<211> LENGTH: 414
<212> TYPE: PRT
<213> ORGANISM: Artificial Sequence
<220> FEATURE:
<223> OTHER INFORMATION: Synthetic sequence, 3BNC117 L chain (with
      appended ULBP2.S3)

<400> SEQUENCE: 164

Met Met Arg Pro Ile Val Leu Val Leu Leu Phe Ala Thr Ser Ala Leu
1               5                   10                  15

Ala Asp Ile Gln Met Thr Gln Ser Pro Ser Ser Leu Ser Ala Ser Val
            20                  25                  30

Gly Asp Thr Val Thr Ile Thr Cys Gln Ala Asn Gly Tyr Leu Asn Trp
        35                  40                  45

Tyr Gln Gln Arg Arg Gly Lys Ala Pro Lys Leu Leu Ile Tyr Asp Gly
    50                  55                  60

Ser Lys Leu Glu Arg Gly Val Pro Ser Arg Phe Ser Gly Arg Arg Trp
65                  70                  75                  80

Gly Gln Glu Tyr Asn Leu Thr Ile Asn Asn Leu Gln Pro Glu Asp Ile
                85                  90                  95

Ala Thr Tyr Phe Cys Gln Val Tyr Glu Phe Val Val Pro Gly Thr Arg
            100                 105                 110

Leu Asp Leu Lys Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys Ala
    210                 215                 220

Pro Thr Ser Ser Ser Gly Gly Gly Ser Glu Pro His Ser Leu Ser
225                 230                 235                 240

Tyr Asp Ile Thr Val Ile Pro Lys Phe Arg Pro Gly Pro Arg Trp Cys
                245                 250                 255

Ala Val Gln Gly Gln Val Asp Glu Lys Thr Phe Leu His Tyr Asp Cys
            260                 265                 270

Gly Asn Lys Thr Val Thr Pro Val Ser Pro Leu Gly Lys Lys Leu Asn
        275                 280                 285

Val Thr Thr Ala Trp Lys Ala Gln Asn Pro Val Leu Arg Glu Val Val
290                 295                 300

Asp Ile Leu Thr Glu Gln Leu Trp Asp Ile Gln Leu Glu Asn Tyr Thr
305                 310                 315                 320

Pro Lys Glu Pro Leu Thr Leu Gln Ala Arg Met Ser Cys Glu Gln Lys
                325                 330                 335

Ala Glu Gly His Ser Ser Gly Ser Trp Gln Phe Ser Asp Gly Gln
            340                 345                 350

Ile Phe Leu Leu Phe Asp Ser Glu Lys Arg Met Trp Thr Thr Val His
        355                 360                 365

Pro Gly Ala Arg Lys Met Lys Glu Lys Trp Glu Asn Asp Lys Val Val
370                 375                 380

Ala Thr Lys Leu Tyr Leu Trp Ser Met Gly Asp Cys Ile Gly Trp Leu
385                 390                 395                 400

Glu Asp Phe Leu Met Gly Met Asp Ser Thr Leu Glu Pro Ser
                405                 410

<210> SEQ ID NO 165
<211> LENGTH: 479

<212> TYPE: PRT
<213> ORGANISM: Artificial Sequence
<220> FEATURE:
<223> OTHER INFORMATION: Synthetic sequence

<400> SEQUENCE: 165

Met Met Arg Pro Ile Val Leu Val Leu Leu Phe Ala Thr Ser Ala Leu
1               5                   10                  15

Ala Gln Met Gln Leu Gln Glu Ser Gly Pro Gly Leu Val Lys Pro Ser
            20                  25                  30

Glu Thr Leu Ser Leu Thr Cys Ser Val Ser Gly Ala Ser Ile Ser Asp
        35                  40                  45

Ser Tyr Trp Ser Trp Ile Arg Arg Ser Pro Gly Lys Gly Leu Glu Trp
    50                  55                  60

Ile Gly Tyr Val His Lys Ser Gly Asp Thr Asn Tyr Ser Pro Ser Leu
65                  70                  75                  80

Lys Ser Arg Val Asn Leu Ser Leu Asp Thr Ser Lys Asn Gln Val Ser
                85                  90                  95

Leu Ser Leu Val Ala Ala Thr Ala Ala Asp Ser Gly Lys Tyr Tyr Cys
            100                 105                 110

Ala Arg Thr Leu His Gly Arg Arg Ile Tyr Gly Ile Val Ala Phe Asn
        115                 120                 125

Glu Trp Phe Thr Tyr Phe Tyr Met Asp Val Trp Gly Asn Gly Thr Gln
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Ala Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Ala Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

```
Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475
```

<210> SEQ ID NO 166
<211> LENGTH: 420
<212> TYPE: PRT
<213> ORGANISM: Artificial Sequence
<220> FEATURE:
<223> OTHER INFORMATION: Synthetic sequence, PGT121 L chain (with appended ULBP2.S3)

<400> SEQUENCE: 166

```
Met Met Arg Pro Ile Val Leu Val Leu Leu Phe Ala Thr Ser Ala Leu
1               5                   10                  15

Ala Ser Asp Ile Ser Val Ala Pro Gly Glu Thr Ala Arg Ile Ser Cys
                20                  25                  30

Gly Glu Lys Ser Leu Gly Ser Arg Ala Val Gln Trp Tyr Gln His Arg
            35                  40                  45

Ala Gly Gln Ala Pro Ser Leu Ile Ile Tyr Asn Asn Gln Asp Arg Pro
        50                  55                  60

Ser Gly Ile Pro Glu Arg Phe Ser Gly Ser Pro Asp Ser Pro Phe Gly
65                  70                  75                  80

Thr Thr Ala Thr Leu Thr Ile Thr Ser Val Glu Ala Gly Asp Glu Ala
                85                  90                  95

Asp Tyr Tyr Cys His Ile Trp Asp Ser Arg Val Pro Thr Lys Trp Val
                100                 105                 110

Phe Gly Gly Gly Thr Thr Leu Thr Val Leu Arg Thr Val Ala Ala Pro
            115                 120                 125

Ser Val Phe Ile Phe Pro Pro Ser Asp Glu Gln Leu Lys Ser Gly Thr
        130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys Ala Pro Thr Ser Ser Ser Gly Gly Gly Gly Ser
225                 230                 235                 240

Glu Pro His Ser Leu Ser Tyr Asp Ile Thr Val Ile Pro Lys Phe Arg
                245                 250                 255

Pro Gly Pro Arg Trp Cys Ala Val Gln Gly Gln Val Asp Glu Lys Thr
            260                 265                 270
```

```
Phe Leu His Tyr Asp Cys Gly Asn Lys Thr Val Thr Pro Val Ser Pro
            275                 280                 285

Leu Gly Lys Lys Leu Asn Val Thr Thr Ala Trp Lys Ala Gln Asn Pro
        290                 295                 300

Val Leu Arg Glu Val Val Asp Ile Leu Thr Glu Gln Leu Trp Asp Ile
305                 310                 315                 320

Gln Leu Glu Asn Tyr Thr Pro Lys Gly Pro Leu Thr Leu Gln Ala Arg
                325                 330                 335

Met Ser Cys Glu Gln Lys Ala Glu Gly His Ser Ser Gly Ser Trp Gln
            340                 345                 350

Phe Ser Phe Asp Gly Gln Ile Phe Leu Leu Phe Asp Ser Glu Lys Arg
        355                 360                 365

Met Trp Thr Thr Val His Pro Gly Ala Arg Lys Met Lys Glu Lys Trp
370                 375                 380

Glu Asn Asp Lys Val Val Ala Thr Lys Leu Tyr Leu Trp Ser Met Gly
385                 390                 395                 400

Asp Cys Ile Gly Trp Leu Glu Asp Phe Leu Met Gly Met Asp Ser Thr
                405                 410                 415

Leu Glu Pro Ser
            420

<210> SEQ ID NO 167
<211> LENGTH: 479
<212> TYPE: PRT
<213> ORGANISM: Artificial Sequence
<220> FEATURE:
<223> OTHER INFORMATION: Synthetic sequence, 10-1074 H chain (IgG1 Fc
      with D265A/N297A (Kabat numbering) mutations)

<400> SEQUENCE: 167

Met Met Arg Pro Ile Val Leu Val Leu Leu Phe Ala Thr Ser Ala Leu
1               5                   10                  15

Ala Gln Val Gln Leu Gln Glu Ser Gly Pro Gly Leu Val Lys Pro Ser
            20                  25                  30

Glu Thr Leu Ser Val Thr Cys Ser Val Ser Gly Asp Ser Met Asn Asn
        35                  40                  45

Tyr Tyr Trp Thr Trp Ile Arg Gln Ser Pro Gly Lys Gly Leu Glu Trp
    50                  55                  60

Ile Gly Tyr Ile Ser Asp Arg Glu Ser Ala Thr Tyr Asn Pro Ser Leu
65                  70                  75                  80

Asn Ser Arg Val Val Ile Ser Arg Asp Thr Ser Lys Asn Gln Leu Ser
                85                  90                  95

Leu Lys Leu Asn Ser Val Thr Pro Ala Asp Thr Ala Val Tyr Tyr Cys
            100                 105                 110

Ala Thr Ala Arg Arg Gly Gln Arg Ile Tyr Gly Val Val Ser Phe Gly
        115                 120                 125

Glu Phe Phe Tyr Tyr Ser Met Asp Val Trp Gly Lys Gly Thr Thr
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
```

```
                     195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Ala Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Ala Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 168
<211> LENGTH: 428
<212> TYPE: PRT
<213> ORGANISM: Artificial Sequence
<220> FEATURE:
<223> OTHER INFORMATION: Synthetic sequence, 10-1074 L chain (with
      appended ULBP2.S3)

<400> SEQUENCE: 168

Met Met Arg Pro Ile Val Leu Val Leu Leu Phe Ala Thr Ser Ala Leu
1               5                   10                  15

Ala Ser Tyr Val Arg Pro Leu Ser Val Ala Leu Gly Glu Thr Ala Arg
                20                  25                  30

Ile Ser Cys Gly Arg Gln Ala Leu Gly Ser Arg Ala Val Gln Trp Tyr
            35                  40                  45

Gln His Arg Pro Gly Gln Ala Pro Ile Leu Leu Ile Tyr Asn Asn Gln
        50                  55                  60

Asp Arg Pro Ser Gly Ile Pro Glu Arg Phe Ser Gly Thr Pro Asp Ile
65                  70                  75                  80
```

-continued

```
Asn Phe Gly Thr Arg Ala Thr Leu Thr Ile Ser Gly Val Glu Ala Gly
                 85                  90                  95
Asp Glu Ala Asp Tyr Tyr Cys His Met Trp Asp Ser Arg Ser Gly Phe
            100                 105                 110
Ser Trp Ser Phe Gly Gly Ala Thr Arg Leu Thr Val Leu Arg Thr Val
        115                 120                 125
Ala Ala Pro Ser Val Phe Ile Phe Pro Pro Ser Asp Glu Gln Leu Lys
    130                 135                 140
Ser Gly Thr Ala Ser Val Val Cys Leu Leu Asn Asn Phe Tyr Pro Arg
145                 150                 155                 160
Glu Ala Lys Val Gln Trp Lys Val Asp Asn Ala Leu Gln Ser Gly Asn
                165                 170                 175
Ser Gln Glu Ser Val Thr Glu Gln Asp Ser Lys Asp Ser Thr Tyr Ser
            180                 185                 190
Leu Ser Ser Thr Leu Thr Leu Ser Lys Ala Asp Tyr Glu Lys His Lys
        195                 200                 205
Val Tyr Ala Cys Glu Val Thr His Gln Gly Leu Ser Ser Pro Val Thr
    210                 215                 220
Lys Ser Phe Asn Arg Gly Glu Cys Ala Pro Thr Ser Ser Ser Gly Gly
225                 230                 235                 240
Gly Gly Ser Glu Pro His Ser Leu Ser Tyr Asp Ile Thr Val Ile Pro
                245                 250                 255
Lys Phe Arg Pro Gly Pro Arg Trp Cys Ala Val Gln Gly Gln Val Asp
            260                 265                 270
Glu Lys Thr Phe Leu His Tyr Asp Cys Gly Asn Lys Thr Val Thr Pro
        275                 280                 285
Val Ser Pro Leu Gly Lys Lys Leu Asn Val Thr Thr Ala Trp Lys Ala
    290                 295                 300
Gln Asn Pro Val Leu Arg Glu Val Val Asp Ile Leu Thr Glu Gln Leu
305                 310                 315                 320
Trp Asp Ile Gln Leu Glu Asn Tyr Thr Pro Lys Glu Pro Leu Thr Leu
                325                 330                 335
Gln Ala Arg Met Ser Cys Glu Gln Lys Ala Glu Gly His Ser Ser Gly
            340                 345                 350
Ser Trp Gln Phe Ser Phe Asp Gly Gln Ile Phe Leu Leu Phe Asp Ser
        355                 360                 365
Glu Lys Arg Met Trp Thr Thr Val His Pro Gly Ala Arg Lys Met Lys
    370                 375                 380
Glu Lys Trp Glu Asn Asp Lys Val Val Ala Thr Lys Leu Tyr Leu Trp
385                 390                 395                 400
Ser Met Gly Asp Cys Ile Gly Trp Leu Glu Asp Phe Leu Met Gly Met
                405                 410                 415
Asp Ser Thr Leu Glu Pro Ser Leu Ile Ser Gly Arg
            420                 425

<210> SEQ ID NO 169
<211> LENGTH: 11
<212> TYPE: PRT
<213> ORGANISM: Artificial Sequence
<220> FEATURE:
<223> OTHER INFORMATION: Synthetic sequence, 3BNC60 and 3BNC117 binding
      epitope

<400> SEQUENCE: 169

Ser Ser Gly Gly Asp Pro Glu Ile Val Thr His
1               5                   10
```

<210> SEQ ID NO 170
<211> LENGTH: 36
<212> TYPE: PRT
<213> ORGANISM: Artificial Sequence
<220> FEATURE:
<223> OTHER INFORMATION: Synthetic sequence, PGF12 and 10-1074 binding
      epitope

<400> SEQUENCE: 170

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

<210> SEQ ID NO 171
<211> LENGTH: 171
<212> TYPE: PRT
<213> ORGANISM: Homo sapiens

<400> SEQUENCE: 171

His Ser Leu Arg Tyr Asn Leu Thr Val Leu Ser Gly Asp Gly Ser Val
1               5                   10                  15

Gln Ser Gly Phe Leu Ala Glu Val His Leu Asp Gly Gln Pro Phe Leu
            20                  25                  30

Arg Cys Asp Arg Gln Lys Cys Arg Ala Lys Pro Gln Gly Gln Trp Ala
        35                  40                  45

Glu Asp Val Leu Gly Asn Lys Thr Trp Asp Arg Glu Thr Arg Asp Leu
50                  55                  60

Thr Gly Asn Gly Lys Asp Leu Arg Met Thr Leu Ala His Ile Lys Asp
65                  70                  75                  80

Gln Lys Glu Gly Leu His Ser Leu Gln Glu Ile Arg Val Cys Glu Ile
                85                  90                  95

His Glu Asp Asn Ser Thr Arg Ser Ser Gln His Phe Tyr Tyr Asp Gly
            100                 105                 110

Glu Leu Phe Leu Ser Gln Asn Leu Glu Thr Glu Glu Trp Thr Met Pro
        115                 120                 125

Gln Ser Ser Arg Ala Gln Thr Leu Ala Met Asn Val Arg Asn Phe Leu
    130                 135                 140

Lys Glu Asp Ala Met Lys Thr Lys Thr His Tyr His Ala Met His Ala
145                 150                 155                 160

Asp Cys Leu Gln Glu Leu Arg Arg Tyr Leu Lys
                165                 170

<210> SEQ ID NO 172
<211> LENGTH: 169
<212> TYPE: PRT
<213> ORGANISM: Homo sapiens

<400> SEQUENCE: 172

His Cys Leu Cys Tyr Asp Phe Ile Ile Thr Pro Lys Ser Arg Pro Glu
1               5                   10                  15

Pro Gln Trp Cys Glu Val Gln Gly Leu Val Asp Glu Arg Pro Phe Leu
            20                  25                  30

His Tyr Asp Cys Val Asn His Lys Ala Lys Ala Phe Ala Ser Leu Gly
        35                  40                  45

```
Lys Lys Val Asn Val Thr Lys Thr Trp Glu Gln Thr Glu Thr Leu
    50              55                  60

Arg Asp Val Val Asp Phe Leu Lys Gly Gln Leu Leu Asp Ile Gln Val
65                  70                  75                  80

Glu Asn Leu Ile Pro Ile Glu Pro Leu Thr Leu Gln Ala Arg Met Ser
                85                  90                  95

Cys Glu His Glu Ala His Gly His Gly Arg Gly Ser Trp Gln Phe Leu
                100             105                 110

Phe Asn Gly Gln Lys Phe Leu Leu Phe Asp Ser Asn Arg Lys Trp
                115                 120                 125

Thr Ala Leu His Pro Gly Ala Lys Lys Met Thr Glu Lys Trp Glu Lys
130                 135                 140

Asn Arg Asp Val Thr Met Phe Phe Gln Lys Ile Ser Leu Gly Asp Cys
145                 150                 155                 160

Lys Met Trp Leu Glu Glu Phe Leu Met
                165
```

<210> SEQ ID NO 173
<211> LENGTH: 169
<212> TYPE: PRT
<213> ORGANISM: Homo sapiens

<400> SEQUENCE: 173

```
His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
                20                  25                  30

His Tyr Asp Cys Gly Asn Lys Thr Val Thr Pro Val Ser Pro Leu Gly
                35                  40                  45

Lys Lys Leu Asn Val Thr Thr Ala Trp Lys Ala Gln Asn Pro Val Leu
    50              55                  60

Arg Glu Val Val Asp Ile Leu Thr Glu Gln Leu Arg Asp Ile Gln Leu
65                  70                  75                  80

Glu Asn Tyr Thr Pro Lys Glu Pro Leu Thr Leu Gln Ala Arg Met Ser
                85                  90                  95

Cys Glu Gln Lys Ala Glu Gly His Ser Ser Gly Ser Trp Gln Phe Ser
                100                 105                 110

Phe Asp Gly Gln Ile Phe Leu Leu Phe Asp Ser Glu Lys Arg Met Trp
                115                 120                 125

Thr Thr Val His Pro Gly Ala Arg Lys Met Lys Glu Lys Trp Glu Asn
130                 135                 140

Asp Lys Val Val Ala Met Ser Phe His Tyr Phe Ser Met Gly Asp Cys
145                 150                 155                 160

Ile Gly Trp Leu Glu Asp Phe Leu Met
                165
```

<210> SEQ ID NO 174
<211> LENGTH: 169
<212> TYPE: PRT
<213> ORGANISM: Homo sapiens

<400> SEQUENCE: 174

```
His Ser Leu Trp Tyr Asn Phe Thr Ile Ile His Leu Pro Arg His Gly
1               5                   10                  15

Gln Gln Trp Cys Glu Val Gln Ser Gln Val Asp Gln Lys Asn Phe Leu
                20                  25                  30
```

Ser Tyr Asp Cys Gly Ser Asp Lys Val Leu Ser Met Gly His Leu Glu
        35                  40                  45

Glu Gln Leu Tyr Ala Thr Asp Ala Trp Gly Lys Gln Leu Glu Met Leu
 50                  55                  60

Arg Glu Val Gly Gln Arg Leu Arg Leu Glu Leu Ala Asp Thr Glu Leu
 65                  70                  75                  80

Glu Asp Phe Thr Pro Ser Gly Pro Leu Thr Leu Gln Val Arg Met Ser
                 85                  90                  95

Cys Glu Cys Glu Ala Asp Gly Tyr Ile Arg Gly Ser Trp Gln Phe Ser
                100                 105                 110

Phe Asp Gly Arg Lys Phe Leu Leu Phe Asp Ser Asn Asn Arg Lys Trp
                115                 120                 125

Thr Val Val His Ala Gly Ala Arg Arg Met Lys Glu Lys Trp Glu Lys
                130                 135                 140

Asp Ser Gly Leu Thr Thr Phe Phe Lys Met Val Ser Met Arg Asp Cys
145                 150                 155                 160

Lys Ser Trp Leu Arg Asp Phe Leu Met
                165

<210> SEQ ID NO 175
<211> LENGTH: 168
<212> TYPE: PRT
<213> ORGANISM: Homo sapiens

<400> SEQUENCE: 175

His Ser Leu Cys Phe Asn Phe Thr Ile Lys Ser Leu Ser Arg Pro Gly
 1               5                  10                  15

Gln Pro Trp Cys Glu Ala Gln Val Phe Leu Asn Lys Asn Leu Phe Leu
                20                  25                  30

Gln Tyr Asn Ser Asp Asn Asn Met Val Lys Pro Leu Gly Leu Leu Gly
                35                  40                  45

Lys Lys Val Tyr Ala Thr Ser Thr Trp Gly Glu Leu Thr Gln Thr Leu
 50                  55                  60

Gly Glu Val Gly Arg Asp Leu Arg Met Leu Leu Cys Asp Ile Lys Pro
 65                  70                  75                  80

Gln Ile Lys Thr Ser Asp Pro Ser Thr Leu Gln Val Glu Met Phe Cys
                 85                  90                  95

Gln Arg Glu Ala Glu Arg Cys Thr Gly Ala Ser Trp Gln Phe Ala Thr
                100                 105                 110

Asn Gly Glu Lys Ser Leu Leu Phe Asp Ala Met Asn Met Thr Trp Thr
                115                 120                 125

Val Ile Asn His Glu Ala Ser Lys Ile Lys Glu Thr Trp Lys Lys Asp
130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly
                165

<210> SEQ ID NO 176
<211> LENGTH: 169
<212> TYPE: PRT
<213> ORGANISM: Homo sapiens

<400> SEQUENCE: 176

His Ser Leu Cys Tyr Asp Ile Thr Val Ile Pro Lys Phe Arg Pro Gly
 1               5                  10                  15

```
Pro Arg Trp Cys Ala Val Gln Gly Gln Val Asp Glu Lys Thr Phe Leu
            20                  25                  30

His Tyr Asp Cys Gly Ser Lys Thr Val Thr Pro Val Ser Pro Leu Gly
            35                  40                  45

Lys Lys Leu Asn Val Thr Thr Ala Trp Lys Ala Gln Asn Pro Val Leu
        50                  55                  60

Arg Glu Val Val Asp Ile Leu Thr Glu Gln Leu Leu Asp Ile Gln Leu
65                      70                  75                  80

Glu Asn Tyr Ile Pro Lys Glu Pro Leu Thr Leu Gln Ala Arg Met Ser
                85                  90                  95

Cys Glu Gln Lys Ala Glu Gly His Gly Ser Gly Ser Trp Gln Leu Ser
            100                 105                 110

Phe Asp Gly Gln Ile Phe Leu Leu Phe Asp Ser Glu Asn Arg Met Trp
            115                 120                 125

Thr Thr Val His Pro Gly Ala Arg Lys Met Lys Glu Lys Trp Glu Asn
            130                 135                 140

Asp Lys Asp Met Thr Met Ser Phe His Tyr Ile Ser Met Gly Asp Cys
145                 150                 155                 160

Thr Gly Trp Leu Glu Asp Phe Leu Met
                165

<210> SEQ ID NO 177
<211> LENGTH: 169
<212> TYPE: PRT
<213> ORGANISM: Homo sapiens

<400> SEQUENCE: 177

His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
            20                  25                  30

His Tyr Asp Cys Gly Asn Lys Thr Val Thr Pro Val Ser Pro Leu Gly
            35                  40                  45

Lys Lys Leu Asn Val Thr Thr Ala Trp Lys Ala Gln Asn Pro Val Leu
        50                  55                  60

Arg Glu Val Val Asp Ile Leu Thr Glu Gln Leu Leu Asp Ile Gln Leu
65                      70                  75                  80

Glu Asn Tyr Thr Pro Lys Glu Pro Leu Thr Leu Gln Ala Arg Met Ser
                85                  90                  95

Cys Glu Gln Lys Ala Glu Gly His Ser Ser Gly Ser Trp Gln Phe Ser
            100                 105                 110

Ile Asp Gly Gln Thr Phe Leu Leu Phe Asp Ser Glu Lys Arg Met Trp
            115                 120                 125

Thr Thr Val His Pro Gly Ala Arg Lys Met Lys Glu Lys Trp Glu Asn
            130                 135                 140

Asp Lys Asp Val Ala Met Ser Phe His Tyr Ile Ser Met Gly Asp Cys
145                 150                 155                 160

Ile Gly Trp Leu Glu Asp Phe Leu Met
                165
```

MODIFIED NON-NATURAL NKG2D LIGANDS THAT SELECTIVELY DELIVER ATTACHED HETEROLOGOUS MOLECULES TO NON-NATURAL NKG2D RECEPTORS ON CAR-CELLS

BACKGROUND OF THE INVENTION

Field of the Invention

This application relates generally to modified, non-natural α1-α2 domains of NKG2D ligands with attached polypeptides having specific target-binding properties, for example, antibodies or fragments of antibodies, that are selectively delivered to Chimeric Antigen Receptors (CARs) comprised of modified, non-natural NKG2D receptors on engineered mammalian cells.

Background Information

An antibody (Ab), FIG. 1, also known as an immunoglobulin (Ig), in many mammals including humans is a large, Y-shape protein used by the immune system to identify and neutralize foreign objects such as bacteria and viruses (Charles Janeway (2001). *Immunobiology*. (5th ed.), Chapter 3. Garland Publishing. ISBN 0-8153-3642-X. (electronic full text via NCBI Bookshelf). The antibody recognizes a unique part of the foreign target, called an antigen. Each tip of the two arms of the "Y" of an antibody contains an antigen binding site, or a paratope, (a structure analogous to a lock) that is specific for one particular epitope (similarly analogous to a key) of an antigen, allowing these two structures to bind together with precision. Using this binding mechanism, an antibody can tag a microbe or an infected cell for attack by other parts of the immune system or can neutralize its target directly, for example, by blocking a part of a microbe that is essential for its invasion and survival. The production of antibodies is the main function of the humoral, or "adaptive", immune system. Antibodies are secreted by plasma cells. Antibodies in nature can occur in two physical forms, a soluble form that is secreted from the cell, and a membrane-bound form that is attached to the surface of a B cell via the "stem" of the Y.

Antibodies are glycoproteins belonging to the immunoglobulin superfamily and are typically made of basic structural units—each with two large heavy chains and two small light chains. There are several different types of antibody heavy chains, and several different kinds of antibodies, which are grouped into different isotypes based on which heavy chain they possess. Five different antibody isotypes are known in mammals (Market E, Papavasiliou F N (October 2003). "V(D)J recombination and the evolution of the adaptive immune system". *PLoS Biol.* 1 (1): E16. doi:10.1371/journal.pbio.0000016. PMC 212695. PMID 14551913). Although the general structure of all antibodies is very similar, a small region at the tip of each arm of the Y-shaped protein is extremely variable, allowing millions of antibodies with slightly different tip structures, or antigen-binding sites, to exist. This region is known as the hypervariable or variable region. Each of these natural variants can bind to a different antigen. This enormous diversity of antibodies allows the immune system to adapt and recognize an equally wide variety of antigens (Hozumi N, Tonegawa S (1976). "Evidence for somatic rearrangement of immunoglobulin genes coding for variable and constant regions". *Proc. Natl. Acad. Sci. U.S.A.* 73 (10): 3628-3632. doi:10.1073/pnas.73.10.3628. PMC 431171. PMID 824647.)

The natural "Y"-shaped Ig molecule consists of four polypeptide chains; two identical heavy chains and two identical light chains connected by disulfide bonds. Each heavy chain has two major regions, the constant region (CH) and the variable region (VH). The constant region is essentially identical in all antibodies of the same isotype, but differs in antibodies of different isotypes. A light chain also has two successive domains: a smaller constant region (CL) and the variable region (VL) (Woof J, Burton D (2004). "Human antibody-Fc receptor interactions illuminated by crystal structures." *Nat Rev Immunol* 4 (2): 89-99. doi: 10.1038/nri1266. PMID 15040582).

Some parts of an antibody have the same functions. Each of the two arms of the Y, for example, contains the sites that can bind to antigens and, therefore, recognize specific foreign objects. This region of the antibody is called the Fv (fragment, variable) region. It is composed of one variable domain from the heavy chain ($V_H$) and one variable region from the light chain ($V_L$) of the antibody (Hochman J, Inbar D, Givol D (1973). An active antibody fragment (Fv) composed of the variable portions of heavy and light chains. Biochemistry 12 (6): 1130-1135. doi:10.1021/bi00730a018. PMID 4569769). The paratope is shaped at one end of the Fv and is the region for binding to antigens. It is comprised of variable loops of β-strands, three each on the $V_L$ and on the $V_H$ and is responsible for binding to the antigen. These 6 loops are referred to as the complementarity determining regions (CDRs) (North B, Lehmann A, Dunbrack R L (2010). "A new clustering of antibody CDR loop conformations". *J Mol Biol* 406 (2): 228-256. doi:10.1016/j.jmb.2010.10.030. PMC 3065967. PMID 21035459).

Useful polypeptides that possess specific antigen binding function can be derived from the CDRs of the variable regions of antibodies. These two antibody variable domains, one of the light chain ($V_L$) and one from the heavy chain ($V_H$), each with 3 CDRs can be fused in tandem, in either order, using a single, short linker peptide of 10 to about 25 amino acids to create a linear single-chain variable fragment (scFv) polypeptide comprising one each of heavy and light chain variable domains (Bird, R. E., Hardman, K. D., Jacobson, J. W., Johnson, S., Kaufman, B. M., Lee, S. M., Lee, T., Pope, S. H., Riordan, G. S., and Whitlow, M. (1988) Single-chain antigen-binding proteins, Science 242, 423-426; Huston, J. S., Levinson, D, Mudgett-Hunter, M, Tai, M-S, Novotny, J, Margolies, M. N., Ridge, R., Bruccoleri, R E., Haber, E., Crea, R., and Opperman, H. (1988). Protein engineering of antibody binding sites: Recovery of specific activity in an anti-digoxin single-chain Fv analogue produced in *Escherichia coli*. PNAS 85: 5879-5883).

The linker is usually rich in glycine for flexibility, as well as serine, threonine, or charged amino acids for solubility, and can either connect the N-terminus of the $V_H$ with the C-terminus of the $V_L$, or vice versa. This protein retains the specificity of the original immunoglobulin, despite removal of the constant regions and the introduction of the single linker. This format enables one ordinarily skilled in the art of recombinant DNA technology to genetically fuse the linear scFv to the N- or C-terminus of a parent protein in order to impart to the parent protein the antigen binding properties of the scFv. There are numerous other proposed or created arrangements of polyvalent and tandem scFv regions, but importantly as described below, all have at least two spatially distant termini, (Le Gall, F.; Kipriyanov, S M; Moldenhauer, G; Little, M (1999). "Di-, tri- and tetrameric single chain Fv antibody fragments against human CD19:

SUMMARY OF THE INVENTION

The present disclosure relates to modified α1-α2 domains of NKG2D ligands attached to heterologous polypeptides, in some embodiments antibodies or fragments of antibodies. The modified ligands bind selectively to cognate non-natural NKG2D receptors which in-turn bind selectively to their cognate modified ligands. The non-natural NKG2D receptors can be expressed on the surfaces of cells of the immunity system and create a chimeric receptor on surface of that effector cell. The heterologous molecule attached to the ligand may also bind a specific molecule on the surface of a target cell, thereby delivering the immunity effector cell to a target cell. Such effector cells include lymphocytes, B-cells, plasma cells, monocytes, macrophages and dendritic cells.

In some embodiments, the present disclosure relates to a modified, non-natural ligand for a modified, non-natural NKG2D receptor wherein the ligand has an attached heterologous molecule that selectively binds an HIV protein present on the surface of a cell infected by HIV, wherein the modified ligand with its heterologous molecule can selectively bind to a modified, non-natural NKG2D receptor of a CAR-cell and cause the destruction of the HIV-infected cell.

In further embodiments, the HIV protein which the heterologous molecule selectively binds to is an HIV envelope protein.

In yet further embodiments, the epitope of the envelope protein to which the heterologous molecule selectively binds comprises SEQ ID NO: 169 or SEQ ID NO: 170.

In some embodiments of the present disclosure, the modified, non-natural ligand comprises SEQ ID NO: 68, 69, 70, 71, or 72.

In further embodiments, the modified, non-natural NKG2D receptor comprises SEQ ID NO: 54 or 154.

In some embodiments of the present disclosure, the HIV protein is expressed on an HIV infected cell that has been shocked or activated by a mechanism or agent, or a latency reactivating agent, known to provoke the expression of an HIV protein on a latent HIV-infected cell.

In some embodiments of the present disclosure, the CAR-cell has bound multiple modified, non-natural ligands with different, distinct heterologous molecules binding different epitopes, proteins or other molecules on the surface of an HIV-infected cell.

In some embodiments of the present disclosure, a modified, non-natural NKG2D receptor comprising SEQ ID NO: 54 or 154 is present on a CAR-cell, wherein the modified NKG2D receptor binds a modified, non-natural ligand comprised of SEQ ID NO: 68, 69, 70, 71, or 72, to which is attached a heterologous molecule or atom that does not bind an HIV protein.

In further embodiments, the heterologous molecule or atom modulates the function of the CAR-cell. In yet further embodiments, the cellular function includes proliferation, differentiation, ablation, imaging, antagonism of immunosuppression, homing, or cytolysis of a cell not infected by HIV.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5. Protein sequence alignment of α1-α2 domains from MICA and ULBP 1-6 (SEQ ID NOs: 171-177, respectively). Amino acids highlighted in grey were selected for NNK mutagenesis in ULBP2 (60 amino acids) and ULBP3 (36 amino acids). Residues highlighted in black were identified as key positions for selected and identified as mutations that modulate binding affinity to NKG2D (Tables 6 and 7).

FIG. 11. Non-natural α1-α2 domain variants selected for increased affinity to natural NKG2D receptor and the MICwed variant described previously (McFarland et al., 2003). The positions of the indicated amino acid changes referenced to the residue positions in SEQ ID NO.: 7 and the common names of the variants and their SEQ ID NOs are provided.

FIG. 12. Kinetic parameters of the wild type (wt or natural) and 8 variant α1-α2 domain α3-Fv fusion proteins binding to the natural NKG2D. MICwed-Fv was here studied in 2 separate Octet analyses, once comparing to the wt α1-α2 domain α3-Fv fusion and the other compared to 7 other non-natural α1-α2 domain α3-Fv fusions. The common names of each α1-α2 domain variants and the SEQ ID NO.s of their α3-Fv fusion proteins are provided along with their affinity (Kd) values in molar (M), on rates (kon) in inverse molar-seconds (1/Ms), and dissociation- or off-rates (kdis) in inverse seconds.

FIG. 13. Selected mutations within DSM25 that resulted in Y152A-specific phage clones.

FIG. 14. Selected mutations within ULBP2 R80W that resulted in Y152A-specific phage clones.

FIG. 15. Selected mutations within ULBP3 R162G that resulted in Y152A-specific phage clones.

FIG. 16. Specificity of NKG2D.AF-selected ULBP2 variants in rituximab-MicAbody format retained their binding to NKG2D.AF by quantitative ELISA. The specific amino acid modifications of each ULBP2 variant are shown as are the ratios of their binding to Fc-NKG2D.wt fusion versus Fc-NKG2D.AF fusion.

FIG. 17. Selected mutations at the indicated amino acid locations of ULBP2.R80W (SEQ ID NO: 132) that resulted in Y152A-specific phage clones.

DETAILED DESCRIPTION OF THE INVENTION

Natural killer (NK) cells, cells of the monocyte-macrophage lineage, and certain (CD8+ αβ and γδ) T-cells of the immunity system have important roles in humans and other mammals as first-line, innate defense against neoplastic and virus-infected cells (Cerwenka, A., and L. L. Lanier. 2001. NK cells, viruses and cancer. Nat. Rev. Immunol. 1:41-49). NK cells and certain T-cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. Science 285: 727-730). The human NKG2D molecule possesses a C-type lectin-like extracellular domain that binds to its cognate ligands, the 84% sequence identical or homologous, monomeric MICA and MICB, polymorphic analogs of the Major Histocompatibility Complex (MHC) Class I chain-related glycoproteins (MIC) (Weis et al. 1998. The C-type lectin superfamily of the immune system. Immunol. Rev. 163: 19-34; Bahram et al. 1994. A second lineage of mammalian MHC class I genes. PNAS 91:6259-6263; Bahram et al. 1996a. Nucleotide sequence of the human MHC class I MICA gene. Immunogenetics 44: 80-81; Bahram and Spies TA. 1996. Nucleotide sequence of human MHC class I MICB cDNA. Immunogenetics 43: 230-233). Non-pathologic expression of MIC proteins is generally restricted to intestinal epithelium, keratinocytes, endothelial cells and monocytes, but aberrant surface expression of these MIC proteins occurs in response to many types of cellular stress such as proliferation, oxidation, viral infection, and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδT cells. Science 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, J V and Lanier L L. 2000. Immune Inhibitory Receptors. Science 290: 84-89; Burgess, S J. 2008. Immunol. Res. 40: 18-34). The differential regulation of NKG2D ligands, such as the polymorphic MICA and MICB, is important to provide the immunity system with a means to identify and respond to a broad range of emergency cues while still protecting healthy cells from unwanted attack (Stephens H A, (2001) MICA and MICB genes: can the enigma of their polymorphism be resolved? Trends Immunol. 22: 378-85; Spies, T. 2008. Regulation of NKG2D ligands: a purposeful but delicate affair. Nature Immunol. 9: 1013-1015).

Viral infection is a common inducer of MIC protein expression and identifies the viral-infected cell for NK or T-cell attack (Groh et al. 1998; Groh et al. 2001. Co-stimulation of CD8+ααβT-cells by NKG2D via engagement by MIC induced on virus-infected cells. Nat. Immunol. 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape the wrath of the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. J. Exp. Med. 197:1245-1253; Stern-Ginossar et al., (2007) Host immune system gene targeting by viral miRNA. Science 317: 376-381; Stern-Ginossar et al., (2008) Human microRNAs regulate stress-induced immune responses mediated by the receptor NKG2D. Nature Immunology 9: 1065-73; Slavuljica, I A Busche, M Babic, M Mitrovic, I Gašparovic, Đ Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. J. Clin. Invest. 120: 4532-4545).

In spite of their stress, many malignant cells, such as those of lung cancer and glioblastoma brain cancer, also avoid the expression of MIC proteins and as a result may be particularly aggressive as they too escape the innate immunity system (Busche, A et al. 2006, NK cell mediated rejection of experimental human lung cancer by genetic over expression of MHC class I chain-related gene A. Human Gene Therapy 17: 135-146; Doubrovina, E S, M M Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. J. Immunology, 180: 4606-4614).

Figure 1:
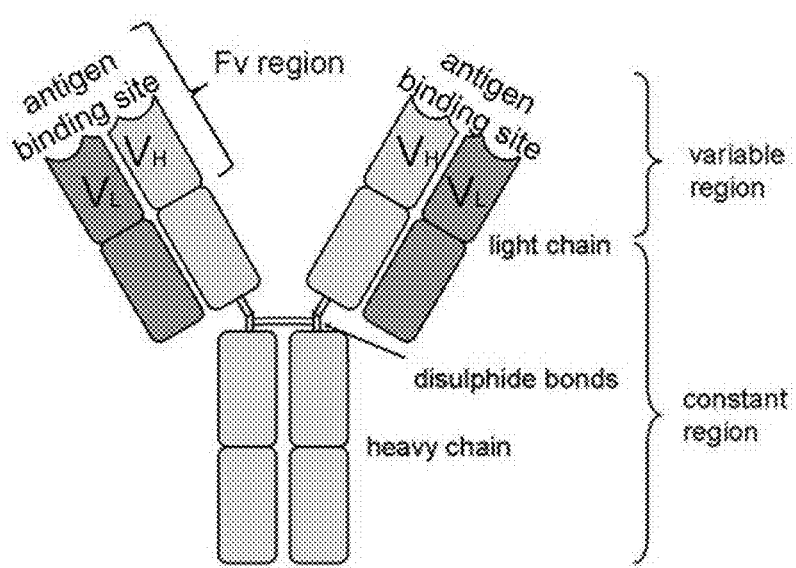
FIG. 1. A cartoon of a typical mammalian antibody showing its Y-shaped structure and structural components.

The high resolution structure of human MICA bound to NKG2D has been solved and demonstrates that the α3 domain of MICA has no direct interaction with the NKG2D (Li et al. 2001. Complex structure of the activating immunoreceptor NKG2D and its MHC class I-like ligand MICA. Nature Immunol. 2: 443-451; Protein Data Bank accession code 1HYR). The α3 domain of MICA, like that of MICB, is connected to the α1-α2 platform domain by a short, flexible linker peptide, and itself is positioned naturally as "spacer" between the platform and the surface of the MIC expressing cell. The 3-dimensional structures of the human MICA and MICB α3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. J Immunol. 169: 1395-1400).

Certain non-natural α1-α2 domains of NKG2D ligands modified to bind natural human NKG2D receptors with higher affinities than do natural α1-α2 domains have been described (Candice S. E. Lengyel, Lindsey J. Willis, Patrick Mann, David Baker, Tanja Kortemme, Roland K. Strong and Benjamin J. McFarland. Mutations Designed to Destabilize the Receptor-Bound Conformation Increase MICA-NKG2D Association Rate and Affinity. Journal of Biological Chemistry Vol. 282, no. 42, pp. 30658-30666, 2007; Samuel H. Henager, Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland. Combining different design strategies for rational affinity maturation of the MICA-NKG2D interface. Protein Science 2012 VOL 21:1396-1402. Herein we describe non-natural α1-α2 domains of NKG2D ligands that have been modified to bind non-natural NKG2D receptors, themselves mutated at sites which consequentially result in compromised or loss of binding to natural α1-α2 domains of NKG2D ligands (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523; U.S. patent application Ser. No. 14/562,534; U.S. PTO provisional application 62/088,456)). This invention creates bispecific molecules comprised of the specifically modified non-natural α1-α2 domains and specific targeting heterologous molecules, including but not limited to heterologous peptides or polypeptides, that bind Chimeric Antigen Receptors (CARs) wherein the receptor of the CAR is comprised of a non-natural NKG2D receptor ectodomain that binds the modified α1-α2 domains with greater affinity than it does natural α1-α2 domains. Genetically engineered cells of the immunity system, e.g. B-cells, T-cells, NK-cells, and macrophages, comprised of such CARs can then overcome many of the disadvantages, including known severe systemic toxicities and antigen escape, of current CAR-T and CAR-NK cell therapeutics as described below (Kalos M, Levine, B L, Porter, D L, Katz, S, Grupp, S A, Bagg, A and June, C. T Cells with chimeric antigen receptors have potent antitumor effects and can establish memory in patients with advanced leukemia. Sci Transl Med 2011; 3:95ra73; Morgan R A, Yang J C, Kitano M, Dudley M E, Laurencot C M, Rosenberg S A. Case report of a serious adverse event following the administration of T cells transduced with a chimeric antigen receptor recognizing ERBB2. Mol Ther 2010, 18:843-851; Gill and June 2015).

T-cells, NK-cells, and macrophages can be modified using gene transfer technologies to directly and stably express on their surface binding domains of an antibody that confer novel antigen specificities (Saar Gill & Carl H. June. Going viral: chimeric antigen receptor T-cell therapy for hematological malignancies. Immunological Reviews 2015. Vol. 263: 68-89; Wolfgang Glienke, Ruth Esser, Christoph Priesner, Julia D. Suerth, Axel Schambach, Winfried S. Wels, Manuel Grez, Stephan Kloess, Lubomir Arseniev and Ulrike Koehl. 2015. Advantages and applications of CAR-expressing natural killer cells. Front. Pharmacol. doi: 10.3389/fphar.2015.00021). CAR-T cells are applications of this approach that combines an antigen recognition domain of a specific antibody with an intracellular domain of the CD3-ζ chain, which is the primary transmitter of signals from endogenous T-Cell Receptors (TCRs), into a single chimeric protein along with a co-stimulatory molecule such as CD27, CD28, ICOS, 4-1BB, or OX40, FIG. 2. CARs so constructed can trigger T cell activation upon binding the targeted antigen in a manner similar to an endogenous T cell receptor but independent of the major histocompatibility complex (MHC).

As used herein, a "soluble MIC protein", "soluble MICA" and "soluble MICB" refer to a MIC protein containing the α1-α2 domain with or without an α3 domains of the MIC protein but without a membrane attachment motif, a transmembrane or an intracellular domains. The NKG2D ligands, ULBP1-6, do not naturally possess an α3 domain (Cerwenka A, Lanier L L. 2004. NKG2D ligands: unconventional MHC class I-like molecules exploited by viruses and cancer. *Tissue Antigens* 61 (5): 335-43. doi:10.1034/j.1399-0039.2003.00070.x. PMID 12753652). An "α1-α2 domain" of an NKG2D ligand refers to the protein domain of the ligand that binds an NKG2D receptor.

In some embodiments, the α1-α2 domains of the non-natural NKG2D ligand proteins of the invention are at least 80% identical or homologous to the native or natural α1-α2 domain of an NKG2D ligand, SEQ ID NOs: 1-19. In other embodiments, the modified α1-α2 domain is 85% identical to a native or natural α1-α2 domain of an NKG2D ligand. In yet other embodiments, the modified α1-α2 domain is 90% identical to a native or natural α1-α2 domain of a natural NKG2D ligand protein and binds non-natural NKG2D.

The α1-α2 platform domain of a soluble MIC protein is diffusible in the intercellular or intravascular space of the mammal. Preferably the α1-α2 platform domains of the non-natural MIC proteins of the invention are at least 80% identical or homologous to a native or natural α1-α2 domain of a human MICA or MICB protein and bind the natural NKG2D or in certain examples, bind to modified, non-natural NKG2D receptors. In some embodiments, the α1-α2 platform domain is 85% identical to a native or natural α1-α2 platform domain of a human MICA, human MICB, or a human ULBP1-6 protein and binds the natural NKG2D or a modified, non-natural NKG2D. In other embodiments, the α 1-α2 platform domain is 90%, 95%, 96%, 97%, 98%, or 99% identical to a native or natural α1-α2 platform domain of a human MICA, human MICB, or a human ULBP1-6 protein and binds the natural NKG2D receptor or a modified, non-natural NKG2D receptor.

In some embodiments, a heterologous peptide tag may be fused to the N-terminus or C-terminus of an α1-α2 domain or another soluble MIC protein to aid in the purification of the soluble MIC protein. Tag sequences include peptides such as a poly-histidine, myc-peptide or a FLAG tag. Such tags may be removed after isolation of the MIC molecule by methods known to one skilled in the art.

In other embodiments of the invention, specific mutations in α1-α2 domains of NKG2D ligands can be made to create non-natural α1-α2 domains that bind non-natural NKG2D receptors, themselves engineered so as to have reduced affinity for natural NKG2D ligands. This can be done, for example, through genetic engineering. A non-natural NKG2D receptor so modified can be used to create on the surface of NK-cells, T-cells, macrophages, or stem cells of the immunity system a non-natural NKG2D-based Chimeric Antigen Receptor (CAR) that can preferentially bind to and be activated by molecules comprised of the invented non-natural α1-α2 domains. These pairs of non-natural NKG2D receptors and their invented cognate non-natural NKG2D ligands will provide important safety, efficacy, and manufacturing advantages for treating cancer and viral infections as compared to the current CAR-T cells and CAR-NK cells, as described below.

Engineering T cells with CARs has emerged as a promising approach to adoptive T cell therapy for cancer, and CARs targeting many different molecules have been tested in CAR-T cells as therapeutics for malignancies (Porter D L, Levine B L, Kalos M, Bagg A, June C H. Chimeric antigen receptor-modified T cells in chronic lymphoid leukemia. N Engl J Med. 365:725-733.). While remarkable clinical efficacy has been observed in hundreds of patients receiving adoptive transfer of T cells expressing CD19-specific chimeric antigen receptors, the processes of custom engineering a CAR to target a specific antigen, isolating autologous T-cells from the patient, genetically engineering the autologous T-cells to express the personalized CAR, expanding the modified cells in vitro, and controlling the quality their production have all been onerous and expensive. Currently this is feasible only in the context of large academic centers with extensive expertise and resources (Gill & June, 2015).

Once the autologous CAR-T cells are infused back into the donor patient, their expansion in vivo cannot be controlled—"living therapy", and there is not a dose-response relationship with efficacy (Gill & June, 2015). Furthermore, tumor escape from the CAR T-cell can occur through antigen loss escape (Stephan A. Grupp, M.D., Ph.D., Michael Kalos, Ph.D., David Barrett, M.D., Ph.D., Richard Aplenc, M.D., Ph.D., David L. Porter, M.D., Susan R. Rheingold, M.D., David T. Teachey, M.D., Anne Chew, Ph.D., Bernd Hauck, Ph.D., J. Fraser Wright, Ph.D., Michael C. Milone, M.D., Ph.D., Bruce L. Levine, Ph.D., and Carl H. June, M.D. Chimeric Antigen Receptor-Modified T Cells for Acute Lymphoid Leukemia. N Engl J Med 2013; 368:1509-1518), and this escape pathway can most readily be addressed by sequential therapy with a differently targeted CAR-T cell or by an initial infusion of a T-cell product that contains CARs of two or more specificities, further complicating the manufacturing processes and quality control.

In addition to CAR-T cells targeting tumors with single chain antibody binding domains (scFv), CAR-T cells that employ the ligand-binding domain of the NKG2D receptor have been studied in animals and recently in humans (Sentman C L, Meehan K R. NKG2D CARs as cell therapy for cancer. Cancer J. 2014 March-April; 20(2):156-9. doi: 10.1097/PPO.0000000000000029; Manfred Lehner, Gabriel Götz, Julia Proff, Niels Schaft, Jan Dörrie, Florian Full, Armin Ensser, Yves A. Muller, Adelheid Cerwenka, Hinrich Abken, Ornella Parolini, Peter F. Ambros, Heinrich Kovar, Wolfgang Holter. Redirecting T Cells to Ewing's Sarcoma Family of Tumors by a Chimeric NKG2D Receptor Expressed by Lentiviral Transduction or mRNA Transfection Research Article I published 15 Feb. 2012 I PLOS ONE 10.1371/journal.pone.0031210; www.clinicaltrials.gov NCT02203825). Since NKG2D ligand expression is increased on the surface of stressed cells, such as tumor cells and virus-infected cells, this family of natural NKG2D ligands is of significant interest as targets for viral infections and cancer immunotherapies (Spear P, Wu M R, Sentman M L, Sentman C L. NKG2D ligands as therapeutic targets. Cancer Immun. 2013 May 1; 13:8.; Song D G, Ye Q, Santoro S, Fang C, Best A, Powell D J Jr., Chimeric NKG2D CAR-expressing T cell-mediated attack of human ovarian cancer is enhanced by histone deacetylase inhibition. Hum Gene Ther. 2013 March; 24(3):295-305). One NKG2D CAR was a fusion of the full-length NKG2D receptor and CD3ζ (NKG2Dζ); another was with only the ectodomain of NKG2D fused in opposite orientation to a second-generation CAR scaffold composed of transmembrane and intracellular domains from CD28 and the signaling domain of CD3ζ (NKG2D28ζ). Since activation of NKG2D is dependent upon the presence of DAP10, a CAR-T cell was also constructed wherein DAP10 was co-expressed with NKG2Dζ (NKG2Dζ10). T cells expressing any of the above NKG2D CARs produced IFNγ and TNFα in response to NKG2D ligand stimulation and in vitro efficiently killed tumor targets expressing NKG2D ligands (Heather VanSeggelen, Joanne A. Hammill, Anna Dvorkin-Gheva, Daniela G.M. Tantalo, Jacek M. Kwiecien, Galina F. Denisova, Brian Rabinovich, Yonghong Wan, Jonathan L. Bramson, T cells engineered with chimeric antigen receptors targeting NKG2D ligands display lethal toxicity in mice, *Molecular Therapy* accepted article preview online 30 Jun. 2015; doi:10.1038/mt.2015.119). The cytotoxic potential of NK cells against a wide spectrum of tumor subtypes could also be markedly enhanced by expression of a CAR based on NKG2D-DAP10-CD3ζ (Yu-Hsiang Chang, John Connolly, Noriko Shimasaki, Kousaku Mimura, Koji Kono, and Dario Campana. Chimeric Receptor with NKG2D Specificity Enhances Natural Killer Cell Activation and Killing of Tumor Cells. Cancer Res; 73(6) Mar. 15, 2013).

However, following infusion into syngeneic murine hosts, significant toxicity occurred with these CAR-T constructs that bind and are activated by natural ligands of the natural NKG2D receptor. Signs of toxicity, including poor body condition, hunched posture, labored breathing, and decreased core body temperature were observed in tumor-bearing and tumor-free mice treated with NKG2D-based CAR-T cells as compared to untreated control mice. The severity of NKG2D CAR-T cell toxicity varied, with NKG2Dζ10 being severely toxic, NKG2D28ζ showing intermediate toxicity, and NKG2Dζ being tolerable. Clinical symptoms of toxicity and mortality rates were exacerbated when mice received chemotherapy prior to adoptive transfer of T cells expressing any of the NKG2D CARs (VanSeggelen et al. 2015). Chemotherapy and radiation are known to induce NKG2D ligands on otherwise healthy tissues (Xiulong Xu, Geetha S Rao, Veronika Groh, Thomas Spies, Paolo Gattuso, Howard L Kaufman, Janet Plate and Richard A Prinz. Major histocompatibility complex class I-related chain A/B (MICA/B) expression in tumor tissue and serum of pancreatic cancer: Role of uric acid accumulation in gemcitabine-induced MICA/B expression. BMC Cancer 2011, 11:194 doi:10.1186/1471-2407-11-194; Gannagé M, Buzyn A, Bogiatzi S I, Lambert M, Soumelis V, Dal Cortivo L, Cavazzana-Calvo M, Brousse N, Caillat-Zucman Induction of NKG2D ligands by gamma radiation and tumor necrosis factor-alpha may participate in the tissue damage during acute graft-versus-host disease. Transplantation. 2008 Mar. 27; 85(6):911-5. doi: 10.1097/TP.0b013e31816691ef.). Further characterization revealed that the toxicity coincided with a systemic cytokine storm and lethal levels of inflammation within the lungs. These data warn that extreme caution must be taken when using natural NKG2D ligands for targeted immunotherapy and demonstrate that enhancing T cell expression of strongly activating CARs can be detrimental in vivo (VanSeggelen et al. 2015).

CAR-T cells, CAR-NK cells and macrophages comprised of ectodomains of non-natural NKG2D receptors that do not or only poorly bind natural NKG2D ligands will not be subject to the above form of activation and thus will not be so toxigenic as a cell expressing CAR based on a natural NKG2D receptor. Furthermore, ectodomains of non-natural NKG2D receptors on cells will not be subject to downregulation by natural NKG2D ligands in a soluble format or on Myeloid Derived Suppressor Cells (MDSC) (Deng W, Gowen B G, Zhang L, Wang L, Lau S, Iannello A, Xu J, Rovis T L, Xiong N, Raulet D H, 2015. Antitumor immunity. A shed NKG2D ligand that promotes natural killer cell activation and tumor rejection. Science. 2015 Apr. 3; 348 (6230):136-9. doi: 10.1126/science.1258867. Epub 2015 Mar. 5). However, when such CAR cells bearing ectodomains of non-natural NKG2D receptors are engaged by bispecific molecules with the cognate non-natural α1-α2 domains of the instant invention and its heterologous targeting motif which has found and bound its intended target, the CAR will be activated and the CAR-cell's effector functions expressed. The effector functions of a CAR-T cell, a CAR-NK cell and a CAR-macrophage cell can ablate or compromise the viability or function of the targeted cell. A targeted cell may include a malignant cell, an immunosuppressive cell of a tumor, a cell contributing to an autoimmune disease, a cell infected by a virus, for example but not limited to HIV, a hepatitis virus, HTLV-1, CMV, EBV and other herpes viruses.

Because the CAR-T or CAR-NK cells comprised of non-natural NKG2D receptor ectodomains are not activated except in the presence of an engaged bispecific molecule comprised of a cognate non-natural α1-α2 domains, their activation can be controlled by the administered bispecific molecules, which as biopharmaceuticals will exhibit pharmacokinetics and pharmacodynamics well known in the field. In the event that an adverse event develops, the physician can simply modify the dosing regimen of the administered bispecific molecule rather than having to deploy an induced suicide mechanism to destroy the infused CAR cells as currently done (Monica Casucci and Attilio Bondanza. Suicide Gene Therapy to Increase the Safety of Chimeric Antigen Receptor-Redirected T Lymphocytes. J Cancer. 2011; 2: 378-382). Furthermore, such bispecific molecules with different specific targeting motifs can be administered simultaneously or sequentially to help address the emergence of tumor cell or virus-infected cell resistance and escape as a results of target antigen loss without having to create, expand and infuse multiple different autologous CAR cells (Gill & June, 2015). Since all CAR constructions can be identical for all CAR cells and the targeting specificity determined simply by the targeting motif of the produced bispecific molecule of the instant invention, manufacturing processes will be simplified and less expensive.

Many viruses have evolved with mechanisms to avoid the killing of their host cell by the natural immunity surveillance system, especially NKG2D-dependent components. For examples Adenovirus, Cytomegalic Inclusion Virus (CMV), Herpes viruses, HIV, Human T-cell Lymphoma Virus-1 (HTLV-1), and Papilloma Viruses all possess one or more mechanisms. Such viruses may express on the surface of their infected host cells viral antigens, epitopes of which can serve as virus-specific molecular targets for binding by antibodies, fragments of antibodies or other molecular targeting motifs. These cell surface-exposed molecular targets are attractive as targets for antibodies or adoptive cell therapies (ACT) to prevent the spread of viral infection or treat virus infection by eliminating virus-infected cells.

HIV-1 latency is established early during acute infection and is primarily found within memory CD4+ T cells. This reservoir, although almost transcriptionally silent, is fully capable of generating infectious virus when the host cell is reactivated by antigen or cytokine stimulation or when antiretroviral therapy (ART) is interrupted. The latent HIV reservoir is principally found in lymphoid tissues where >98% of the CD4+ T cells reside. Although ART is capable of suppressing viral replication, it fails to eradicate latent reservoirs (Ruelas, D. S. and W. C. Greene, *An integrated overview of HIV-1 latency*. Cell, 2013. 155(3): p. 519-29.). Efforts to purge latent HIV-1 have initially focused on reactivating latent proviruses with cytokines or T cell receptor activating agents. However, these strategies resulted in severe side effects and had low efficacy. The so-called "Shock and Kill" strategy, instead, involves reactivation of transcriptionally silent proviruses through administration of latency reversal agents (LRAs), which are chemical compounds able to induce HIV-1 transcription (Cary, D. C., K. Fujinaga, and B. M. Peterlin, *Molecular mechanisms of HIV latency*. J Clin Invest, 2016. 126(2): p. 448-54.). Upon reactivating latent viruses, the HIV envelope glycoprotein, gp160 is expressed on the surface of the activated cell, processed to gp120 and gp41. The domains V1, V2, V3, C1, C2 and the N-segment of gp120 provide attractive targets for attacking HIV infected cells with neutralizing antibodies and, as described in the instant invention, CAR-T cells.

Following reactivation of latently infected cells, the prediction was that these cells would produce viruses (that would be stopped by the administration of ART) and that these cells would die by apoptosis due to viral cytopathic effects thereby reducing the latent reservoir size. Testing this hypothesis showed that the reactivated cells do not die and the latent reservoir size does not shrink (Shan L, Deng K, Shroff N S, Durand C M, Rabi S A, Yang H C, Zhang H, Margolick J B, Blankson J N, Siliciano R F, *Stimulation of HIV-1-specific cytolytic T lymphocytes facilitates elimination of latent viral reservoir after virus reactivation*. Immunity. 2012; 36(3) p. 491-501.).Two major problems are still present after reactivation of the reservoir. The first relates to the emergence of viruses that are resistant to CTL killing (Deng K, Pertea M, Rongvaux A, Wang L, Durand C M, Ghiaur G, Lai J, McHugh H L, Hao H, Zhang H, J B, Gurer C, Murphy A J, Valenzuela D M, Yancopoulos G D, Deeks S G, Strowig T, Kumar P, Siliciano J D, Salzberg S L, Flavell R A, Shan L, *Siliciano RF Broad CTL response is required to clear latent HIV-1 due to dominance of escape mutations*. Nature. 2015 Jan. 15; 517(7534) p. 381-5.). This is a common problem in chronically infected individuals who were not treated with ART during the first 6 months of infection (the majority of chronically infected individuals). The second problem stems from exposure of CTLs to HIV-related chronic inflammation, leading to CTL exhaustion (Cella M, Presti R, Vermi W, Lavender K, Turnbull E, Ochsenbauer-Jambor C, Kappes J C, Ferrari G, Kessels L, Williams I; CHAVI Clinical Core B, McMichael A J, Haynes B F, Borrow P, Colonna M; NIAID Center for HIV/AIDS Vaccine Immunology. *Loss of DNA M-1 contributes to CD8+ T-cell exhaustion in chronic HIV-1 infection*. Eur J Immunol. 2010 April; 40(4):p. 949-54.). It seems likely that new approaches for killing reactivated reservoir cells are needed that avoid the problems of viral resistance and cellular exhaustion. We propose the construction of convertible CAR-T cells that take advantage of broadly neutralizing HIV antibodies to target CTLs for killing of a reactivated reservoir cell.

Thus, the instant invention expands the diversity and practicality of this remarkable, very promising immunologic approach to managing cancer or virus infections with CAR-T cells, CAR-NK cells, and/or macrophages while overcoming many of these current, recognized difficulties of ACT.

As used herein "peptide", "polypeptide", and "protein" are used interchangeably; and a "heterologous molecule", "heterologous peptide", "heterologous sequence" or "heterologous atom" is a molecule, peptide, nucleic acid or amino acid sequence, or atom, respectively, that is not naturally or normally found in physical conjunction with the subject molecule. As used herein, "non-natural" and "modified" are used interchangeably. As used herein, "natural" and "native" are used interchangeably and "NKG2D" and "NKG2D receptor" are used interchangeably. The term "antibody" herein is used in the broadest sense and specifically covers monoclonal antibodies, multispecific antibodies (e.g. bispecific antibodies), and antibody fragments, so long as they exhibit the desired biological activity. "Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multi-specific antibodies formed from antibody fragment(s).

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

Example 1 (Modified α1-α2 Domains of NKG2D Ligands.)

These are examples of attaching polypeptides to NKG2DLs which were modified to significantly enhance their binding affinity to the human NKG2D receptor. The α1-α2 domain of MIC proteins is an NKG2DL for the NKG2D receptor. This affinity is sufficient for physiologic activation of NK cells and stimulating lysis of cells expressing native full-length MIC proteins irreversibly tethered to the two-dimensional plasma membrane surface of a "target cell" (Bauer S, Groh V, Wu J, Steinle A, Phillips J H, Lanier L L, Spies T., Science. 1999 Jul. 30; 285(5428):727-9.). However, because engineered soluble MIC proteins of the instant invention reversibly bind specific target antigens on the surface of a target cell, the binding affinity of the engineered soluble MIC protein to NKG2D will directly affect the stability of the soluble MIC-dependent complex formed between NK cells and cells expressing target antigens. Especially if the affinity between sMICA and NKG2D is increased by a substantially slower dissociation rate or off-rate of the modified sMICA from NKG2D, the NK cell-based killing would be expected to be greater at lower densities of soluble MIC molecules bound to a target cell. Prior to the instant invention there had not been identified any α1-α2 mutations that alter the killing activity of soluble MIC proteins or significantly reduce the binding off-rate to enhance affinity of MIC proteins to NKG2D. A computational design effort showed that three mutations in the α1-α2 domain of wild-type MICA: N69W, K152E, and K154D (WED-MICA) in combination can moderately affect NKG2D binding affinity by affecting the stability of unbound MICA and thereby its association rate or on-rate of binding to NKG2D (Lengyel C S, Willis L J, Mann P, Baker D, Kortemme T, Strong R K, McFarland B J. J Biol Chem. 2007 Oct. 19; 282(42):30658-66. Epub 2007 Aug. 8); Subsequent extensive computational design work by the same group scanning by iterative calculations 22 amino acid positions of MICA theoretically in contact with NKG2D, according to the published structural descriptions (Li P, Morris D L, Willcox B E, Steinle A, Spies T, Strong R K., Nat Immunol. 2001 May; 2(5):443-451), showed experimentally that when combined with the earlier designed 3 changes, further rational, iterative computational design of MICA qualitatively changed its affinity for NKG2D from weak (Kd ~2.5 μM) to moderately tight (Kd=51 nM) with a total of seven combined mutations (Henager, Samuel H., Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland, 2102, Combining different design strategies for rational affinity maturation of the MICA-NKG2D interface. Protein Science 21:1396-1402). In contrast, the experimental approach described in the instant invention experimentally selected amino acid modifications of MICA that slowed the off-rate between the α1-α2 domain of MICA and NKG2D, commencing with a MICA stabilized by the 3 WED changes of Lengyel et al (Lengyel C S, Willis L J, Mann P, Baker D, Kortemme T, Strong R K, McFarland B J., J Biol Chem. 2007 Oct. 19; 282(42):30658-66. Epub 2007 Aug. 8).

This example relates to modifying the NKG2D binding affinity of soluble MIC proteins through engineering specific mutations at selected amino acid positions within the α1-α2 domain that influence the off-rate binding kinetics and thereby alter the NK cell-mediated killing activity of the invented non-natural, targeted MIC molecules.

Figure 3:
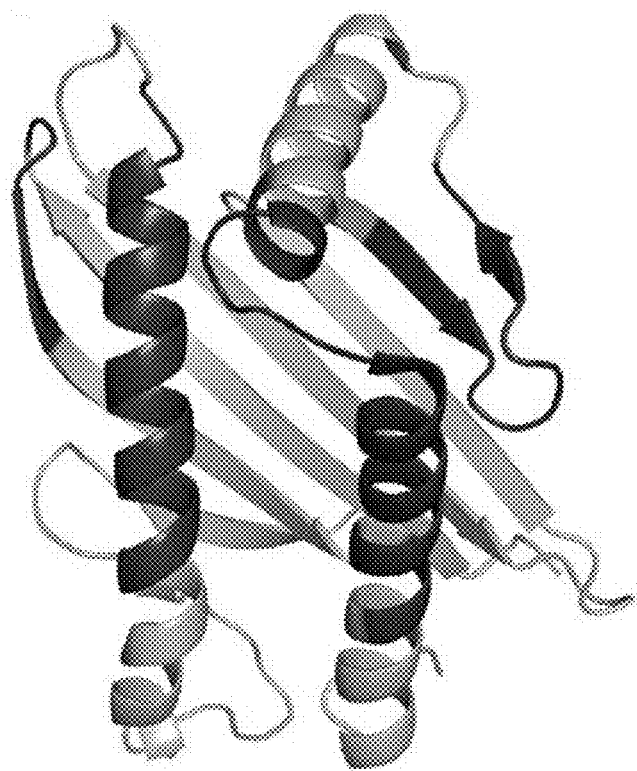
FIG. 3. Structure-directed mutagenesis of the α1-α2 domain of MICA for enhanced affinity to NKG2D. Structure of the α1-α2 domain of MICA (PDB 1HYR) with its NKG2D-binding surface colored dark grey where 57 specific amino acid sites were extensively mutagenized.

To engineer soluble non-natural α1-α2 domains with altered affinity to NKG2D 57 residues in the α1-α2 domain were chosen for extensive mutagenesis (FIG. 12). Synthetic DNA libraries coding for the α1-α2 domain and containing NNK mutagenic codons at each of the 57 amino acid positions were synthesized, individually cloned as fusions to the pIII minor coat protein of M13 phage, and phage particles displaying the mutagenized α1-α2 variants were produced in SS320 *E. coli* cells according to standard methodologies (Andris-Widhopf, J., Steinberger, P., Fuller, R., Rader, C., and Barbas, C. F., 3rd. (2011) Generation of human Fab antibody libraries: PCR amplification and assembly of light- and heavy-chain coding sequences, Cold Spring Harbor protocols 2011). The α1-α2 phage libraries were sorted for increased binding affinity using recombinant biotinylated NKG2D as the target antigen and cycled through iterative rounds of intentionally prolonged binding, prolonged washing, and eluting of the phage clones in order to select high affinity variants enriched for slow dissociation- or off-rates. A set of specific amino acid mutations occurred at high frequencies at 6 positions in α1-α2 and were selected as preferred amino acid substitutions with enhanced NKG2D binding affinity (FIG. 3, Table 1).

TABLE 1

Selected affinity mutations at the indicated 6 amino acid positions of the α1-α2 domain of MIC. The amino acids of SEQ ID NOs.: 20 at each of the 6 positions are shown in bold in the first row of the table. The identified affinity mutations are listed in decreasing frequency from top to bottom. All amino acids are represented by the single letter IUPAC abbreviations.

| S20 | G68 | K125 | E152 | H161 | O186 |
|-----|-----|------|------|------|------|
| P | L | L | T | R | F |
| T | F | R | V | S | S |
| D | S | F | G | A | H |
| A | A | T | F | K | Y |
| L | Y | A | Y | G | W |
| N | I | N | A | L | V |
|   | E | V | Q | F | L |
|   | T | Y | D | Y | M |
|   | W | I | I |   |   |
|   |   | S | N |   |   |
|   |   |   | S |   |   |
|   |   |   | H |   |   |
|   |   |   | M |   |   |
|   |   |   | P |   |   |

We synthesized DNA polynucleotides (SEQ ID NOs. 21-24) encoding the α1-α2 domains of 4 representative variants 15, 16, 17, 18 that contained different combinations of specific discovered mutations (Table 2).

TABLE 2

Sequences of specific α1-α2 domain variants. The specific amino acid substitutions for variants 15, 16, 17, and 18 (SEQ ID NOS.: 25-28, respectively) are listed relative to the amino acids of SEQ ID NO.: 20 in bold. All amino acids are represented by the single letter IUPAC abbreviations.

| Variant | SEQ ID NO.: | S20 | G68 | K125 | H161 |
|---------|-------------|-----|-----|------|------|
| 15 | 31 | S | G | N | R |
| 16 | 32 | S | G | L | R |
| 17 | 33 | S | L | L | R |
| 18 | 34 | P | L | L | R |

To the NKG2DLs in the above example, we directly attached heterologous molecules such as a polypeptide to each of these 4 modified α1-α2 NKG2DLs using a linker peptide. Four His-tagged proteins (SEQ ID NOs.: 25-28) consisting of modified NKG2DLs with attached heterologous molecules were expressed in insect cells and purified to characterize their NKG2D binding affinities and kinetic binding parameters. Using a competitive binding ELISA, we determined the relative NKG2D binding affinities of the 4 modified α1-α2 variants. A soluble wild type (WT) NKG2DL, sMICA protein, was coated in all wells of a maxisorp ELISA plate to provide a binding partner for the human NKG2D-Fc reagent. Solutions of the four α1-α2 variants as well as WT and WED-α1-α2 domains (SEQ ID NO.: 20) were titrated in the ELISA wells and allowed to competitively inhibit 2 nM human NKG2D-Fc binding to the WT sMICA coated on the plate. The level of human NKG2D-Fc that bound to the WT NKG2DL on the plate was detected using an anti-Fc-HRP antibody. FIG. 13, Panel A, shows variants 16, 17, and 18 exhibited $IC_{50}$ values of 0.7, 0.6, 0.5 nM while variant 15 exhibited an $IC_{50}$ value of 1.7 nM, all possessing significantly better binding to NKG2D, 27, 32-, 38- and 11-fold better, than WT NKG2DL, respectively, as well as substantially better than WED-MICA (Table 3).

TABLE 3

Equilibrium and kinetic binding parameters for α1-α2 variants. $IC_{50}$ values were derived from 4-parameter fits to the competition binding titrations (FIG. 12) and the kinetic binding parameters were derived from single exponential fits to the binding kinetics (FIG. 13). Equilibrium binding constants ($K_d$) were derived from the kinetic binding parameters using the equation $K_d = k_{OFF}/k_{ON}$.

| | | Kinetic Binding Parameters | | |
|---|---|---|---|---|
| α1-α2 Variant | $IC_{50}$ (nM) | $k_{ON}$ (M$^{-1}$s$^{-1}$) | $k_{OFF}$ (s$_{-1}$) | $K_d$ (nM) |
| WT | 19.4 | $1.3 \times 10^5$ | $1.8 \times 10^{-3}$ | 13.8 |
| WED | 4.4 | $2.9 \times 10^5$ | $1.7 \times 10^{-3}$ | 5.9 |
| 15 | 1.7 | $0.7 \times 10^5$ | $1.1 \times 10^{-4}$ | 1.5 |
| 16 | 0.7 | $2.0 \times 10^5$ | $0.9 \times 10^{-4}$ | 0.5 |
| 17 | 0.6 | $2.0 \times 10^5$ | $0.7 \times 10^{-4}$ | 0.4 |
| 18 | 0.5 | $2.3 \times 10^5$ | $0.9 \times 10^{-4}$ | 0.4 |

Importantly, the relative $IC_{50}$ differences also translated to better binding to murine NKG2D-Fc and demonstrated the ability to improve binding of soluble, modified α1-α2 domains across human and non-human NKG2D receptors, an important property for preclinical drug development.

In order to understand the kinetic basis for the altered affinities, both the on-rates and off-rates for the α1-α2 variant NKG2DLs binding to surface coated biotinylated human NKG2D were measured using biolayer interferometry (Octet) at 100 nM of each of the modified α1-α2 proteins. Consistent with results from the $IC_{50}$ ELISAs, variants 16, 17 and 18 each displayed significant reductions in the off-rate (18-fold relative to WT), which is largely responsible for the affinity increase (~30-fold relative to WT a1-a2; Table 3). Although variant 15 displayed a similar slow off-rate as did 16, 17, and 18, its on-rate was decreased, resulting in an affinity stronger than WT but weaker variants 16, 17 and 18. Because the only difference between variant 15 (SEQ ID NO.:25) and 16 (SEQ ID NO.:26) was K125N versus K125L, the mutation at position 125 clearly altered the on-rate while the decreased off-rate was attributed to the H161R mutation. Therefore, while the selected set of NKG2DL mutations (Table 1) was used to increase the α1-α2 affinity for NKG2D through significant off-rate reduction, certain substitutions also altered the on-rate resulting in a range of incremental affinity increases that we showed in this invention to have differential activity in the NK cell-mediated killing assays as described below.

The ability of the α1-α2 affinity variants to redirect NK cell-mediated lysis of FGFR3-expressing target cells was demonstrated in vitro in a calcein-release assay. The human Natural Killer (NK) cell line, NKL, was co-cultured with calcein-loaded P815 target cells ectopically expressing FGFR3 and titrated with soluble modified MIC proteins. The results in FIG. 15 showed that the killing activities of the FGFR3-specific soluble MIC variants correlated with their engineered α1-α2 affinities. Specifically, variants 16, 17, and 18 exhibited ~15-fold more killing than WT at 0.78 nM. The WED-MICA (SEQ ID NO.:20) was only slightly better than WT. Therefore, the invention describes amino acid substitutions within the α1-α2 domain that increased the NKG2D binding affinity by reducing the off-rate of soluble MIC protein binding to human NKG2D and consequentially led to the predictably increased killing potency. WED-MICA, which exhibited somewhat greater affinity than WT MICA to NKG2D by increasing on-rate rather than reducing off-rate, did not exhibit substantial improvement of target cell killing. Furthermore, WED-MICA exhibited substantially poorer binding to murine NKG2D than even WT MICA, while variants 15, 16, 17, and 18 each exhibited greater affinity for both human and murine NKG2D.

These α1-α2 NKG2DL affinity variants 15, 16, 17, and 18 enhanced the binding affinity of the attached polypeptide to the NKG2D receptor and thereby enhanced NK cell-mediated lysis of targeted cells.

Example 2. (Non-Natural α1-α2 Domains of NKG2D Ligands and the Cognate Non-Natural NKG2D Receptors to which they Bind)

The α1-α2 domain of MICA and other NKG2D ligands bind the NKG2D receptor at a known specific site (Li et al 2001; Benjamin J. McFarland, Tanja Kortemme, Shuyuarn F. Yu, David Baker, and Roland K. Strong. Symmetry Recognizing Asymmetry: Analysis of the Interactions between the C-Type Lectin-like Immunoreceptor NKG2D and MHC Class I-like Ligands. Structure, Vol. 11, 411-422, April, 2003) and drive activation of the NKG2D receptor-bearing immune cell, which consequentially kills target cells displaying MICA or other ligands. We utilized phage display to engineer non-natural α1-α2 domains of MICA by extensive mutagenesis at 57 specific sites likely to be involved in binding to NKG2D (FIG. 16). Synthetic DNA libraries coding for the α1-α2 domain and containing NNK mutagenic codons at each of the 57 amino acid positions were synthesized, individually cloned as fusions to the pIII minor coat protein of M13 phage, and phage particles displaying the mutagenized α1-α2 variants were produced in SS320 E. coli cells according to standard methodologies (Andris-Widhopf, J., Steinberger, P., Fuller, R., Rader, C., and Barbas, C. F., 3rd, 2011. Generation of human Fab antibody libraries: PCR amplification and assembly of light- and heavy-chain coding sequences, Cold Spring Harbor protocols 2011). The α1-α2 phage libraries were sorted for increased binding affinity using recombinant biotinylated NKG2D as the target antigen and cycled through iterative rounds of intentionally prolonged binding, prolonged washing, and eluting of the phage clones in order to select high affinity variants enriched for slow dissociation- or off-rates. A set of specific amino acid mutations at 9 positions in the α1-α2 domain were selected as preferred sites of amino acid substitutions with enhanced NKG2D binding affinity. We synthesized DNA polynucleotides encoding the α1-α2 domains of 8 representative variants (SEQ ID NOs: 29-36) that contained different combinations of specific mutations (FIG. 11).

The DNA polynucleotides encoding the 8 variant α1-α2 domains were amplified with PCR primers (SEQ ID NO.s: 37-38). Using Blp1 and Sap1 restriction enzymes, each was subcloned into a His-tagged α1-α2-α3-Fv fusion expression construct (SEQ ID NO.:39) to replace the sequence encoding the natural (wt) α1-α2 sequences with the mutated α1-α2 sequences. The 9 fusion proteins (SEQ ID NO.s: 40-48) were expressed in 293 cells (Expi293™ Expression System, Life Technologies, Thermo Fisher, Inc.) and affinity purified using Ni-affinity chromatography (HisTrap HP, GE Healthcare Life Sciences).

To construct NKG2D receptor proteins, we synthesized DNA encoding the extracellular domain ("ectodomain") of the wild type receptor (SEQ ID No.:49) and used PCR primers (SEQ ID NO.s: 50-51) and XbaI and BamHI sites to clone the synthetic DNA into an N-terminal His-avitag expression vector (SEQ ID NO.: 78). The His-avitag-natural NKG2D (SEQ ID NO.:52) was expressed transiently in 293 cells and purified using Ni-affinity chromatography. Following purification, the NKG2D proteins were site-specifically biotinylated using BirA to attach a biotin group onto the avitag sequence (BirA biotin-protein ligase standard reaction kit, Avidity, LLC, Aurora, Colo.).

In order to characterize and compare the kinetic binding parameters of the natural and 8 variant α1-α2 domains to natural NKG2D, we measured their binding to surface coated biotinylated natural NKG2D ectodomain using biolayer interferometry (Octet) at 100 nM of each of the α1-α2-α3-Fv fusion proteins. Results are displayed in FIG. 12.

As shown in FIG. 12, the selected α1-α2 domain mutations as fusions to heterologous polypeptides α3-Fv of SEQ ID NO.s: 42-48 increased the α1-α2 domain affinity for natural NKG2D through significant reduction of the off-rate. The off-rates ranged from 20- to more than 100-fold slower than those of wt (SEQ ID NO.:40) and the previously described MICwed α1-α2 domain variant (SEQ ID NO.:41).

Figure 4:
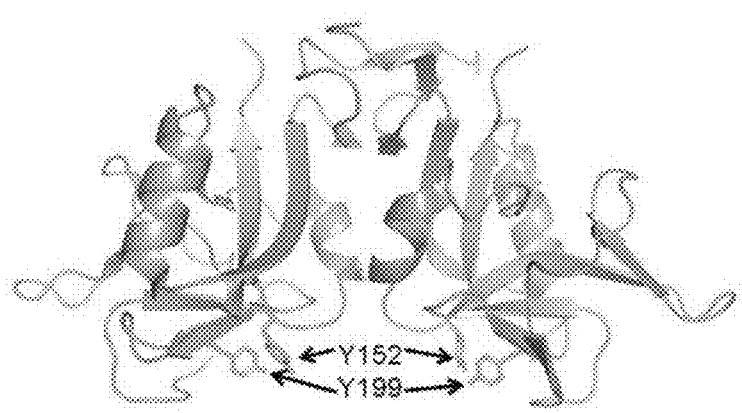
FIG. 4. Tyrosine residues Y152 and Y199 within the natural NKG2D homodimer.

In this example of the instant invention, we further demonstrated as described below, that a non-natural α1-α2 domain (DSM25, SEQ ID NO.:31, FIG. 11) that as an α1-α2-α3-Fv fusion had high affinity for and very slow off-rate from natural NKG2D (Table 2; SEQ ID NO.:43), exhibited tight binding affinity to a non-natural NKG2D receptor containing a specific mutation that abolished its binding to natural NKG2D ligands. It had been demonstrated by others that mutations at tyrosine 152 and tyrosine 199 in human NKG2D, the equivalent of positions 73 and 120 of the NKG2D ectodomain (SEQ ID NO.:49 and FIG. 4) abolish binding to the natural ligand, MICA (David J. Culpepper, Michael K. Maddoxl, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523).

To construct the non-natural NKG2D receptor proteins, we used PCR primers (SEQ ID NO.s:50-51) to clone the DNA encoding the natural NKG2D ectodomain (SEQ ID NO.:49) and insert it into the N-terminal His-avitag expression vector SEQ ID NO.:52 to produce His-avitag-NKG2D (SEQ ID NO.:53). Site-directed mutagenesis was performed on the natural NKG2D ectodomain DNA construct to introduce Y152A, Y199A, or Y152A plus Y199A mutations and created three non-natural variants of human NKG2D (SEQ ID NO.s: 54-56, respectively). The natural NKG2D and 3 non-natural NKG2D mutants with His-avitags were expressed transiently in 293 cells and purified using Ni-affinity chromatography. Following purification, the NKG2D proteins were site-specifically biotinylated using BirA to attach a biotin group onto the avitag sequence (BirA biotin-protein ligase standard reaction kit, Avidity, LLC, Aurora, Colo.).

To generate fusions of α3-Fc heterologous polypeptides to α1-α2 domain of MICwed (SEQ ID NO.:29) and DSM25 α1-α2 domain (SEQ ID NO.: 31) the DNA polynucleotides encoding the α1-α2 domains were amplified using PCR primers (SEQ ID NO.s: 37-38). Using XbaI and NcoI restriction enzymes, each was subcloned into a α1-α2-α3-Fc fusion expression construct (SEQ ID NO.:57) to replace the sequence encoding the natural (wt) α1-α2 sequences with the mutated α1-α2 sequences. The 3 fusion proteins, MICA-Fc (SEQ ID NO.: 58), MICwed-Fc (SEQ ID NO.: 59), and MICv25-Fc (SEQ ID NO.: 60) were expressed in 293 cells (Expi293™ Expression System, Life Technologies, Thermo Fisher, Inc.) and affinity purified using Protein A affinity chromatography (cat. no. 20334, Pierce Biotechnology, Rockford, Ill.).

In addition to purifying the above 3 Fc-fusion proteins NKG2D ligand-Fc fusion proteins MICB-Fc, ULBP1-Fc, ULBP2-Fc, ULBP3-Fc, and ULBP4-Fc were purchased from R&D Systems, Inc. (Minneapolis, Minn.). Binding of the different α1-α2 domain-Fc fusions to both natural and non-natural NKG2D ectodomain proteins was analyzed using a plate-based ELISA method. All of the natural and non-natural α1-α2 domain-Fc fusions were coated overnight at 4° C. onto separate wells of Maxisorp 96 well plates using a coating concentration of 2 μg/ml in phosphate-buffered saline (PBS). The plates were washed 3-times in PBS/0.05% Tween20 at 20-22° C., and blocked with 0.5% bovine serum albumin for 2 hours. The biotinylated natural and non-natural NKG2D receptor proteins were titrated against the plate-bound NKG2D ligands for 2 hours at 20-22° C., washed 3 times with PBS/0.05% Tween20 at 20-22° C., and the bound NKG2D proteins subsequently detected using a streptavidin-HRP secondary detection step and developed with 1-Step Ultra TMB Elisa. The natural form of the ectodomain of NKG2D (SEQ ID NO.:49) was capable of binding all α1-α2 domain-Fc fusions tested. The non-natural MIC-v25 α1-α2 domain ligand bound with the highest affinity ($EC_{50}$=14 nM), which was 8-fold better than MICwed and more than 100-fold better than all natural α1-α2 domain ligands tested. All ligands tested, both natural and non-natural α1-α2 domains, lost binding to the Y199A (SEQ ID NO.:55; FIG. 18, Panel B) and to the double Y152A plus Y199A (SEQ ID NO.:56) mutant NKG2D receptors. However, of all the natural and non-natural α1-α2 domain ligands tested, only the non-natural α1-α2 domain (SEQ ID NO.:31) of MICv25-Fc (SEQ ID NO.:60) retained binding to the Y152A mutant NKG2D ectodomain (SEQ ID NO.:54) with an EC50 of 50 nM.

While the binding specificity of natural NKG2D shows preference for the high affinity non-natural ligands, its potent binding to the natural NKG2D ligands, which are present on certain healthy tissues and many stressed tissues, creates an extreme risk for toxicity using current NKG2D CAR approaches (VanSeggelen et al. 2015). The Y152A non-natural NKG2D receptor specifically bound to only the protein comprised of the high affinity non-natural α1-α2 domain engineered for a markedly decreased off-rate. This prototypical example highlighted the ability of non-natural α1-α2 domains to bind non-natural NKG2D receptors, thus provided for selective control of non-natural NKG2D CARs using bispecific proteins containing the invented non-natural α1-α2 domain of NKG2D ligands.

Example 3 (Modified α1-α2 Domains of NKG2D Ligands)

This embodiment relates to additional α1-α2 NKG2DL affinity variants derived through engineering the α1-α2 domains of ULBP proteins. ULBP proteins contain α1-α2 domains, which are NKG2D ligands capable of binding to the NKG2D receptor (Cerwenka A, Lanier L L (2004). NKG2D ligands: unconventional MHC class I-like molecules exploited by viruses and cancer. *Tissue Antigens* 61 (5): 335-43. doi:10.1034/j.1399-0039.2003.00070.x. PMID 12753652). This affinity of NKG2D binding is sufficient for physiologic activation of NK cells and stimulating lysis of cells expressing native full-length ULBP proteins naturally and irreversibly tethered to the two-dimensional plasma membrane surface of a "target cell" (Cerwenka A, Lanier L L (2004). NKG2D ligands: unconventional MHC class I-like molecules exploited by viruses and cancer. *Tissue Antigens* 61 (5): 335-43. doi:10.1034/j.1399-0039.2003.00070.x. PMID 12753652). However, because engineered soluble α1-α2 domains fused to heterologous polypeptides in certain embodiments of the instant invention reversibly bind specific target antigens on the surface of a target cell, the binding affinity of the engineered ULBP α1-α2 domains to NKG2D will directly affect the stability of the artificial synapse formed between NK cells and cells expressing target antigens, as already shown by engineered soluble MIC proteins (Examples 21-2). In order to diversify the repertoire of engineered non-natural α1-α2 domains as NKG2D ligands, ULBP proteins were used as a substrate or starting point for phage display-based engineering of their NKG2D binding affinity. Despite the structural homology observed between ULBPs and MICA (Radaev, S., Rostro, B., Brooks, A G., Colonna, M., Sun, P D. (2001) Conformational plasticity revealed by the cocrystal structure of NKG2D and its class I MHC-like Ligand ULBP3. *Immunity* 15, 1039-49.), the sequence homology is <50% for the ULBP α1-α2 domains relative to MICA. Thus, we sought the identities of codon positions in ULBP α1-α2 domains that improve NKG2D binding affinity.

To engineer soluble, non-natural α1-α2 domains from ULBP proteins, ULBP2 and ULBP3 were chosen for phage display and selection of mutants with high affinity NKG2D binding. Sixty amino acid positions in the α1-α2 domain of ULBP2 (SEQ ID NO: 61), and thirty-six amino acid positions in the α1-α2 domain of ULBP3 (SEQ ID NO: 62), were chosen for extensive mutagenesis. In addition, conservative cysteine-to-serine mutations were made at C8S in ULBP2 (SEQ ID NO: 61) and C103S in ULBP3 (SEQ ID NO: 62) eliminating unpaired free cysteines in order to increase stability and function of the NKG2D ligands with attached polypeptides as well as to improve phage panning processes. Synthetic DNA libraries coding for these cysteine to serine modified α1-α2 domains, and containing NNK mutagenic codons at each of the selected amino acid positions, were synthesized, individually; cloned as fusions to the pIII minor coat protein of M13 phage; and phage particles displaying the mutagenized α1-α2 ULBP2 or ULBP3 variants were produced in SS320 E. coli cells according to standard methodologies (Andris-Widhopf, J., Steinberger, P., Fuller, R., Rader, C., and Barbas, C. F., 3rd. (2011). Generation of human Fab antibody libraries: PCR amplification and assembly of light- and heavy-chain coding sequences, Cold Spring Harbor protocols 2011). The α1-α2 phage display libraries were sorted for increased binding affinity to NKG2D using human NKG2D-Fc as the target protein, and cycled through iterative rounds of intentionally prolonged binding, prolonged washing, and eluting of the phage clones in order to select high affinity variants enriched for slow dissociation- or off-rates. For ULBP2, specific amino acid mutations were found at high frequencies at positions R80, V151, V152, and A153 in α1-α2, and were identified as preferred amino acid substitutions with enhanced NKG2D-binding affinity (FIG. 19, panel A; and Table 6).

TABLE 4

The non-natural α1-α2 domain variants selected for increased affinity to natural NKG2D receptor and the MICwed variant described previously (McFarland et al., 2003). The positions of the indicated amino acid changes referenced to the residue positions in SEQ ID NO.: 7 and the common names of the variants and their SEQ ID NOs are provided.

| a1a2 variant | aa # in wt MICA: SEQ ID NO. | 20 | 68 | 69 | 125 | 152 | 154 | 158 | 161 | 166 |
| --- | --- | --- | --- | --- | --- | --- | --- | --- | --- | --- |
| wt MICA | 42 | S | G | N | K | K | K | H | H | Q |
| MICwed | 55 | S | G | W | K | E | D | H | H | Q |
| DSM20 | 56 | S | A | W | L | Q | D | R | H | F |
| DSM25 | 57 | S | G | W | L | E | D | H | R | S |
| DSM27 | 58 | S | G | W | L | K | K | H | R | S |
| DSM28 | 59 | S | G | N | L | K | K | H | R | S |
| DSM42 | 60 | S | G | W | L | E | D | H | R | Q |
| DSM48 | 61 | S | G | W | L | A | D | I | R | A |
| DSM49 | 62 | T | Q | W | K | F | D | R | T | T |

For ULBP3, specific amino acid mutations were found at high frequencies in different locations relative to ULBP2. Positions R162 and K165 in the α1-α2 domain of ULBP3 contained specific mutations that were identified as preferred amino acid substitutions with enhanced NKG2D-binding affinity (Table 7). These modified non-natural α1-α2 domains derived from ULBP2 and ULBP3 can be used for enhanced NKG2D binding in multiple therapeutic formats as single proteins or fusions to heterologous peptides or polypeptides.

TABLE 6

Selected affinity mutations at the indicated 4 amino acid positions of the α1-α2 domain of ULBP2. The amino acids of SEQ ID NO: 61 at each of the 4 positions are shown in bold in the first row of the table. The identified affinity mutations are listed in decreasing frequency from top to bottom. All amino acids are represented by the single letter IUPAC abbreviations.

| R80 | V151 | V152 | A153 |
| --- | --- | --- | --- |
| L | D | L | E |
| W | E | W | K |
| V | Q | | G |
| F | K | | P |
| I | N | | |
| S | R | | |
| A | T | | |
| E | | | |
| P | | | |
| T | | | |

Example 4 (Binding and Cytolysis by Modified α1-α2 Domains of ULBPs Fused to Antibody Peptides)

The following example relates to attaching antibody polypeptides to NKG2DLs which were modified to significantly enhance their binding affinity to the human and murine NKG2D receptor. The α1-α2 domain of each ULBP protein is a natural ligand for the NKG2D receptor, i.e. an NKG2DL. Antibodies are highly stable glycoproteins made up of two large heavy chains and two small light chains (FIG. 1). There did not exist in the art an IgG antibody format that can directly activate immune cells using non-natural ULBP α1-α2 domains that bind more tightly than native ULBP domains to the NKG2D receptor. Furthermore, the ULBP α1-α2 domains provide alternative NKG2DLs to construct antibody fusions that may have differential in vivo properties relative to MICA α1-α2 domains. For example, an in vivo anti-drug antibody response to MICA α1-α2 domains within an antibody fusion would likely not react to or interfere with modified ULBP α1-α2 domains due to the low sequence homology between ULBP and MICA α1-α2 domains (FIG. 5). This example shows that fusions between the engineered ULBP α1-α2 NKG2D ligands (Table 6 and 7) and a heavy chain of an IgG molecule have enhanced NKG2D binding and target cell killing relative to natural ULBP α1-α2 NKG2D ligands. This further demonstrates the utility of fusions of modified α1-α2 domains to heterologous proteins or peptides.

To generate engineered α1-α2 domain fusions to antibodies, the DNA sequences encoding the C8S modified α1-α2 domains of ULBP2 (SEQ ID NO.: 61) variants R80W and V151D (SEQ ID NO.s: 63 and 64, respectively) and the C103S modified α1-α2 domain of ULBP3 (SEQ ID NO.: 62) variant R162G (SEQ ID NO.: 65) were synthesized and cloned as C-terminal fusions to the heavy chain sequence from the Her2-specific antibody (Carter, P., Presta, L., Gorman, C M., Ridgway, J B., Henner, D., Wong, W L., Rowland, A M., Kotts, C., Carver, M E., Shepard, H M. (1992) Proc Natl Acad Sci 15, 4285-9.). The resulting fusions were cloned into the mammalian expression vector pD2509 and expressed with the light chain of the parent antibody as paired full IgG antibodies. Transient expressions were carried out in HEK293 cells using the Expi293 expression system according to the manufacturer's protocol (Life Technologies), and purified using standard protein A affinity chromatography. Binding ELISAs performed on the ULBP2 and ULBP3 α1-α2 antibody heavy chain fusions demonstrated the modified ULBP2 fusions (HC_R80W and HC_V151D) and UBLP3 fusion (HC_R162G) bound with higher affinity to human NKG2D relative to their respective natural α1-α2 domains fused to the same heavy chain.

To characterize the target cell killing properties of the modified ULBP antibody fusions, the human Natural Killer (NK) cell line, NKL, was co-cultured with calcein-loaded SKBR3 target cells expressing Her2 and titrated with the engineered antibody fusion proteins. The results showed that the enhanced cytolytic (killing) activities of the Her2-specific non-natural ULBP2 and non-natural ULBP3 α1-α2-antibody fusions reflected the enhanced affinities of their engineered α1-α2 domains for NKG2D. Specifically, ULBP2 variant fusions HC_R80W and HC_V151D, and the ULBP3 variant fusion HC_R162G, killed SKBR3 cells more effectively than antibody fusions containing either native α1-α2 domain. These data further showed that modified α1-α2 variant-antibody fusions are a universal platform for enabling IgG molecules to bind tightly to NKG2D and to direct antigen-specific cell lysis.

Example 5 (Constructing Orthogonal Non-Natural α1-α2 Domains with Selective Binding to Y152A Non-Natural NKG2D)

Means to selectively control CAR-T cell therapies are highly sought after to mitigate toxicity and improve efficacy against tumors (Gill and June, op cit). Previous attempts have been made to develop CARs using the ectodomain of CD16 which can then be engaged through the Fc domain of therapeutic monoclonal antibodies, allowing for antibody-based control of CAR-T targeting (Chang et al., op cit. However, CD16-based CAR-T cells can recognize all endogenous antibody molecules in blood and tissues, and the therapeutic antibodies used to control these cells will encounter interference from endogenous CD16 receptors on NK cells. Both of these features create problems with off-tumor toxicity and poor pharmacokinetics, respectively.

To address these issues we have engineered non-natural NKG2D CAR-T cells which lack binding to all natural NKG2D ligands and can be controlled through the binding of high-affinity non-natural α1-α2 domains as demonstrated in Example 2. An additional requirement is for the non-natural α1-α2 domains to retain high affinity for non-natural NKG2D, and avoid binding to natural NKG2D domains. Thus, engineered α1-α2 domains that exhibit strong selectivity for non-natural NKG2D receptors over natural NKG2D represent an ideal system for selective control of non-natural NKG2D CAR receptors, or any receptor or protein fused to non-natural NKG2D ectodomains that can be selectively engaged by non-natural α1-α2 domains.

We employed phage display to engineer orthogonal non-natural α1-α2 domains that exhibit selective binding to the Y152A NKG2D receptor. As a starting point, three non-natural α1-α2 domains with high affinity for natural NKG2D were selected as parent domains for further mutagenesis and screening by phage display. Synthetic DNA libraries were generated for the individual α1-α2 domain variants DSM25, ULBP2 R80W, and ULBP3 R162G (SEQ ID NO.s: 31, 63, and 65), whereby codons of amino acid residues that in the bound state are positioned in close proximity to the Y152 position on the NKG2D receptor were replaced with NNK codons. DSM 25 libraries consisted of NNK positions at residues 71-75 and 155-159, ULBP2 R80W libraries with NNK codons at positions 154-159, and ULBP3 R162G libraries with NNK codons at positions 155-159. Libraries were cloned as fusions to the pIII minor coat protein of M13 phage; and phage particles displaying the mutagenized α1-α2 domain variants were produced in SS320 E. coli cells according to standard methodologies (Andris-Widhopf, J., Steinberger, P., Fuller, R., Rader, C., and Barbas, C. F., 3rd. (2011). Generation of human Fab antibody libraries: PCR amplification and assembly of light- and heavy-chain coding sequences, Cold Spring Harbor protocols 2011). The α1-α2 phage display libraries were sorted for high binding affinity to the non-natural Y152A NKG2D receptor by selectively capturing phage clones bound to biotinylated Y152A NKG2D-Fc protein in the presence of non-biotinylated natural NKG2D-Fc competitor protein. Selective clones were enriched by cycling through multiple rounds of competitive selection with increasing concentrations of non-biotinylated natural NKG2D-Fc.

After four rounds of selection, phage clones were sequenced to identify specific mutations within the NNK mutagenic regions. FIGS. 13, 14 and 15 show the selected amino acid residues that were found to be prevalent for each α1-α2 domain resulting from the Y152A NKG2D selective screening.

Figure 6:
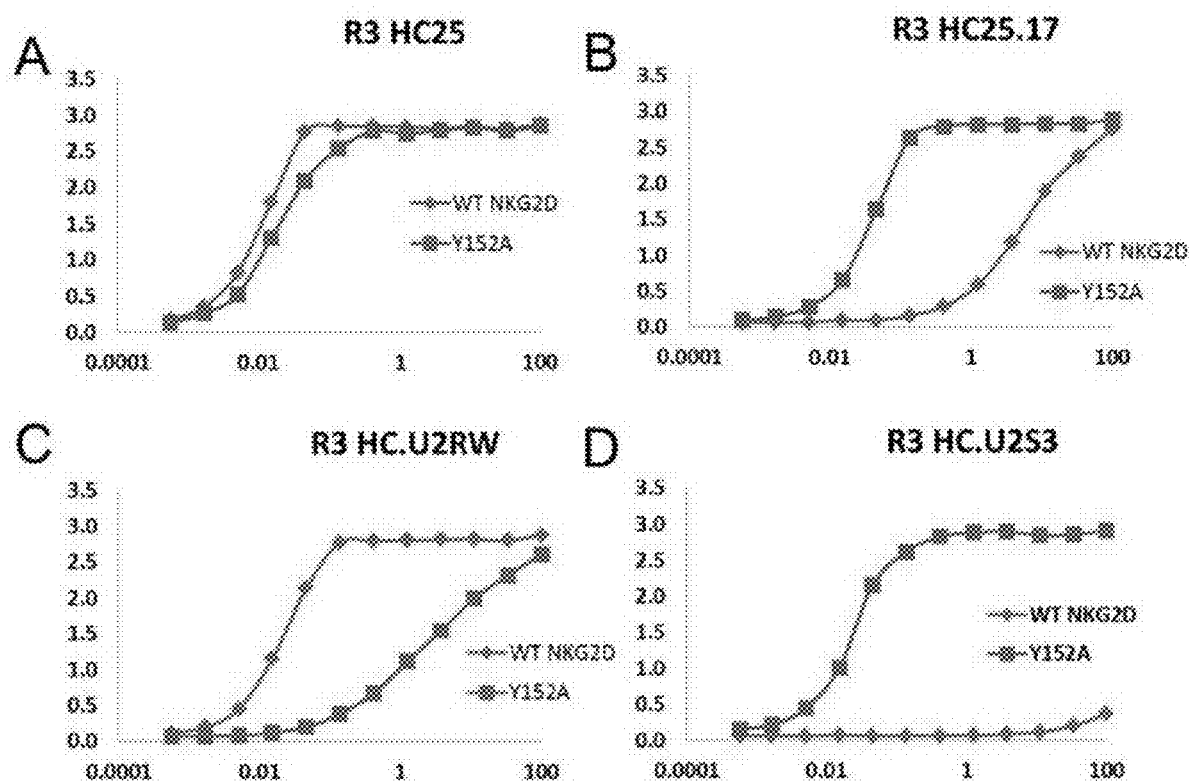
FIG. 6. ELISA results for R3 antibody fusions to non-natural α1-α2 domains selected for binding to Y152A NKG2D-Fc. (A) R3 HC25 antibody fusion is not selective for Y152A NKG2D. (B) R3 HC25.17 (SEQ ID NO.: 73) antibody fusion is selective for Y152A NKG2D over natural NKG2D-Fc. (C) R3 HC.U2RW antibody fusion is not selective for Y152A NKG2D over natural NKG2D-Fc. (D) R3 HC.U2S3 (SEQ ID NO.: 74) antibody fusion is selective for Y152A NKG2D over natural NKG2D-Fc.

To confirm the phage clones displayed proper selective binding, phages were produced for the individual clones: MICA25.17, MICA25.18, ULBP2.S1, ULBP2.S2, ULBP2.S3, ULBP3.S1 and ULBP3.S2 (SEQ ID NOs: 66, 67, 68, 69, 70, 71, and 72 respectively) and titrated against Y152A or natural NKG2D in binding ELISAs. FIG. 6, Panels A-C, demonstrated that all 7 phage clones displayed greater than 10-fold selective binding to non-natural Y152A NKG2D over natural or wild-type NKG2D.

To confirm the Y152A-selective α1-α2 domain variants retain specific binding properties within the context of antibody fusions, we cloned MICA25.17 and ULBP2.S3 as C-terminal fusions to the heavy chain of an FGFR3 specific antibody previously described (Qing et al, 2009. op cit; SEQ ID NO.s: 73 and 74, respectively). The resulting fusions were cloned into the mammalian expression vector pD2509 and co-expressed with the light chain of the parent antibody as paired full IgG antibodies (R3 HC25.17 and R3 HC.U2S3). Transient expressions were carried out in HEK293 cells using the Expi293 expression system according to the manufacturer's protocol (Life Technologies), and purified using standard protein-A affinity chromatography. ELISAs measuring the binding of R3 HC25.17 and R3 HC.U2S3 α1-α2 antibody heavy chain fusions to non-natural Y152A NKG2D and to natural NKG2D demonstrated their significantly greater binding affinity toward Y152A NKG2D relative to the natural NKG2D (FIG. 6, Panels B and D). In contrast, the antibody fusions to DSM25 and ULBP2 R80W exhibited preferred binding to natural NKG2D-Fc (FIG. 6, panels A and C). Collectively, these data demonstrated the invention of non-natural orthogonal α1-α2 domains that possessed high affinity binding to non-natural NKG2D receptors and significantly reduced binding affinity to the natural NKG2D receptor. Furthermore, fusions of orthogonal α1-α2 domains to antibody polypeptides retained their selective binding properties and can be used to redirect non-natural NKG2D receptors toward new antigens, for example in the context of CAR-T cells.

Example 6 (the Targeting and Killing Activity of CAR-T Cells with the Non-Natural NKG2D Ectodomain are Controlled Using Orthogonal α1-α2 Domains Fused to Targeting Antibodies)

To demonstrate selective control of CAR-T cells constructed with a chimeric receptor deploying the non-natural NKG2D ectodomain, we constructed CARs with either the natural NKG2D or the non-natural Y152A NKG2D ectodomains based on previous work using 4-1BB/CD3zeta CAR constructs (Campana patent 8,399,645) fusing the respective NKG2D ectodomains to the CD8 hinge region (FIG. 2) of CARs. These constructs were cloned into a lentiviral vector and expressed in primary human CD8-positive T-cells using lentiviral transduction. The resulting natural NKG2D CAR-T cells exhibited specific cell killing activity in vitro, consistent with recognition of the natural MICA ligand expressed on target cells. Specifically, the results showed that although natural NKG2D CAR-T cells killed P1 cells expressing natural MICA ligands, the non-natural Y152A NKG2D CAR-T cells were significantly disabled and exhibited much reduced killing of MICA expressing P1 cells. Furthermore, the orthogonal α1-α2 antibody heavy chain fusions, R3 HC25.17 and R3 HC.U2S3, selectively activated the non-natural Y152A CAR-T cells to kill FGFR3 expressing P1 target cells, but were not capable of redirecting the killing activity of natural NKG2D CAR-T cells. This was in contrast to the R3 HC25 and R3 HC.U2R80W α1-α2 antibody heavy chain fusions which were not selective for non-natural Y152A NKG2D and activated both natural and non-natural CAR-T cells to kill P1 target cells. These data showed non-natural orthogonal α1-α2 domains engineered to bind selectively to non-natural Y152A NKG2D specifically activated non-natural Y152A NKG2D CAR-T cells while avoiding natural NKG2D receptors.

Example 7 (Constructing Orthogonal Non-Natural α1-α2 Domains with Selective Binding to Y152A/Y199F Non-Natural NKG2D)

It had been demonstrated by others that mutations at tyrosine 152 or at tyrosine 199 in human NKG2D, the equivalent of positions 73 and 120 of the NKG2D ectodomain (SEQ ID NO.:49) can greatly reduce binding to the natural ligand, MICA (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523). We reasoned that while mutation of either tyrosine residue greatly affected the ability of NKG2D to bind to its natural ligands, simultaneous mutation at both tyrosine 152 (Y152) and tyrosine 199 (Y199) would virtually eliminate the receptor's ability to engage with all native ligands. We therefore sought to explore individual and combinatorial Y152 and Y199 substitutions and characterize them with regard to their biochemical behavior with the objective of identifying both single and double-mutant variants incapable of engaging any natural ligands. Those variants that also expressed and assembled well were of particular interest as these signified inert ligands that could be more easily produced for analysis.

Natural NKG2D (wild-type) ectodomain (NKG2D.wt, SEQ ID NO: 49) and candidate non-natural NKG2D variant ectodomains (SEQ ID NOs: 75-92)—also termed "engineered NKG2D" or "eNKG2D" were cloned as fusions to the C-terminus of human IgG1 Fc (without Fab domains), via a short factor Xa recognizable Ile-Glu-Gly-Arg linker (SEQ ID NO: 93) and are interchangeably referred to as Fc-NKG2D.wt or NKG2D.wt and Fc-eNKG2D or eNKG2D (SEQ ID NOs: 94-112). gBlocks® DNA Fragments (Integrated DNA Technologies, San Diego, Calif.), corresponding to the MHCI signal sequence (SEQ ID NOs: 113 and 114), human IgG1 Fc with linker (SEQ ID NO: 115), and NKG2D ectodomain variants (SEQ ID NOs: 116-124) were synthesized and inserted into pD2610-V12 (ATUM, Newark, Calif.). DNA constructs exploring substitutions at Y152, Y199, or a combination of Y152/Y199 mutations (Table 1) were expressed transiently in Expi293™ cells (ThermoFisher Scientific, Waltham, Mass.) and secreted protein purified by Protein A affinity chromatography (cat. no. 20334, Pierce Biotechnology, Rockford, Ill.). Eluted material was characterized by size-exclusion chromatography (SEC) on Akta Pur Superdex columns and correctly assembled, size-appropriate material was fractionated and isolated from aggregate peaks prior to inclusion in assays.

Figure 2:
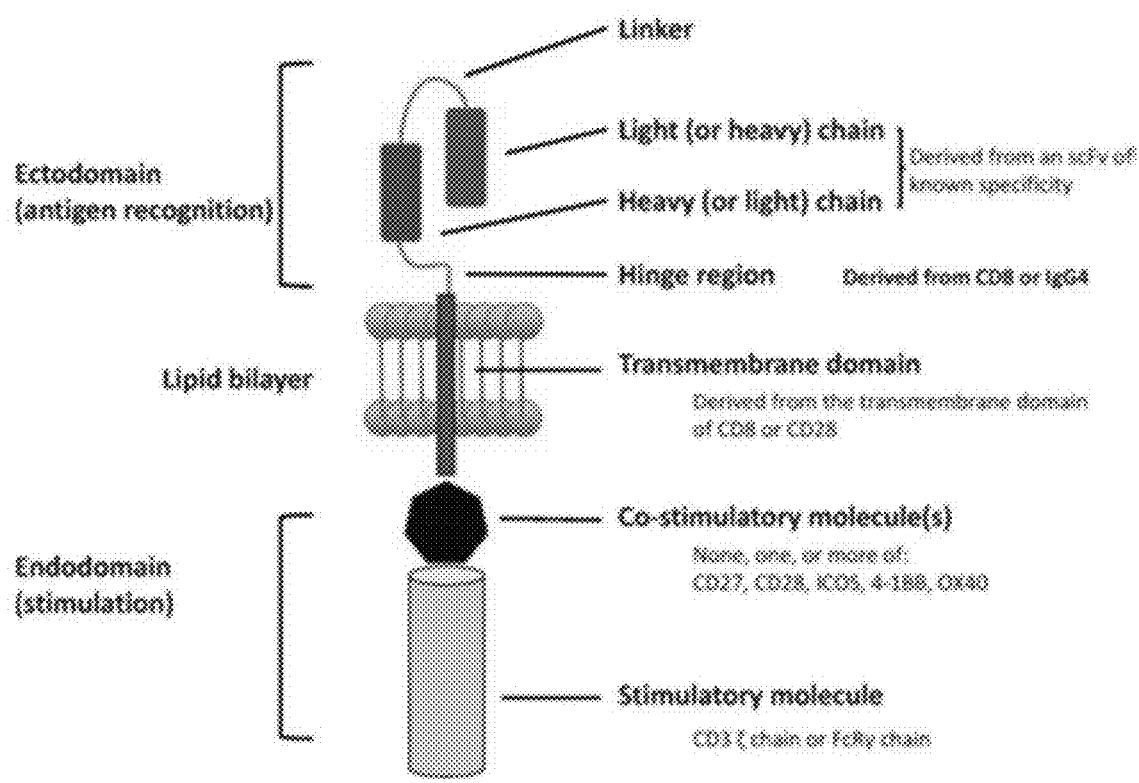
FIG. 2. Anatomy of a typical CAR (Gill & June, 2015, op cit).

SEC characterization of purified NKG2D.Y199A-Fc fusion revealed a composition of predominantly aggregated material (FIG. 2). In comparison, both the natural Fc-NKG2D fusion and Fc-NKG2D.Y152A fusion material were distinguished by a discrete, non-aggregated peak that was readily differentiated from more rapidly migrating aggregate. The effect of the Y199A mutation on aggregation was also apparent in the Y152A/Y199A double-mutant Fc-NKG2D fusion variant, indicating that it had an over-riding influence on protein misfolding (FIG. 2). This aspect of including Y199A with any combination of Y152 mutations in NKG2D variants therefore presented a challenge for the production of material necessary for subsequent engineering efforts and raised a concern about assembly and presentation on a cell surface. As a consequence, an effort was made to explore other substitutions at Y152 and Y199 that could be combined to yield a more robust molecule. eNKG2D combinatorial Y152 and Y199 mutant candidates were examined as Fc fusions and detailed in (Table 1). In addition, all purified and expressed Fc-eNKG2D fusion candidates were profiled by SEC and their chromatograms revealed varying levels of aggregate formation (FIGS. 2 and 3, Table 1). Of the single amino acid substitutions explored at residue 152 alanine, serine, threonine, and valine all did not impact assembly of the Fc-NKG2D molecule although Y152-leucine (Y152L) resulted in highly aggregated material. Similar to alanine, neither glutamate nor aspartate were tolerated at position 199, although phenylalanine only modestly increased aggregate formation. Of the combinations of mutations that were explored, Y152A/Y199F, Y152S/Y199F, Y152T/Y199F, and Y152F/Y199F did not negatively impact the desired dimer formation, whereas other combinations resulted in increased aggregation.

Example 8: (Generation of Antibody-Based Bispecific Molecules, "MicAbodies", with Non-Natural NKG2D Ligand Variants)

To generate non-natural MicA variants fused to human IgG1, the DNA polynucleotides encoding the α1-α2 domains of, for example, MICwed (SEQ ID NO: 7) and MIC25 (SEQ ID NO: 31), were PCR amplified using primers that also introduced the polynucleotide encoding either an APTSSSGGGGS linker for fusion to C-terminal kappa light chain (SEQ ID NO: 135) or for a GGGS linker for fusion to C-terminal heavy chain of human IgG1 (SEQ ID NO: 136). Furthermore, two mutations were introduced into the CH2 domain of the heavy chain—D265A/N297A (Kabat numbering)—that reduce binding to all FcγR receptors thus eliminating antibody-dependent cell cytotoxicity (ADCC) function (Shields et al., 2001 *JBC*, 276:6591-6604]. The polynucleotide encoding the α1-α2 domain of wild-type ULBP2 (ULBP2.wt) without its GPI-linkage (SEQ ID NO: 61) was similarly cloned and fused to the DNA polynucleotides encoding the linkers and the IgG1 heavy chain or light chain. These bispecific antibodies— termed "MicAbody™" in the singular, "MicAbodies" in the plural—are bivalent for the fused α1-α2 domain. Examples of antibodies used to generate MicAbodies for the purposes of exploring eNKG2D engineering include but were not limited to trastuzumab (SEQ ID NOs: 137 and 138) and ritixumab (SEQ ID NOs: 139 and 140) and subsequently termed "trastuzumab-MicAbody" and "rituximab-MicAbody" respectively. The fusion constructs were inserted individually into pD2610-V12 (ATUM, Newark, Calif.) via Gibson cloning (New England Biolabs Inc., Ipswich, Mass.). For a given antibody recognizing a specific antigen, the plasmid encoding the heavy chain and the plasmid encoding the light chain fused to either natural or non-natural NKG2D ligand were co-transfected for transient expression in Expi293™ cells (ThermoFisher Scientific, Waltham, Mass.). Alternatively, the plasmid encoding the heavy chain fused to either natural or non-natural NKG2D ligand and the plasmid for light chain were co-transfected. Secreted bispecific antibodies were purified by Protein A affinity chromatography (cat. no. 20334, Pierce Biotechnology, Rockford, Ill.), eluted material was characterized by size-exclusion chromatography (SEC) on Akta Pur Superdex columns, and fractionation performed as needed. In addition, SDS-PAGE analysis was performed on purified samples to verify the expected molecular weights of the fused heavy chain and fused light chain species.

Example 9: (Identifying Modified NK2GD Variants Incapable of Binding to Either Natural NKG2D-Binding Ligands or to Non-Natural Ligands that have Enhanced Binding to Wild-type NKG2D)

The binding affinities of α1-α2 variants to the extracellular domains of natural (wild-type) NKG2D and non-natural eNKG2D proteins were analyzed using a plate-based ELISA method. Each of the SEC fractionated natural Fc-NKG2D and non-natural Fc-eNKG2D fusions were coated overnight at 4° C. onto separate wells of Nunc Maxisorp 96 well plates (Thermo Fisher Scientific, Waltham, Mass.) using a coating concentration of 1 µg/mL in phosphate-buffered saline (PBS). The plates were washed three times in PBS/0.05% Tween-20 (PBS-T) at 20-22° C., and blocked with 0.5% bovine serum albumin in PBS (PBS-B) for 2 hours at 20-22° C. MicAbodies were titrated against the plate-bound natural or non-natural Fc-eNKG2D fusions for 60 minutes at 20-22° C. in PBS/0.5% bovine serum albumin (BSA)/0.05% Tween-20 (PBS-BT), washed 3 times with PBS-T at 20-22° C., and the bound bispecific proteins detected using an HRP-conjugated anti-human kappa in PBS-BT (Abcam, Cambridge Mass.) and developed with 1-Step™ Ultra TMB ELISA Substrate Solution (Thermo Fisher Scientific, Waltham, Mass.). The binding of the ULBP2.wt rituximab-MicAbody (SEQ ID NOs: 139 and 141) discriminated between wild-type NKG2D and eNKG2D variants with reduced binding to the latter, and ligand variants—MICwed (SEQ ID NOs: 20 and 78) and MIC25 (SEQ ID NOs: 138 and 80)—were more stringent at identifying eNKG2D variants with abolished ligand binding. The binding behaviors for each eNKG2D variant against all three bispecific ligands revealed the combinations of NKG2D modifications that led to the greatest reduction in binding of wild-type and variant ligands and enabled the selection of lead inert NKG2D variants.

Additional biophysical analysis of eNKG2D variant binding to ligands was also performed with Bio-Layer Interferometry (BLI) using the ForteBio Octet system (all ForteBio LLC, Fremont, Calif.). For these experiments human NKG2D ligands MICA-Fc, MICB-Fc, ULBP1-Fc, ULBP2-Fc, ULBP3-Fc, and ULBP4-Fc were purchased from R&D Systems, Inc. (Minneapolis, Minn.). Ligands in the MicAbody format were captured on anti-human IgG Fc capture (AHC) biosensor tips. After a baselines were established, tips were exposed to a titration series of Fc-eNKG2D fusion proteins ranging from 300 nM to 0.41 nM and association/dissociation kinetics monitored with all steps performed in PBS-BT. Subsequently, Fc-eNKG2D fusion proteins were captured onto AHC tips and MicAbodies were titrated to characterize binding kinetics.

To determine the maximum response as defined by binding of natural NKG2D to either MICwed or MIC25, natural Fc-NKG2D fusions were captured onto AHC biosensors and 20 nM trastuzumab-MICwed or 20 nM trastuzumab-MIC25 MicAbodies were incubated for two minutes and then dissociation kinetics observed for 30 seconds. Binding analysis under the same conditions was then performed with Fc-eNKG2D fusion receptors as the capture agent, and the level of binding for each eNKG2D ranked as a percentage of the maximal binding response established by Fc-NKG2D.wt (Table 2). For MICwed, the responses of all single mutant Fc-eNKG2D variants, except for Y199F, were diminished to 50%. Y199F maintained 100% binding response. However, all double-mutant Fc-eNKG2D variants had completely abolished binding to MICwed. For MIC25, all single mutant Fc-eNKG2D variants and Y152V/Y199F maintained 100% binding response relative to wild-type Fc-NKG2D binding. However, binding was reduced to 50% with several of the double-mutant Fc-eNKG2D variants including Y152A/Y199F, Y152S/Y199F, and Y152T/Y199F.

ELISA assays with Fc-eNKG2D fusions as capture agents were performed with ULBP2.wt, MICwed, MIC25 MicAbodies titrated starting at 300 nM. $EC_{50}$ values were calculated when possible using GraphPad Prism (Table 11).

TABLE 11

$EC_{50}$ values (nM) for Fc-eNKG2D ELISAs.

| | | | MicAbody | |
|---|---|---|---|---|
| | Fc-eNKG2D | ULBP2.wt | MICwed | MIC25 |
| wt | NKG2D.wt Y\|Y | 1.41 | 0.0067 | ~0.0039 |
| Y152 | eNKG2D A\|Y | 27.86 | 4.30 | 0.0057 |
| | eNKG2D2 S\|Y | 34.78 | 4.16 | 0.0056 |
| | eNKG2D3 T\|Y | 31.14 | 4.33 | 0.0056 |
| | eNKG2D4 V\|Y | 35.78 | 4.84 | ~0.0043 |
| | eNKG2D14 L\|Y | 87.63 | 9.39 | 0.010 |
| Y169 | eNKG2D1 Y\|F | 23.08 | 0.32 | 0.0048 |
| | eNKG2D10 Y\|D | nt | nt | nt |
| | eNKG2D11 Y\|E | nt | nt | nt |
| Y152\|Y199 | eNKG2D5 A\|F | nb | 280.5 | 0.79 |
| | eNKG2D6 L\|F | nb | nb | 0.37 |
| | eNKG2D7 S\|F | nb | 347.3 | 20.94 |
| | eNKG2D8 T\|F | nb | 570.6 | 4.51 |
| | eNKG2D9 V\|F | nb | 90.0 | 0.43 |
| | eNKG2D15 F\|F | 57.05 | 31.3 | 0.046 |
| | eNKG2D12 D\|D | nb | nb | nb |
| | eNKG2D13 E\|E | nb | nb | nb | nt = not tested; nb = no binding or very low binding even at 300 nM so $EC_{50}$ value not calculated Natural NKG2D bound to ULBP2, MICwed, and MIC25-based MicAbodies with affinities calculated as Kds values of 1.4, 0.007, and 0.005 nM, respectively. While affinity was diminished for ULBP2 and MICwed MicAbodies with all single mutant eNKG2D candidates, binding of MIC25 to eNKG2D candidates was retained. However, all double-mutant eNKG2D candidates had eliminated or significantly reduced binding to all three ligands—ULBP2, MICwed, and MIC25—in Micabody formats.

eNKG2D variants eNKG2D5 (Y152A/Y199F), eNKG2D7 (Y152S/Y199F), eNKG2D8 (Y152T/Y199F), and eNKG2D9 (Y152V/Y199F) had reduced or abolished binding to ULBP2, MICwed, and MIC25-based MicAbodies by both Octet analysis and ELISA (Table 2 and 3). Furthermore, eNKG2Ds 5, 7, and 8 had the least amount of aggregation, suggestive of more robust protein assembly upon 293T expression (Table 1). eNKG2D5 (SEQ ID NO: 102) was examined more closely for binding to wild-type ligands as MicAbodies captured on Octet AHC tips. Single mutant Fc-NKG2D.Y152A (SEQ ID NO: 95) had reduced binding to all natural ligands relative to natural (SEQ ID NO: 94) NKG2D (FIG. 5). The response curve for binding of eNKG2D5 (Y152A/Y199F) was reduced even further relative to Y152A eNKG2D. eNKG2D5 (Y152A/Y199F, henceforth referred to as "AF" or "NKG2D.AF") was chosen as the lead NKG2D variant for which to engineer cognate selective, orthogonal, non-natural ligands.

Example 10: (Constructing Orthogonal Non-Natural α1-α2 Domains with Selective Binding to Non-Natural NKG2D.AF Ectodomain)

We employed phage display to engineer orthogonal non-natural α1-α2 domains that exhibit selective binding to the NKG2D.AF (SEQ ID NO: 102) receptor. As a starting point, the non-natural ULBP2.R80W α1-α2 domain (FIG. 1B; SEQ ID NO: 142) with high affinity for natural, wild-type NKG2D (NKG2D.wt) ectodomain was selected as the parent domain for further mutagenesis and screening by phage display. Synthetic DNA libraries were generated for the α1-α2 domain of ULBP2.R80W (SEQ ID NO: 108) which additionally has a C8S mutation to eliminate the potential for disulfide linkages. Codons of amino acid residues of the ligand that in the bound state are positioned in close proximity to the Y152 and Y199 positions on the natural NKG2D receptor were replaced with NNK codons; the libraries consisted of NNK codons at positions 154-159. Libraries were cloned as fusions to the pIII minor coat protein of M13 phage, and phage particles displaying the mutagenized α1-α2 domain variants were produced in SS320 *E. coli* cells according to standard methodologies (Andris-Widhopf, J., Steinberger, P., Fuller, R., Rader, C., and Barbas, C. F., 3rd. (2011). These α1-α2 phage display libraries were sorted for high binding affinity to the non-natural NKG2D.AF receptor by selectively capturing phage clones bound to biotinylated Fc-NKG2D.AF protein in the presence of non-biotinylated natural Fc-NKG2D.wt competitor protein. Selective clones were enriched by cycling through multiple rounds of competitive selection with increasing concentrations of the non-biotinylated natural Fc-NKG2D.

After four rounds of selection, phage clones were individually arrayed in 96-well format, spot ELISAs were performed to verify preferred differential binding to plate-bound non-natural NKG2D.AF versus NKG2D.wt. Bound phages were detected with biotinylated M13 phage coat protein monoclonal antibody E1 (ThermoFisher Scientific, Waltham, Mass.), streptavidin-HRP detection (R&D Systems, Minneapolis, Minn.), and 1-Step Ultra TMB ELISA development (ThermoFisher Scientific, Waltham, Mass.). The spot ELISA signal for each clone was expressed as a ratio of phage binding NKG2D.AF to phage binding NKG2D.wt. Those phages with a ratio greater than or equal to 14 were sequenced to identify the specific mutations within the NNK mutagenized regions. In instances where multiple clones representing the same sequence were identified, the ratio of ELISA signals was plotted, and consistency of phage clones was verified by the clustering of data points (data not shown).

Thirty of the variants identified in ELISAs were expanded in individual monocultures to generate high titer micro-batches of phage. Purified phage concentrations were normalized to an $OD_{268}$=0.5 then subject to 1:3 dilution series against plate-bound Fc-NKG2D.AF or Fc-NKG2D.wt with phage detection and ELISA development performed as described above. All thirty variants assayed in this manner consistently demonstrated selective binding to NKG2D.AF with little to no binding to NKG2D.wt even at the highest concentrations of phage assayed. The selected phages also exhibited a shift of two or more logs of phage concentration to achieve half-maximal binding between NKG2D.AF and NKG2D.wt.

To confirm that the NKG2D.AF-selective α1-α2 domain variants retained specific binding properties in the context of antibody fusions, 21 variants (FIG. 12; e.g. SEQ ID NOs: 143-150) were cloned as C-terminal fusions with an APTSSSGGGGS linker to the light chain of the rituximab antibody. The resulting fusions were cloned into the mammalian expression vector pD2610-V12 (ATUM, Newark, Calif.) via Gibson cloning (New England Biolabs Inc., Ipswich, Mass.) and co-expressed with the heavy chain of the parent antibody as paired full IgG antibodies. Transient expressions were carried out in Expi293™ cells (ThermoFisher Scientific, Waltham, Mass.) according to the manufacturer's protocol, and purified using standard protein-A affinity chromatography (cat. no. 20334, Pierce Biotechnology, Rockford, Ill.). ELISAs measuring the binding of each variant ULBP2 α1-α2 antibody fusions to non-natural Fc-NKG2D.AF and to natural Fc-NKG2D.wt demonstrated their significantly greater binding affinity toward NKG2D.AF relative to the natural NKG2D.wt (FIG. 16).

Collectively, these data demonstrated the invention of non-natural, orthogonal α1-α2 domains that possessed high affinity binding to the non-natural NKG2D.AF receptor and significantly reduced binding affinity to the natural NKG2D receptor. Furthermore, fusions of these orthogonal α1-α2 domains to antibody polypeptides retained their selective binding properties and were used, for example, in the context of chimeric antigen receptor (CAR) T cells, to redirect non-natural NKG2D.AF receptors toward specific antigens.

Example 11: (Identifying Non-Natural NKG2D Ligands that can Discriminate Between Non-Natural NKG2D Receptor Variants by Selectively Binding One or the Other)

Phage display to engineer orthogonal non-natural α1-α2 domains with selective binding to NKG2D.Y152A (henceforth referred to as NKG2D.YA, receptor was performed with non-natural ULBP2.R80W α1-α2 domain (SEQ ID NO: 142) as the starting point as described above. The α1-α2 phage display libraries were panned for high binding affinity to the non-natural Fc-NKG2D.YA receptor by selectively capturing phage clones bound to biotinylated Fc-NKG2D.YA (SEQ ID NO: 95) protein in the presence of non-biotinylated natural Fc-NKG2D.wt (SEQ ID NO: 94) competitor protein. Additional phage clone validation work resulted in the identification of variants with preferential binding to Fc-NKG2D.YA versus Fc-NKG2D.wt (FIG. 17).

ULBP2.S3 (SEQ ID NO: 151), for example, consistently demonstrated selective binding by ELISA and Octet analysis (both in monomeric His-tagged and bispecific antibody fused format) to non-natural NKG2D.YA relative to natural NKG2D.wt. This represented a distinct form of the invention of non-natural orthogonal α1-α2 domains possessing high affinity binding to non-natural NKG2D receptors (in this case NKG2D.YA as opposed to NKG2D.AF as in Example 2). Furthermore, fusions of orthogonal α1-α2 domains to antibody polypeptides retained their selective binding properties and were used to selectively redirect non-natural NKG2D receptors towards specific molecules determined by fused heterologous peptides such as antibodies.

Figure 8:
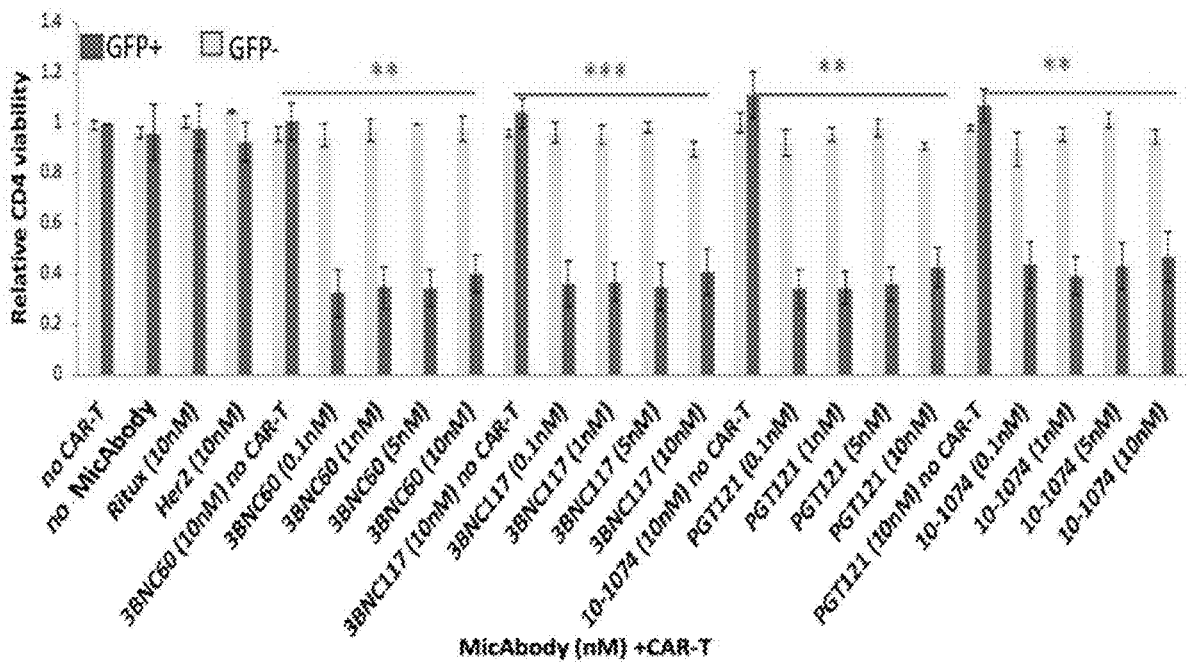
FIG. 8. Specific killing of R5 virus infected primary CD4 cells by CAR-T combined with specific HIV MicAbody. One million primary tonsil derived cells infected with Bal-GFP R5 virus (~$1 \times 10^4$ infected cells) were incubated with $1 \times 10^5$ CAR-T cells in the presence of different concentrations of the HIV-specific MicAbodies or the B-cell specific CD20-targeting MicAbody or a HER2-targeting MicAbody (Her2). Cells were stained 24h later and analyzed by flow cytometry. Cells were gated on single cell/live/CD3+/CD8− and either GFP+ or GFP−. Results averaged from 4 studies are shown.
Figure 9:
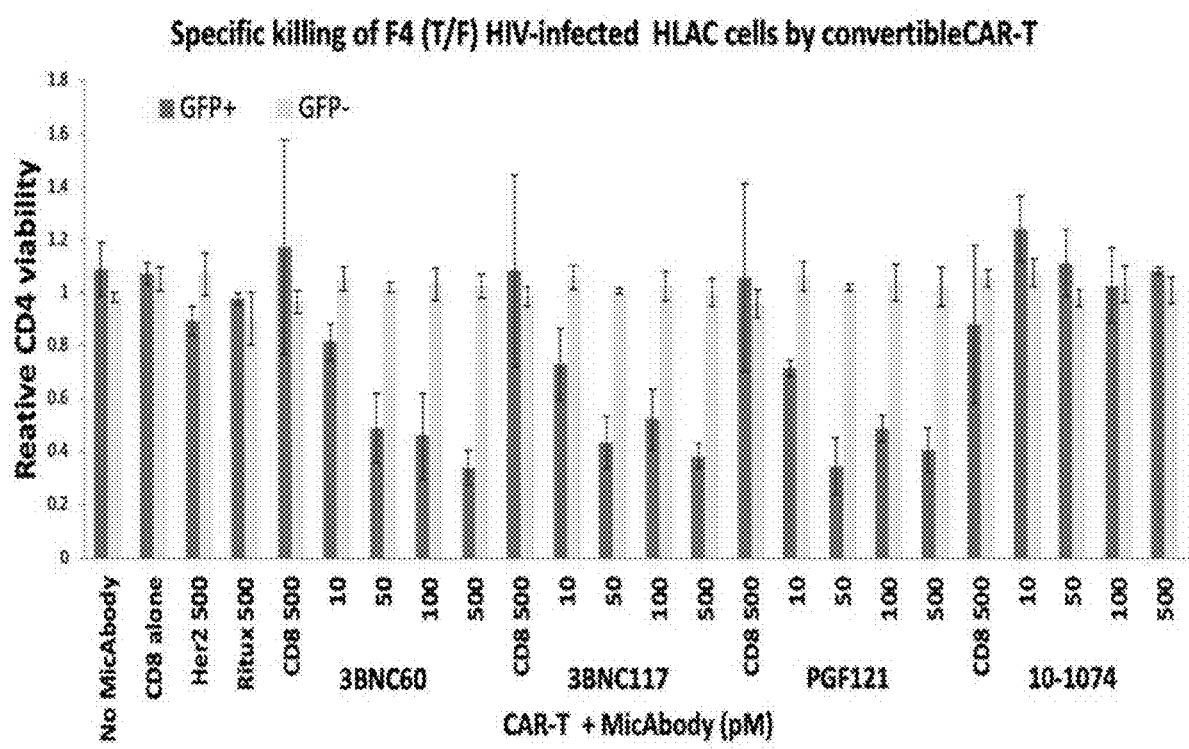
FIG. 9. Specific killing of F4 transmitted/founder virus infected primary CD4 cells by CAR-T combined with specific HIV MicAbody. One million primary tonsil derived cells infected with F4-GFP (T/F) virus (~$1 \times 10^4$ infected cells) were incubated with $1 \times 10^5$ convertible CAR-T cells in the presence of different concentrations of the 4 distinct HIV-specific MicAbodies, the CD20-targeting MicAbody (Ritux) or the HER2-targeting MicAbody (Her2). Cells were stained 24 h later and followed with flow cytometry. Cells were gated on single cell/live/CD3+/CD8− and either GFP+ or GFP−.

In order to determine whether a non-natural α1-α2 domain with selective binding to NKG2D.YA (ULBP2.S3, SEQ ID NO: 151) and the non-natural α1-α2 domains with selective binding to NKG2D.AF could discriminate between these two non-natural receptor variants, titration ELISAs were performed. All 21 of the selected α1-α2 variants that bound NKG2D.AF were directly compared for binding to NKG2D.AF versus NKG2D.YA. Of these, four demonstrated the properties of inability to bind NKG2D.wt, strong affinity for NKG2D.AF, and greatly reduced (15-20 fold) or eliminated binding to NKG2D.YA relative to NKG2D.AF. These four non-natural ULBP2 α1-α2 variants—ULBP2.C, ULBP2.R, ULBP2.AA, and ULBP2.AB (SEQ ID NOs: 143, 145, 147, and 149)—were also examined for alterations in predicted immunogenicity profile relative to the wild-type ULBP2 peptide sequence (SEQ ID NO: 61) using the NetMHC4.0 Server (for peptide-MHC class I binding querying against all the HLA supertype representatives with 9-mer peptide analysis; http://www.cbs.dtu.dk/services/NetMHC/) and NetMHCII 2.3 Server (for peptide-MHC class II binding querying against HLA-DR, HLA-DQ, HLA-DP haplotypes with 15-mer peptide analysis; http://www.cbs.dtu.dk/services/NetMHCII/), both algorithms which were developed by the Technical University of Denmark (http://www.bioinformatics.dtu.dkl; Andreatta M and Nielsen M, Gapped sequence alignment using artificial neural networks: application to the MHC class I system, 2016 *Bioinformatics,* 32:511, PMID: 26515819; Jensen K K, Andreatta M, Marcatili P, Buus S, Greenbaum J A, Yan Z, Sette A, Peters B, and Nielsen M, Improved methods for predicting peptide binding affinity to MHC class I molecules, 2018 *Immunology,* PMID: 29315598). The mutations incorporated into ULBP2.C, ULBP2.R, and ULBP2.AB did not increase predicted immunogenicity while that of ULPB2.AA was increased slightly for a few haplotypes (FIGS. 8 and 9). As a consequence of the specificity of ULBP2.R for NKG2D.AF and its lack of predictable immunogenicity, ULBP2.R was selected for further ELISA analysis to directly compare its binding behavior with that of ULBP2.S3 (the NKG2D.YA-selected, non-natural, orthogonal ligand), ULBP2.R80W (non-natural ligand with enhanced affinity for wild-type NKG2D), and wild-type ULBP2 (ULBP2.wt). Binding of the four rituximab-MicAbody reagents (SEQ ID NOs: 139 and 151, 139 and 152, 153 and 140, and 139 and 141 as heavy chain and light chain for ULBP2.R, ULBP2.S3, ULBP2.R80W, and ULBP2.wt, respectively) was assayed against wild-type NKG2D (NKG2D.wt) and the two inert, non-natural variants NKG2D.YA and NKG2D.AF. The data demonstrated that NKG2D.YA-selected variant ULBP2.S3 as a MicAbody bound with high affinity to NKG2D.YA but did not engage NKG2D.AF or natural NKG2D. Furthermore, the NKG2D.AF-selected variant ULBP2.R in MicAbody format bound with high affinity to NKG2D.AF but did not engage NKG2D.YA or natural NKG2D. These results demonstrated the tremendous potential of exploring the NKG2D-MIC ligand axis and for developing unique pairs of novel, selective non-natural NKG2D receptors and their respective, cognate non-natural MIC ligand binding partners.

Example 12: (the Targeting and Killing Activity of CAR-T Cells Expressing the Non-Natural NKG2D.AF Ectodomain are Controlled by Orthogonal α1-α2 Domains Fused to Heterologous Targeting Polypeptides)

Means to selectively control CAR-T cell therapies are highly sought after to mitigate toxicity and improve efficacy against tumors (Gill and June, op cit). Previous attempts have been made to develop CARs using the ectodomain of CD16 which can then be engaged through the Fc domain of therapeutic monoclonal antibodies, allowing for antibody-based control of CAR-T targeting (Chang et al., op cit). However, CD16-based CAR-T cells can recognize nearly all endogenous antibody molecules in blood and tissues, and the therapeutic antibodies used to control these cells will encounter competition from endogenous CD16 receptors on NK cells, PMN's, monocytes and macrophages. Both of these features contribute problems of off-tumor toxicity and poor pharmacokinetics, respectively.

Natural NKG2D ligands are present on certain healthy tissues and many stressed tissues, creating an extreme risk for toxicity using current NKG2D CAR approaches (Van-Seggelen et al. 2015). The Y152A non-natural NKG2D receptor specifically bound to non-natural α1-α2 domain NKG2D ligands constituting an example of a means by which the activity of a non-natural NKG2D CAR could be selectively controlled using bispecific proteins comprised of the invented non-natural α1-α2 domain of NKG2D ligands.

We engineered CAR-T cells with a Receptor comprised of a modified Y152A/Y199F ("AF") ectodomain of NKG2D which lacks binding to all natural NKG2D ligands or previously described non-natural α1-α2 domains orthogonal and cognate to Y152A modified NKG2D (NKG2D.YA). The invented cognate non-natural α1-α2 domains bound with high affinity to the non-natural NKG2D.AF ectodomain and avoided binding to natural NKG2D ectodomains and to the NKG2D.YA ectodomain. Thus, engineered α1-α2 domains that exhibited strong selectivity for non-natural NKG2D.AF ectodomain over natural NKG2D and non-natural NKG2D.YA represent an ideal system for selective control of non-natural NKG2D CAR receptors, or any receptor or protein fused to non-natural NKG2D ectodomains that can be selectively engaged by the non-natural α1-α2 domains of the instant invention. The instant invention further enables single cells expressing two distinct CARs—one comprised of NKG2D.YA and the other of NKG2D.AF—each signaling with distinctly different intracellular domains. These distinct CARs would possess independent, dual controls of the cell's activities by extracellular exposure to the respective, cognate orthogonal MicAbody or another non-antibody fusion polypeptide.

To demonstrate selective control of CAR-T cells constructed with a chimeric receptor deploying the non-natural NKG2D.AF ectodomain, we constructed CARs with either the natural NKG2D.wt (SEQ ID NO: 49), non-natural NKG2D.YA (SEQ ID NO: 54), or the non-natural NKG2D.AF (SEQ ID NO: 154) ectodomains based on previous work using 4-1BB/CD3zeta CAR constructs (Campana patent 8,399,645) fusing the respective NKG2D ectodomains to the CD8 hinge region of CARs (SEQ ID NOs: 155, 157, 159). These constructs (SEQ ID NOs: 156, 158, 160) were cloned into a lentiviral vector and expressed in primary human CD8-positive T cells using lentiviral transduction. HeLa cells have constitutively upregulated levels of MIC ligands on their surface including MICA, MICB, ULBP3, and ULBP2/5/6 (the antibody used to ascertain this cannot distinguish between these three ULBPs; Human ULBP-2/5/6 Antibody, R&D Systems, Minneapolis, Minn.). HeLa cells were transfected to also overexpress either natural ULBP1 or the NKG2D.AF-selected variant ULBP2.R on their surface, and these cells were used as a target for in vitro killing assays. HeLa target cells were pre-loaded with calcein and exposed to NKG2D.wt-CAR, NKG2D.YA-CAR, or NKG2D.AF-CAR CD8 cells at increasing effector to target (E:T) ratios for five hours, after which the amount of calcein released into the supernatant was quantified and normalized to the total calcein released upon detergent treatment. Due to the elevated levels of MIC ligands naturally expressed on the surface of HeLa cells, the CD8 cells expressing natural NKG2D (NKG2D.wt) as the CAR engaged the HeLa cells via this over-expressed natural ligand and effected cytolysis. However, both the NKG2D.YA- and NKG2D.AF-CAR transduced CD8 cells demonstrated very little lysis of natural HeLa cells even at high E:T ratios, a level of activity that is on par with untransduced CD8 T cells. When ULBP1 is overexpressed on the surface of HeLa cells, only the NKG2D.wt-CAR CD8 T cells significantly lysed them. There is some additional killing at high E:T ratio with NKG2D.YA-CAR cells, but this is non-existent with NKG2D.AF-CAR cells showing that the double mutation Y152A/Y199F renders NKG2D even more inert than the single Y152A mutation. In HeLa cells over-expressing the NKG2D.AF-selective non-natural ULBP2.R, NKG2D.wt-CAR cells direct lysis (due to recognition of endogenous MIC ligands) while NKG2D.AF-CAR cells directed significant levels of lysis consistent with engagement of the receptor and its selective ligand.

In order to demonstrate that lysis of either NKG2D.YA- or NKG2D.AF-CAR cells could only be directed by the appropriate, cognate targeting MicAbody, Ramos cells were used as a target for cytolysis in combination with rituximab-based MicAbodies linked to either non-natural ULBP2.S3 or ULBP2.R orthogonal ligands. The rituximab-ULBP2.S3 MicAbody could direct the cell killing activity of NKG2D.YA-CAR CD8 cells but not NKG2D.AF-CAR cells, while the rituximab-ULBP2.R MicAbody could direct the activity of NKG2D.AF-CAR but not NKG2D.YA-CAR cells. This further demonstrates the selectivity of the two non-natural ULBP2 variants for their cognate non-natural NKG2D variants for which they were engineered as preferred partners. In order to demonstrate the specificity of the antibody portion of the MicAbody, in vitro killing assays were performed with NKG2D.AF-CAR CD8 cells that were pre-armed by incubation with either rituximab-ULBP2.R, trastuzumab-ULPB2.R (SEQ ID NOs: 95 and 133, heavy and light chain, respectively), or an equimolar combination of the two at a saturating total concentration of MicAbody. After unbound MicAbody was removed by washing, the CD8 cells were applied to either Ramos cells (expressing CD20, the target of rituximab) or to CT26-Her2 (a mouse cell line transfected to express human Her2) that had been pre-loaded with calcein. After a two hour incubation at two different E:T ratios, the amount of calcein released was quantified. When cells were pre-armed with rituximab-MicAbody, only Ramos cells were lysed while trastuzumab-MicAbody directed cytolytic activity only against CT26-Her2 cells. However, when NKG2D.AF-CAR CD8 cells were simultaneously pre-armed with both rituximab- and trastuzumab-ULBP2.R MicAbodies, both target cells lines were lysed demonstrating that these CAR cells—by virtue of the selective, privileged partnering that has been engineered between receptor and ligand—were readily multiplexed and thereby directed to engage different tumor targets simultaneously.

Example 13: (Killing of Human Tonsillar CD4 T Cells Productively Infected with HIV)

CD8+ T-cells were isolated from PBMC of healthy donors, activated by anti CD3/CD28 beads, and transduced with a CAR comprised of an inert NKG2D, a CD8 hinge and transmembrane domain, a costimulatory 4-1BB domain, and CD3☐. These CAR-T cells are referred to as convertibleCAR-cells. These convertibleCAR-T cells were only able to indirectly bind broadly neutralizing HIV antibodies that were fused to a modified, non-natural ligand cognate to the inert NKG2D receptor of the convertibleCAR. Untransduced CD8 T-cells from the same donor were also prepared in parallel as a negative control. Four HIV-specific MicAbodies were made based on the sequence of 3BNC60, 3BNC117, PGT121 and 10-1074 broadly neutralizing antibodies (SEQ ID NO.s 161 and 162 (3BNC60), MicAbody heavy and light chains respectively; 163 and 164 (3BNC117) MicAbody heavy and light chains, respectively; 165 and 166 (PGT121) MicAbody heavy and light chains, respectively; 167 and 168 (10-1074) MicAbody heavy and light chains, respectively) These MicAbodies bind to specific epitopes of the HIV gp160 envelope molecules. The targeted epitope bound by 3BNC60 and 3BNC117 is SEQ ID NO.:169; by PGF12 and 10-1074 is SEQ ID NO.: 170; (Deng K, Pertea M, Rongvaux A, Wang L, Durand C M, Ghiaur G, Lai J, McHugh H L, Hao H, Zhang H, J B, Gurer C, Murphy A J, Valenzuela D M, Yancopoulos G D, Deeks S G, Strowig T, Kumar P, Siliciano J D, Salzberg S L, Flavell R A, Shan L, Siliciano R F *Broad CTL response is required to clear latent HIV-1 due to dominance of escape mutations.* Nature. 2015 Jan. 15; 51'7(7534) p. 381-5.). MicAbodies targeting CD20 or HER2 were also deployed as negative controls.

Human tonsil cells from 4 healthy donors were processed to create Human Lymphoid Aggregate Culture (HLAC). HLAC cells were overlaid on 293T cells pre-transfected with DNA corresponding to R5-tropic HIV-1 and the GFP reporter gene. After 24 h, the HLAC cells were removed, and the spreading HIV infection was allowed to continue for 4 more days. The GFP-positive infected HLAC cells were then exposed to untransduced CD8 T-cells or to convertibleCAR-T cells armed with the indicated MicAbodies and cultured for 48 hours in the presence of 5 μM Saquinavir to prevent further viral spread. The cells were then collected by centrifugation, washed, and stained to assess viability in the infected and uninfected cells using an LSRII flow cytometer.

Figure 7:
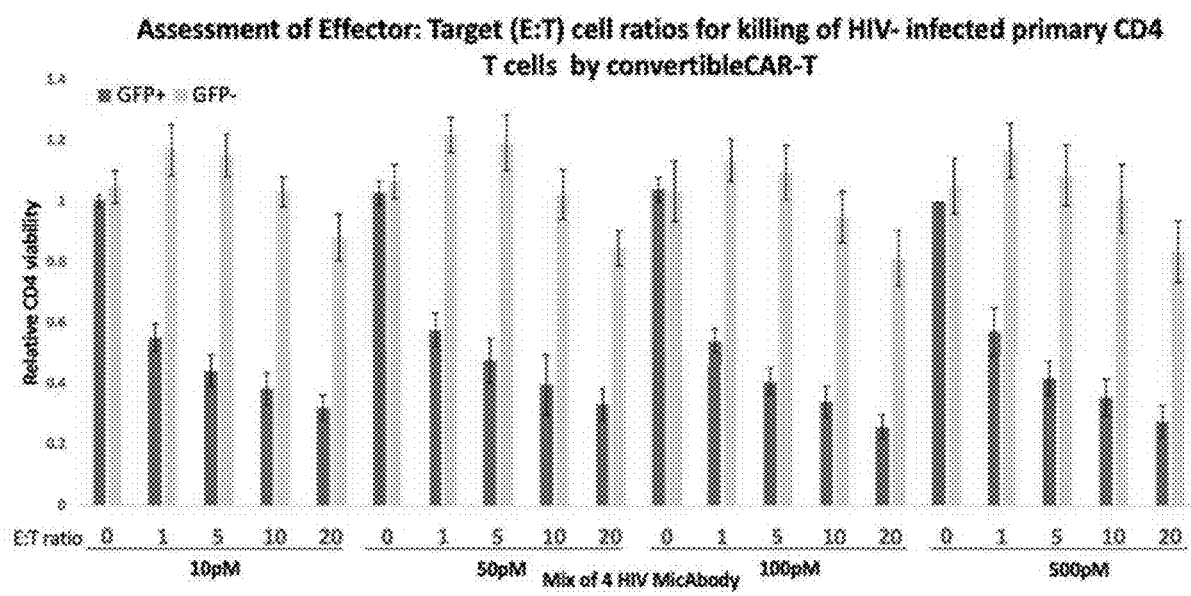
FIG. 7. Assessment of Effector: Target (E:T) cell ratios for killing of HIV-infected primary CD4 T cells by CAR-T cells with different concentrations of the specific HIV-targeted MicAbodies. One million primary tonsil derived cells infected with Bal-GFP R5 virus (~10% infection; $1 \times 10^4$ infected cells) were incubated with $1 \times 10^5$ untransduced CD8 (0:1) or with $1 \times 10^4$ (1:1) or $2 \times 10^5$ (20:1) CAR-T cells in the presence of different concentrations of the four different broadly neutralizing HIV MicAbodies. Cells were stained 24 hrs later and assessed by flow cytometry. Cells were gated on single cell/live/CD3+/CD8− cells either expressing or not expressing GFP. Results averaged from 3 studies are shown.

Assessment of Effector: Target (E:T) cell ratios for killing of HIV-infected primary CD4 T cells by CAR-T cells with different concentrations of the specific HIV-targeted MicAbodies. As described above, one million primary tonsil derived cells infected with Bal-GFP R5 virus (~10% infection; $1 \times 10^4$ infected cells) were incubated with $1 \times 10^5$ untransduced CD8 (0:1) or with $1 \times 10^4$ (1:1) or $2 \times 10^5$ (20:1) CAR-T cells in the presence of different concentrations of the four different broadly neutralizing HIV MicAbodies. Cells were stained 24 hrs later and assessed by flow cytometry. Cells were gated on single cell/live/CD3+/CD8− cells either expressing or not expressing GFP. Results averaged from 3 studies are shown in FIG. 7. In these studies, combining HIV specific MicAbodies and convertibleCAR-T cells led to specific killing of tonsillar cells infected by R5 HIV virus. Optimal effector:target ratio for killing ranged between 1:1 to 10:1 with no reduction in viability of uninfected cells. Killing was highly restricted to infected cells, i.e. those expressing GFP. GFP-cells present in the same culture showed little or no reduction in cell number (Figures B and C; GFP+ versus GFP−). Additionally, no killing of uninfected cells occurred and no killing of infected cells occurred when donor-matched untransduced CD8 T-cells or non-HIV-targeting MicAbodies were used (e.g. CD20-targeting MicAbody or Her2-targeting MicAbody)

Specific killing of R5 virus infected primary CD4 cells by CAR-T combined with specific HIV MicAbody. One million primary tonsil derived cells infected with Bal-GFP R5 virus (~1×$10^4$ infected cells) were incubated with 1×$10^5$ CAR-T cells in the presence of different concentrations of the HIV-specific MicAbodies or the B-cell specific CD20-targeting MicAbody or a HER2-targeting MicAbody (Her2). Cells were stained 24h later and analyzed by flow cytometry. Cells were gated on single cell/live/CD3+/CD8− and either GFP+ or GFP−. Results averaged from 4 studies are shown in FIG. 8.

Specific killing of F4 transmitted/founder virus infected primary CD4 cells by CAR-T combined with specific HIV MicAbody. One million primary tonsil derived cells infected with F4-GFP (T/F) virus (~1×$10^4$ infected cells) were incubated with 1×$10^5$ convertibleCAR-T cells in the presence of different concentrations of the 4 distinct 11W-specific MicAbodies, the CD20-targeting MicAbody (Ritux) or the HER2-targeting MicAbody (Her2). Cells were stained 24h later and followed with flow cytometry. Cells were gated on single cell/live/CD3+/CD8− and either GFP+ or GFP−. The results are depicted in FIG. 9. Effective killing was observed when cells infected with the R5 virus or infected with the F4 transmitted/founder HIV virus representing a viral strain that successfully passed horizontally from one person to another.

Example 14 (CAR-T and MicAbody Killing of Reactivated Latently Infected Reservoir Cells from Aviremic Patients Chronically Infected with HIV and on ART)

Figure 10:
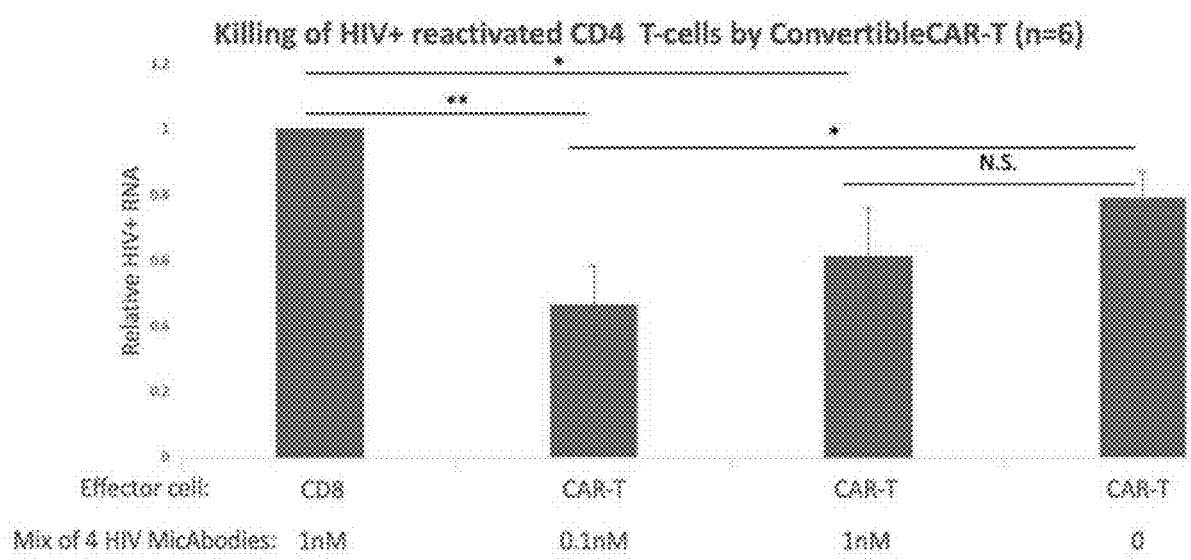
FIG. 10. CAR-T and MicAbody Killing of Reactivated Latently Infected Reservoir Cells from Aviremic Patients Chronically Infected with HIV and on ART. CD4+ T-cells isolated by no-touch negative selection from PBMC collected from known HIV-infected patients on ART and reactivated for 72 hrs with 100 nM phorbal myristate acetate (PMA)+1 uM Ionomycin. The cells were then washed twice and incubated for 48 hours with convertible CAR-T cells or untransduced CD8 T cells in the presence of 0.1 or 1 nM of a mixture of equal concentrations of HIV bNAb-based MicAbodies (3BNC60, 3BNC117, PGT121 and 10-1074) designated MIX. Cells were then centrifuged, and RNA was extracted from the cell pellets. Cell-associated HIV RNA was measured by ddPCR.

Peripheral blood mononuclear cells (PBMCs) from 6 aviremic HIV-positive individuals on ART were obtained by continuous flow centrifugation leukapheresis followed by density centrifugation of cells on Ficoll-Hypaque gradients. Resting CD4+ T lymphocytes were then isolated by "no touch" negative antibody depletion. Cells were cultured in RPMI medium supplemented with 10% fetal bovine serum and penicillin/streptomycin. 10 million resting CD4+ lymphocytes were stimulated with 80 nM PMA+1 uM Ionomycin for 72 hours. After reactivation, the cells were incubated for 48 hrs with CAR-T or donor-matched untransduced CD8 cells with different MicAbodies in the presence of 5 µM Saquinavir. The cells were collected by centrifugation at 300 g for 10 minutes. The cell pellets were then lysed and the RNA extracted using an RNeasy kit (Qiagen). A Superscript III One-Step RT-PCR system was used to generate cDNA and concomitantly pre-amplify viral mRNA (i.e. 10-cycles pre-amplification) before analysis and quantification by droplet digital PCR (ddPCR). CD4+ T-cells isolated by no-touch negative selection from PBMC collected from known HIV-infected patients on ART and reactivated for 72 hrs with 100 nM phorbal myristate acetate (PMA)+1 uM Ionomycin. The cells were then washed twice and incubated for 48 hours with convertibleCAR-T cells or untransduced CD8 T cells in the presence of 0.1 or 1 nM of a mixture of equal concentrations of HIV bNAb-based MicAbodies (3BNC60, 3BNC117, PGT121 and 10-1074) designated MIX in the Figure. Cells were then centrifuged, and RNA was extracted from the cell pellets. Cell-associated HIV RNA was measured by ddPCR. The results are depicted in FIG. 10. In the studies of this Example of reactivated latent reservoir cells (3 days with PMA+ionomycin) from aviremic infected individuals on ART (n=6), we observed that the CAR-T cells were able to effectively reduce the number of these reactivated reservoir cells by approximately 50% compared to donor-matched untransduced CD8 T cells+mix of MicAbodies. Inducible reservoir size was assessed by quantitating cell-associated HIV RNA in the presence and absence of inducer and effector cells with ddPCR.

These findings of Examples 13 and 14 collectively provide ex vivo proof of concept that convertibleCAR-T cells plus the cognate MicAbodies constructed with broadly neutralizing human IgG1 antibodies can be used to as a novel, efficient, and highly selective killing strategy for eliminating successfully reactivated HIV-infected cells within the latent HIV-1 reservoir.

What is claimed is:

1. A modified, non-natural ligand for a modified, non-natural NKG2D (Natural Killer Group 2D) receptor, wherein the ligand has an attached heterologous molecule that selectively binds a human immunodeficiency virus (HIV) protein present on the surface of a cell infected by HIV, wherein said heterologous molecule selectively binds to an epitope sequence that comprises an amino acid sequence selected from the group consisting of SEQ ID NO: 169 and SEQ ID NO: 170, and wherein the modified ligand with its attached heterologous molecule can selectively bind to a modified, non-natural NKG2D receptor of a chimeric antigen receptor (CAR)-cell and cause the destruction of the HIV-infected cell.

2. The modified, non-natural ligand of claim 1, wherein said modified, non-natural ligand comprises an amino acid sequence selected from the group consisting of SEQ ID NOs: 68-72.

3. The modified, non-natural ligand of claim 1, wherein said modified, non-natural ligand binds to a non-natural NKG2D receptor comprising an amino acid sequence selected from the group consisting of SEQ ID NO: 54 and SEQ ID NO: 154.

4. The modified, non-natural ligand of claim 1, wherein said modified, non-natural ligand is bound to a CAR-cell.

5. The modified, non-natural ligand of claim 4, wherein said CAR-cell comprises a modified, non-natural NKG2D receptor comprising an amino acid sequence selected from the group consisting of SEQ ID NO: 54 and SEQ ID NO: 154, and
   wherein a modified, non-natural ligand that comprises an amino acid sequence selected from the group consisting of SEQ ID NOs: 68-72 to which is attached a heterologous molecule or atom that does not bind an HIV protein is further bound to said CAR-cell.

6. The modified, non-natural ligand of claim 5, wherein said heterologous molecule or atom that does not bind an HIV protein modulates a function of the CAR-cell.

7. The modified, non-natural ligand of claim 6, wherein said function is a function selected from the group consisting of proliferation, differentiation, ablation, imaging, antagonism of immunosuppression, homing, and cytolysis of a cell not infected by HIV.

\* \* \* \* \*